United States Patent
Wang et al.

(10) Patent No.: US 11,191,847 B2
(45) Date of Patent: Dec. 7, 2021

(54) GENE THERAPY FOR TREATING HEMOPHILIA B

(71) Applicant: The Trustees of the University of Pennsylvania, Philadelphia, PA (US)

(72) Inventors: Lili Wang, Phoenixville, PA (US); James M. Wilson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 287 days.

(21) Appl. No.: 16/093,796

(22) PCT Filed: Apr. 13, 2017

(86) PCT No.: PCT/US2017/027400
§ 371 (c)(1),
(2) Date: Oct. 15, 2018

(87) PCT Pub. No.: WO2017/180861
PCT Pub. Date: Oct. 19, 2017

(65) Prior Publication Data
US 2019/0076550 A1     Mar. 14, 2019

Related U.S. Application Data

(60) Provisional application No. 62/323,375, filed on Apr. 15, 2016, provisional application No. 62/331,064, filed on May 3, 2016, provisional application No. 62/428,804, filed on Dec. 1, 2016.

(51) Int. Cl.
| | | |
|---|---|---|
| *C12N 15/79* | (2006.01) | |
| *C07H 21/04* | (2006.01) | |
| *A61K 48/00* | (2006.01) | |
| *C12N 15/86* | (2006.01) | |
| *A61P 7/04* | (2006.01) | |

(52) U.S. Cl.
CPC ........ *A61K 48/0008* (2013.01); *A61K 48/005* (2013.01); *A61K 48/0058* (2013.01); *A61K 48/0075* (2013.01); *A61K 48/0083* (2013.01); *C12N 15/86* (2013.01); *A61P 7/04* (2018.01); *C07H 21/04* (2013.01); *C12N 2750/14132* (2013.01); *C12N 2750/14143* (2013.01)

(58) Field of Classification Search
CPC .......... C12N 15/86; C12N 2750/14143; C07H 21/04
See application file for complete search history.

(56) References Cited

U.S. PATENT DOCUMENTS

| | | | |
|---|---|---|---|
| 6,596,535 B1 | 7/2003 | Carter | |
| 7,056,502 B2 * | 6/2006 | Hildinger | A61P 37/02 424/93.2 |
| 7,125,717 B2 | 10/2006 | Carter | |
| 7,456,683 B2 | 11/2008 | Takano et al. | |
| 8,030,065 B2 | 10/2011 | Gray | |
| 8,168,425 B2 | 5/2012 | Gray | |
| 2006/0136184 A1 | 6/2006 | Gustafsson et al. | |
| 2007/0243168 A1 | 10/2007 | Kay et al. | |
| 2012/0058102 A1 | 3/2012 | Wilson et al. | |
| 2013/0045186 A1 | 2/2013 | Gao et al. | |
| 2014/0032186 A1 | 1/2014 | Gustafsson et al. | |
| 2015/0283267 A1 | 10/2015 | Vandendriessche et al. | |
| 2016/0229904 A1 | 8/2016 | Xiao et al. | |
| 2017/0233455 A1 | 8/2017 | Falkner et al. | |
| 2018/0110877 A1 | 4/2018 | Wilson et al. | |

FOREIGN PATENT DOCUMENTS

| | | |
|---|---|---|
| WO | WO-2011/126808 | 10/2011 |
| WO | WO-2013/049493 | 4/2013 |
| WO | WO 2014/064277 | 5/2014 |
| WO | WO-2015/012924 | 1/2015 |
| WO | WO 2017/180857 | 10/2017 |

OTHER PUBLICATIONS

Lisowski et al., 2015, US 20150376607 A1.*
Lee et al., 2015, GeneSeq Accession No. BCA51195, computer printout, pp. 18-20.*
Cabaniols J. et al., 2010, GeneSeq Accession No. AYA09574, computer printout, pp. 10-11.*
Stanek et al., 2019, US 20190111157 A1, effective filing date, Feb. 10, 2015.*
Kelly, J, 2014, GeneSeq Accession No. BBP99137, computer printout, pp. 1-3.*
Peters et al., 2007, GeneSeq Accession No. ALJ29634, computer printout, pp. 1-3.*
U.S. Department of Health and Human Services, Food and Drug Administration, "Guidance for Industry—cGMP for Phase 1 Investigational Drugs", pp. 1-20, Jul. 2008.
Antoniou et al., Efficient 3'-end formation of human beta-globin mRNA in vivo requires sequences within the last intron but occurs independently of the splicing reaction, Nucleic Acids Research, vol. 26(3):721-9, Mar. 1998.
Calcedo et al., Worldwide Epidemiology of Neutralizing Antibodies to Adeno-Associated Viruses, Journal of Infectious Diseases, vol. 199(3):381-390, Feb. 2009.
Gao et al., Adeno-associated viruses undergo substantial evolution in primates during natural infections, Proc. Natl. Acad. Sci. U.S.A., vol. 100 (10):6081-6086, May 2003.
Genbank Accession # P00740, The gene structure of human anti-haemophilic factor IX, Jul. 1986.
Genbank Accession No. J04514, Woodchuck hepatitis B virus (WHV8), complete genome, Aug. 1993.

(Continued)

*Primary Examiner* — Shin Lin Chen
(74) *Attorney, Agent, or Firm* — Howson & Howson LLP

(57) ABSTRACT

Compositions for the treatment of hemophilia B are provided. In certain embodiments, the composition is a recombinant adeno-associated virus (rAAV) comprising an AAVrh10 capsid and a vector genome packaged therein, wherein the vector genome comprises an AAV 5' inverted terminal repeat (ITR), a coding sequence for a human Factor IX (F9) having coagulation function operably linked to regulatory elements which direct expression of the human Factor IX in liver cells, and an AAV 3' ITR.

21 Claims, 36 Drawing Sheets

Specification includes a Sequence Listing.

(56) References Cited

OTHER PUBLICATIONS

GenBank Accession No. AA088201, capsid protein [Non-human primate Adeno-associated virus], May 2003.
GenBank Accession No. AF369965, Cloning vector pHelper, complete sequence, Jul. 2001.
GenBank Accession No. LI3470.1, Human thyroxine-binding globulin gene, complete cds, Jan. 1994.
GenBank Accession No. NC001401, Adeno-associated virus-2, complete genome, Aug. 2018.
GenBank Accession No. NM000133, *Homo sapiens* coagulation factor IX (F9), transcript variant 1, mRNA, Jan. 2019.
Genbank Accession No. X67082.1, *H.sapiens* AMBP gene transcription regulatory region, Dec. 1992.
GenBank Accession No. NC_000011.9, *Homo sapiens* chromosome 11, GRCh37.p13 Primary Assembly, Aug. 2013.
Grimm et al., Titration of AAV-2 particles via a novel capsid ELISA: packaging of genomes can limit production of recombinant AAV-2, Gene Therapy, vol. 6:1322-1330, Jul. 1999.
Lock et al., Absolute determination of single-stranded and self-complementary adeno-associated viral vector genome titers by droplet digital PCR, Hum Gene Ther Methods, vol. 25(2): 115-25, Apr. 2014 (Epub Feb. 2014).
McCarty et al., Self-complementary recombinant adeno-associated virus (scAAV) vectors promote efficient transduction independently of DNA synthesis, Gene Therapy, vol. 8(16): 1248-1254, Aug. 2001.
Mingozzi et al., Overcoming preexisting humoral immunity to AAV using capsid decoys, Sci Transl Med, vol. 5(194): 194ra92, Jul. 2013.
Miyatake et al., Transcriptional targeting of herpes simplex virus for cell-specific replication, J. Virol., vol. 71(7):5124-32, Jul. 1997.
Nathwani et al., Adenovirus-associated virus vector-mediated gene transfer in hemophilia B, N Engl J Med, vol. 365:2357-2365, Dec. 2011.
Nathwani et al., Long-term safety and efficacy of factor IX gene therapy in hemophilia B, New England Journal of Medicine, vol. 3 71(21): 1994-2004, Nov. 2014.
Sandig et al., HBV-derived promoters direct liver-specific expression of an adenovirally transduced LDL receptor gene, Gene Ther., vol. 3(11): 1002-9, Nov. 1996.
Sommer et al., Quantification of adeno-associated virus particles and empty capsids by optical density measurement, Molec. Ther., vol. 7:122-128, Jan. 2003.
Thomson et al., A comprehensive comparison of multiple sequence alignments, Nucl. Acids. Res., vol. 27(13):2682-2690, Jul. 1999.
Wang et al., Sustained correction of bleeding disorder in hemophilia B mice by gene therapy, PNAS, vol. 96:3 906-10, Mar. 1999.
Wang et al., A factor IX-deficient mouse model for hemophilia B gene therapy, Proceedings of the National Academy of Sciences, vol. 94(21): 11563-11566, Oct. 1997.
Wang et al., Sustained expression of therapeutic level of factor IX in hemophilia B dogs by AAV-mediated gene therapy in liver, Molecular Therapy, vol. 1(2)154-158, Feb. 2000.
Wobus et al., Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection, J. Virol. vol. 74(19):928 1-9293, Oct. 2000.
Wu et al., Effect of Genome Size on AAV Vector Packaging, Mol Ther., vol. 18(1):80-86, Jan. 2010.
Wu et al., Optimization of Self-complementary AAV Vectors for Liver-directed Expression Results in Sustained Correction of Hemophilia B at Low Vector Dose, Molecular Therapy, vol. 16(2):280-289, Feb. 2008.
International Search Report issued on International Patent Application No. PCT/US2017/027400, dated Sep. 22, 2017.
Written Opinion issued on International Patent Application No. PCT/US2017/027400, dated Sep. 22, 2017.
International Patent Application No. PCT/US2016/042472.
U.S. Appl. No. 62/266,341, filed Dec. 11, 2015.
U.S. Appl. No. 62/266,347, filed Dec. 11, 2015.
U.S. Appl. No. 62/266,351, filed Dec. 11, 2015.
U.S. Appl. No. 62/266,357, filed Dec. 11, 2015.
U.S. Appl. No. 62/322,055, filed Apr. 13, 2016.
U.S. Appl. No. 62/322,071, filed Apr. 13, 2016.
U.S. Appl. No. 62/322,083, filed Apr. 13, 2016.
U.S. Appl. No. 62/322,098, filed Apr. 13, 2016.
Extended European Search Report issued on European Patent Application No. 17734160.0, dated Sep. 25, 2019.
Costa et al. Mol Cell Biol, Dec. 1986;6(12):4697-708.
Costa et al. Mol Cell Biol, Jan. 1988;8(1):81-90.
Maeda et al. Mol Biol Med. Aug. 1986;3(4):329-38.
Carroll, J., Analysts write off Dimension's lead program after seeing weak data on hemophilia B, shares plunge, Endpoint News, Jan. 31, 2017, https://endpts.com/analysts-write-off-dimensions-lead-program-after-seeing-weak-data-on-hemophilia-b-shares-plunge/.

\* cited by examiner

Figure 3 - Alignment of human FIX coding sequence

FIGURE 3 (cont'd) - Alignment of human FIX coding sequence

Sequence identity: 75.1%

Figure 4- Alignment of ABP enhancer

Homo sapiens chromosome 9, alternate assembly CHM1_1.1
Sequence ID: ref|NC_018920.2| Length: 141362467 Number of Matches: 1

Range 1: 116989759 to 116989857 Genbank Graphics

| Score | Expect | Identities | Gaps | Strand |
|---|---|---|---|---|
| 165 bits(89) | 8e-39 | 98/99(97%) | 1/99(1%) | Plus/Minus |

Features:

```
Query  2    GTTAATTTTAAAAGCAGTCAAAGTCAAAGTG-CCCTTGCGAGCATTTACTCTCTCTG  60
            ||||||||||||||||||||||||||||||| |||||||||||||||||||||||||
Sbjct  116989857  GTTAATTTTAAAAGCAGTCAAAGTCAAAGTGCCCCTTGCGAGCATTTACTCTCTCTG  116989798

Query  61   TTTGCCTCTGGTTAATAATCTCAGGAGCACAAACATTCCT  99
            ||||||||||||||||||||||||||||||||||||||||
Sbjct  116989797  TTTGCCTCTGGTTAATAATCTCAGGAGCACAAACATTCCT  116989759
```

Figure 5 - Alignment of TBG promoter

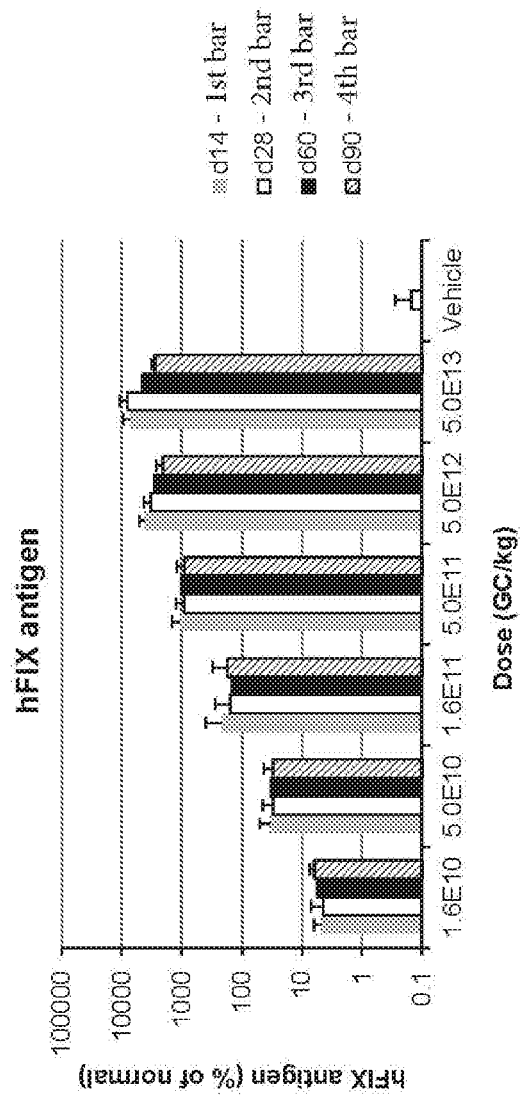
Figure 6. hFIX expression levels determined by ELISA

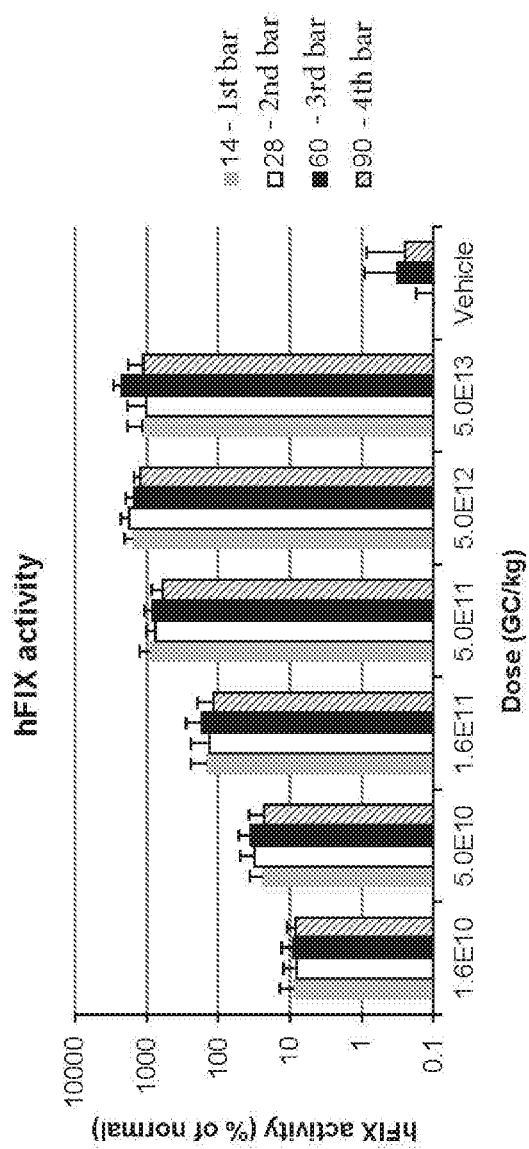
Figure 7. hFIX activity levels determined by APTT assay

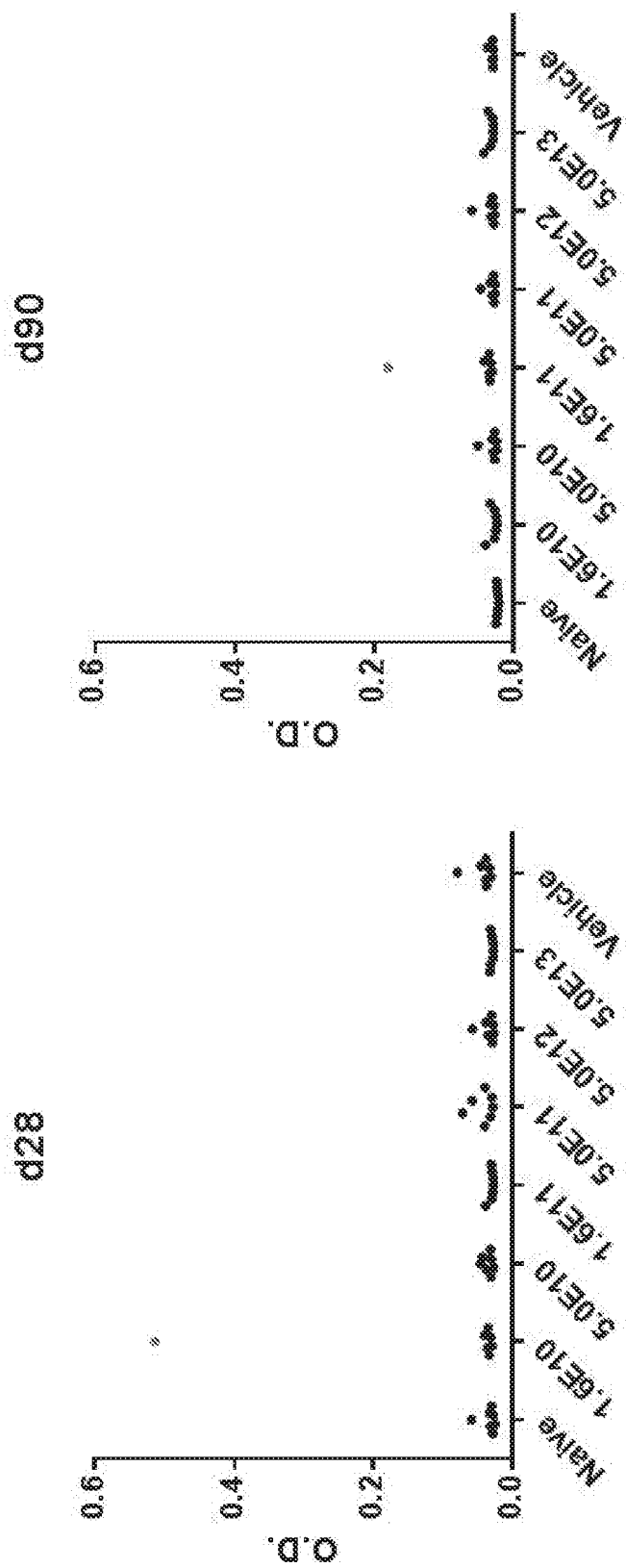
Figure 8. Anti-hFIX IgG in mouse serum determined by solid-phase ELISA.

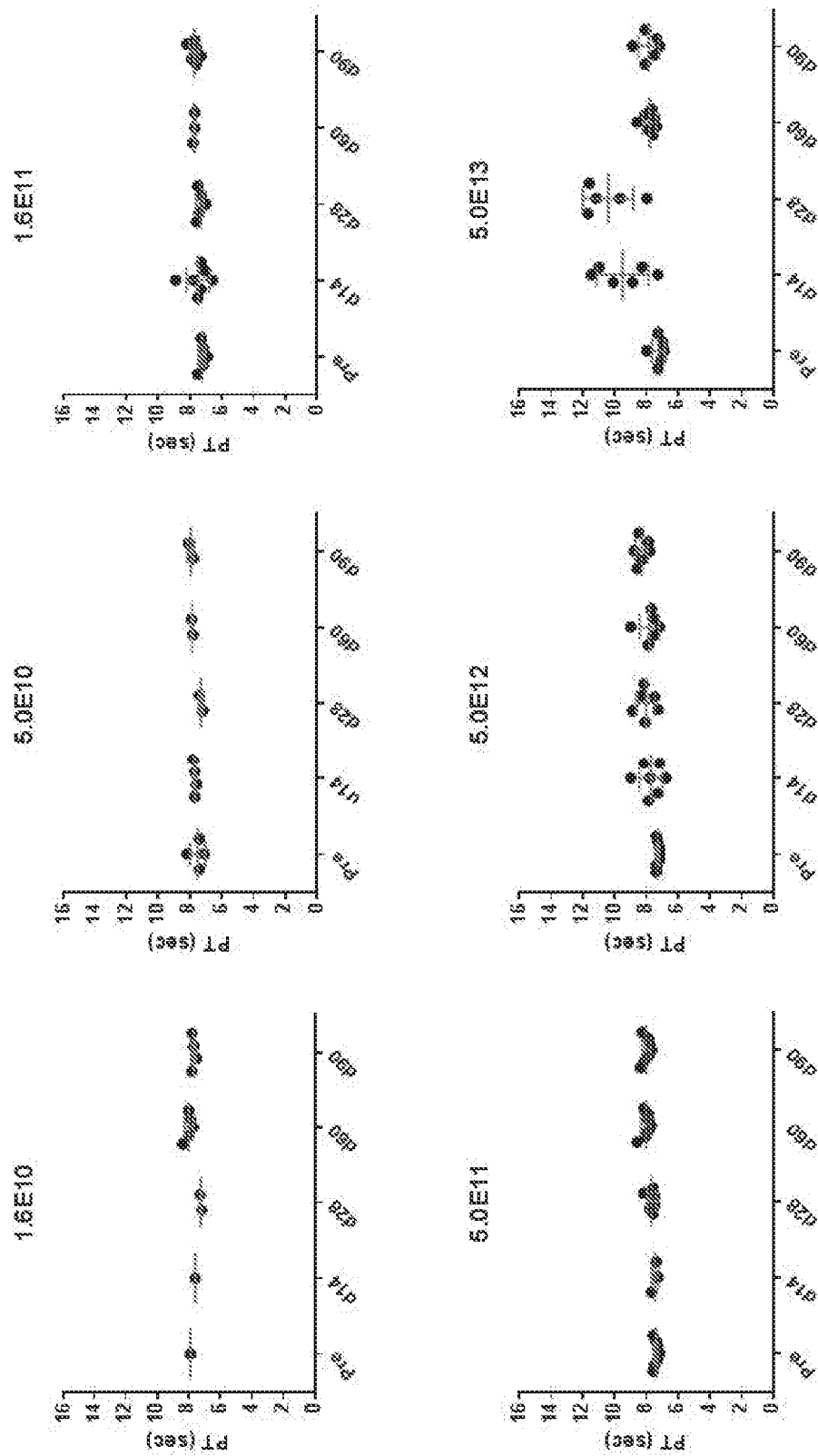
Figure 9. Transient prolongation of partial thromboplastin (PT) time in animals treated with the highest dose of vector.

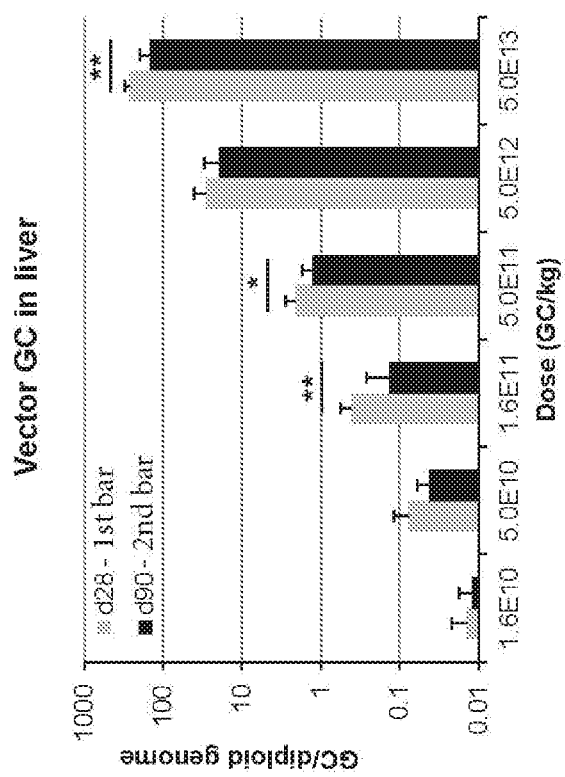
Figure 10. Vector genome copies in liver determined by QPCR. * $P < 0.05$; ** $P < 0.001$, Mann Whitney test (n=7).

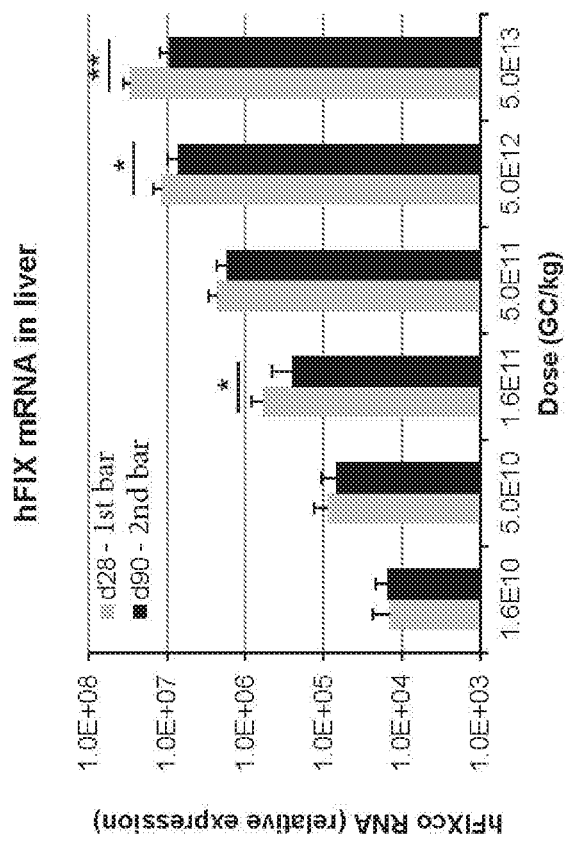
Figure 11. Relative expression of hFIXco mRNA in liver determined by RT-QPCR. * $P < 0.05$; ** $P < 0.001$, Mann Whitney test (n=7).

AAV3B

AAV5

FIGURE 22
2 weeks
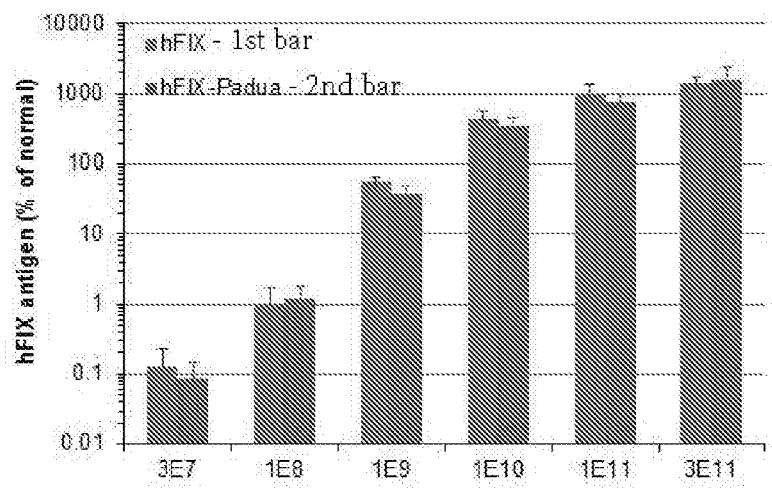
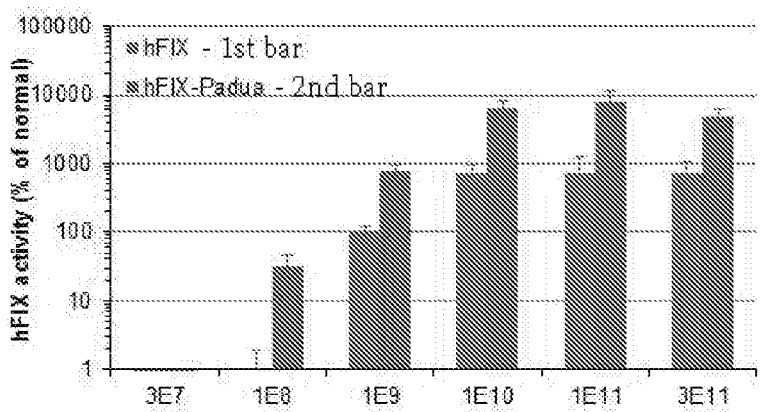

Time Course of Prothrombin Time (PT)

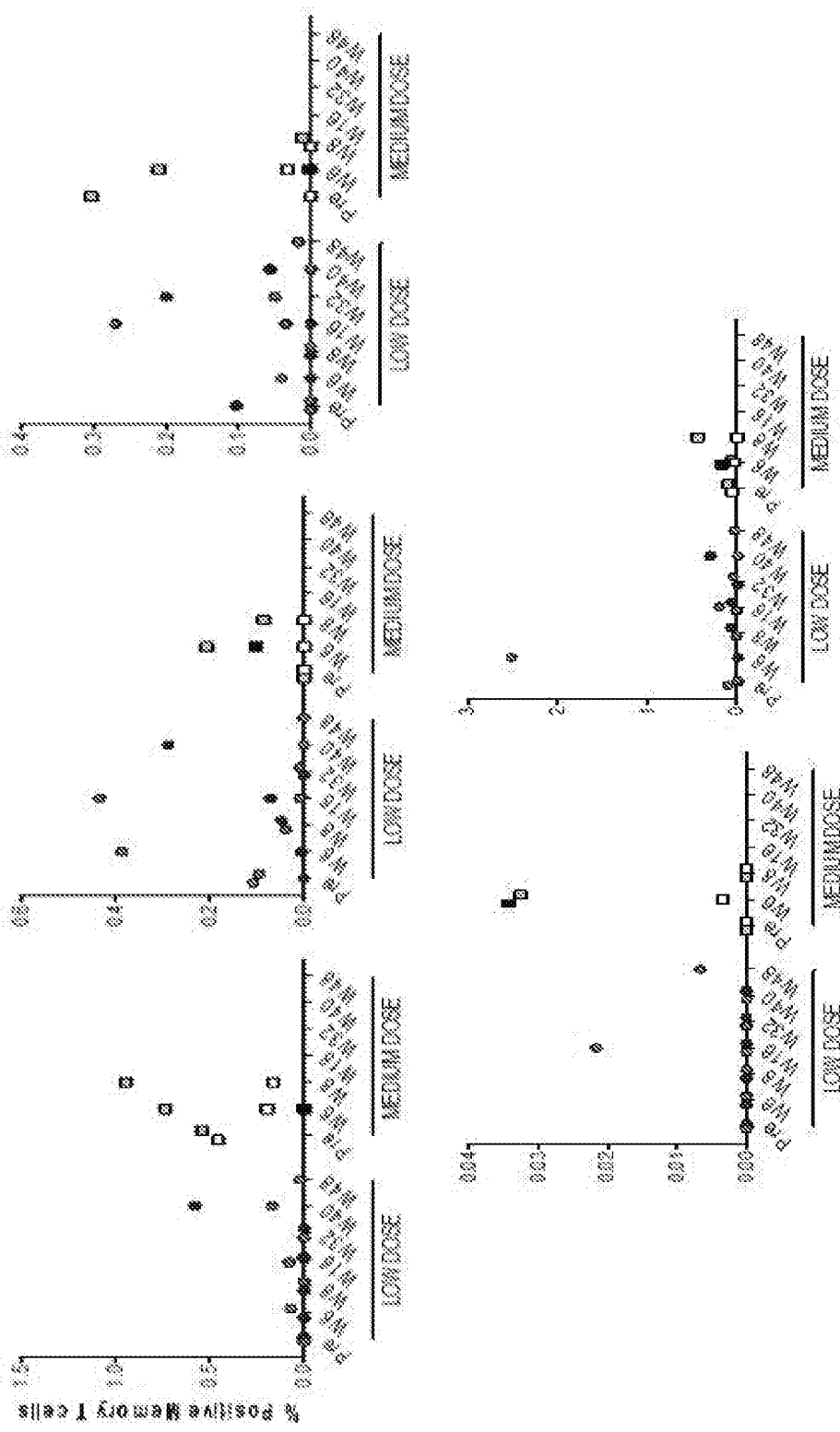

FIGURE 30A  Human FIX amino acid sequence and mutation per subject:

MQRVNMIMAESPGLITICLLGYLLSAECTVFLDHENANKILNR⁴³PKRYNSGKLEEFVQGNLERECMEEKC
SFEEAREVFENTERTTEFWKQYVDGDQCESNPCLNGGSCKDDINSYECWCPFGFEGKNCELDVTCNIKN
GRCEQFCKNSADNKVVCSCTEGYRLAENQKS¹⁶⁹CEPAVPFPCGRVSVSQTSKLTRAETVFPDVDYVNSTE
AETILDNITQSTQSFNDFTRVGGEDAKPGQFPWQ²⁴¹VVLNGKVDAFCGGSIVNEKWIVTAAHCVETGV
KITVVAGEHNIEETEHTEQKRNVIRIIPHHNYNAAINKYNHDIALLELDEPLVLNSYVTPICIADKEYTNIFLKF
GSGYVSGWGRVFHKGRSALVLQYLRVPLVDRATCLRSTKFTI³⁹⁰YNNMFCAGFHEGGRDSCQGDSGGPH
VTEVEGTSFLTGIISWGEECAMKGK⁴⁴⁰YGIYTKVSRYVNWIKEKTKLT

FIGURE 30B  MHC Class I binding prediction for FIX mutation per subject

| 1001-001 subject. | B18 | B40 | C03 | C07 |
|---|---|---|---|---|
| K440E | 66 | 18 | 77 | 132 |

| 1001-002 subject. | B14 | B35 | C04 | C08 |
|---|---|---|---|---|
| I390F | 6 | 72 | 121 | 68 |

| 1007-001 subject. | B13 | B44 | C06 | C16 |
|---|---|---|---|---|
| Non-coding | \ | \ | \ | \ |

| 1002-002 subject. | B08 | B35 | C04 | C07 |
|---|---|---|---|---|
| R43W | 9 | 18 | 4 | 22 |

| 4401-002 subject. | B07 | B35 | C04 | C07 |
|---|---|---|---|---|
| Q241Q, Silent | 15 | 5 | 137 | 51 |

| 4402-003 subject. | B14 | B44 | C05 | C08 |
|---|---|---|---|---|
| S169P | 3 | 5 | 4 | 3 |

GENE THERAPY FOR TREATING HEMOPHILIA B

CROSS REFERENCE TO RELATED APPLICATIONS

This is a National Stage Entry under 35 U.S.C. 371 of International Patent Application No. PCT/US2017/027400, filed Apr. 13, 2017, which claims the benefit under 35 USC 119(e) of U.S. Provisional Patent Application No. 62/323,375, filed Apr. 15, 2016, U.S. Provisional Patent Application No. 62/331,064, filed May 3, 2016, and U.S. Provisional Patent Application No. 62/428,804, filed Dec. 1, 2016. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-16-7797PCT_ST25.txt".

1. INTRODUCTION

The application describes embodiments useful for gene therapy for treating hemophilia B.

2. BACKGROUND

Hemophilia B is an X-linked bleeding disorder caused by abnormalities in the function or expression of blood coagulation Factor IX (FIX). Females who have one normal allele and one mutant allele have sufficient FIX levels to be asymptomatic. Thus there is not a strong requirement for a gene therapy product for hemophilia B to deliver more than 50% of normal FIX blood levels. Because males have a single X chromosome, presence of one abnormal allele leads to a clinical presentation of hemophilia. Milder cases demonstrate excessive bleeding in response to surgery or trauma; with more severe cases, spontaneous internal bleeding may happen in any part of the body, with bleeding into joints being most common. Chronic joint deformities may occur from bleeding, and intracerebral hemorrhage can occur, the latter with potentially life-threatening consequences.

The molecular basis of hemophilia B lies in the gene that encodes blood coagulation FIX. The incidence of hemophilia B in the United States is about 1:25,000 live male births. Characterization of mutant alleles has revealed a variety of mutations including deletions, insertions, missense mutations, and nonsense mutations. This genotypic heterogeneity leads to variable consequences in the biochemical function. Disease severity ranges from mild to severe, depending on the residual FIX activity, with the majority of patients falling into the moderate-to-severe categories. Patients with 5% to less than 50% of normal activity have mild disease, and they may not show symptoms except in cases of trauma or surgery. Patients with 1-5% of normal activity have moderate disease, have excessive bleeding with trauma and may experience spontaneous bleeding. Patients with less than 1% of normal activity have severe disease, with frequent spontaneous bleeding, especially into joints and muscle. Patients with severe hemophilia are typically treated with regular injections of purified or recombinant FIX (prophylaxis) to prevent spontaneous bleeds. Despite the effectiveness of these regimens, they all do require frequent burdensome intravenous infusions. Furthermore, the nature of these treatment regimens leads to the risk of trough levels of Factor IX, which is related to the risk of breakthrough bleeding episodes. The patient with severe hemophilia. B (Factor IX levels <1% of normal) is still dependent on frequent intravenous infusions and is still at risk for breakthrough bleeding complications.

Hemophilia may be first diagnosed in an infant boy when prolonged bleeding is observed such as after a heel stick, a blood draw or circumcision but also may be diagnosed when the child starts crawling and walking, when large bruises may result from even small falls. Patients with mild disease, having 5-50% of normal FIX activity, typically only show symptoms of abnormal bleeding in response to injury, including surgery or tooth extraction. In patients with moderately severe disease, having 1-5% of normal FIX activity, spontaneous hemorrhages may also occur, but are infrequent. In the most severe form of the disease (<1% of FIX activity; about 60% of all hemophilia B), frequent spontaneous hemorrhages are the distinguishing characteristic. These result in muscle hematomas, hemorrhages in the central nervous system, and hemophilic arthropathy—damage caused by repetitive bleeding episodes in the joints. Without appropriate treatment with FIX replacement therapy, the disease can have disabling or even fatal results. This genetic information strongly supports the idea that raising the levels of FIX to >1% of normal activity has a large beneficial effect on disease course in severe hemophiliacs, with potentially even better results at 5% of normal activity. Prevention of bleeding, rather than just treating bleeding episodes, can have a significantly improved outcome, particularly in preventing disabling joint damage.

In the developed world, where the Factor IX protein replacement products are readily available, patients can be treated with the products in response to injury, or in the case of severe hemophilia, patients can be treated prophylactically. Patients with hemophilia B with access to protein replacement now have a normal life expectancy. However, there is still morbidity from spontaneous bleeding in patients with insufficient prophylaxis. This can result from several factors. Patients may develop neutralizing antibodies (inhibitors) to Factor IX, reducing its ability to participate in the clotting cascade. In the moderate to mildly affected groups, spontaneous bleeds can occur, but because they are rare, these patients are not usually given prophylactic therapy to prevent those bleeds. Interestingly, joint disease may have become more common in the less severe patients than in severe patients due to the latter group's use of prophylaxis. Prophylaxis requires frequent venipuncture, which in children may result in the need for a venous access device, and also takes time to deliver, both to prepare the therapeutic and for the infusion itself. Finally, in many parts of the world, these clotting factors are not readily available to patients, nor does every patient adhere to the prescribed regimen.

The limitations of Factor IX (FIX) protein replacement have been described above. Although FIX protein replacement therapy is available to patients in the developed world, it requires a lifetime of intravenous infusions every few days for optimal prophylaxis, due to the relatively short half-life of FIX. Although moderately affected patients could benefit from prophylaxis, especially to prevent joint bleeding, they typically do not use a prophylactic regimen. Gene replacement therapy is expected to be effective, since hemophilia is caused by the lack of the single gene product, FIX. Continuous synthesis of FIX by the liver, recapitulating to an extent the normal state, is expected to be even more effective at preventing bleeds than bolus infusions of recombinant FIX. Patients would also be able to avoid the risks and inconvenience of regular FIX infusion. It also has a greater potential to treat hemophilia patients in the developing world, as a single treatment is anticipated to provide many years of therapy. Tight regulation of levels of FIX expression using gene therapy is not expected to be required, due to the known efficacy of a wide range of FIX levels in hemophilia B animal models as well as human experience with FIX protein replacement.

Liver-targeted recombinant adeno-associated virus (rAAV) expressing canine factor IX cDNA in animals for Hemophilia B have been described. See, e.g., Wang, Lili, et al. "Sustained correction of bleeding disorder in hemophilia B mice by gene therapy." Proceedings of the National Academy of Sciences 96.7 (1999): 3906-3910; and Wang, Lili, et al. "Sustained expression of therapeutic level of factor IX in hemophilia B dogs by AAV-mediated gene therapy in liver." Molecular therapy 1.2 (2000): 154-158, each of which is incorporated herein by reference. A human factor IX in AAV vector was generated by John T. Gray and a clinical trial using such vectors has been described by Nathwani et al. Please see, U.S. Pat. Nos. 8,030,065; 8,168,425; Nathwani, Amit C., et al. "Adenovirus-associated virus vector—mediated gene transfer in hemophilia B." N Engl J Med 2011.365 (2011): 2357-2365; and Nathwani, Amit C., et al. "Long-term safety and efficacy of factor IX gene therapy in hemophilia B." New England Journal of Medicine 371.21 (2014): 1994-2004, each of which is incorporated herein by reference. However, adverse events were observed, such as an asymptomatic elevation in the alanine aminotransferase (ALT) level.

What are needed are safe and effective treatments for Hemophilia B.

3. SUMMARY

Described herein are AAV gene therapy vectors for delivering normal human FIX to a subject in need thereof, following intravenous administration of the vector resulting in long-term, perhaps 10 years or more, of clinically meaningful correction of the bleeding defect. The subject patient population is patients with severe hemophilia B. The intended vector dose described herein is expected to deliver FIX blood levels of approximately 5% or greater. The goal for the AAV vector treatment is conversion of severe hemophilia B patients to either moderate or mild hemophilia B thus relieving such patients of the need to be on a prophylaxis regimen.

The gene therapy product described herein provides multiple important advantages to currently available prophylactic approaches to the management of severe Hemophilia B. First, preclinical results with the investigational product are consistent with its potential to achieve circulating levels of Factor IX of 5% or more of normal, levels which would be transformative in the target patient population. Second, the product should lead to effectively constant Factor IX blood levels, avoiding the trough levels currently seen with administration of exogenous factor. Third, by only requiring a single administration, the requirement for frequent intravenous administrations could be reduced for an extended period of time, perhaps for a decade or more.

This application provides the use of a replication deficient adeno-associated virus (AAV) to deliver a human Factor IX (hFIX) gene to liver cells of patients (human subjects) diagnosed with hemophilia B. The recombinant AAV vector (rAAV) used for delivering the hFIX gene ("rAAV.hFIX") should have a tropism for the liver e.g., an rAAV bearing an AAVrh.10 capsid), and the hFIX transgene should be controlled by liver-specific expression control elements. In one embodiment, the expression control elements include one or more of the following: an alpha-1 microglobulin/bikunin enhancer; a thyroid hormone binding globulin promoter (TBG); a human beta globin IVS2 intron; a WPRE; and a polyA signal. Such elements are further described herein.

The coding sequence for hFIX is, in one embodiment, codon optimized for expression in humans. Such sequence may share less than 80% identity to the native hFIX coding sequence (SEQ ID NO: 1). In one embodiment, the hFIX coding sequence is that shown in SEQ ID NO: 2. In one embodiment, the hFIX coding sequence is that shown in SEQ ID NO: 13.

In another aspect, provided herein is an aqueous suspension suitable for administration to a hemophilia B patient which includes the rAAV described herein. In some embodiments, the suspension includes an aqueous suspending liquid and about $1\times10^{12}$ to about $5\times10^{13}$ genome copies (GC) of the rAAV/mL. The suspension is, in one embodiment, suitable for intravenous injection. In other embodiment, the suspension further includes a surfactant, preservative, and/or buffer dissolved in the aqueous suspending liquid.

In another embodiment, provided herein is a method of treating a patient having hemophilia B with an rAAV as described herein. In one embodiment, about $1\times10^{11}$ to about $1\times10^{13}$ genome copies (GC) of the rAAV/kg patient body weight are delivered the patient in an aqueous suspension. All ranges described herein are inclusive of the endpoints.

The goal of the treatment is to functionally replace the patient's defective hFIX via rAAV-based liver-directed gene therapy as a viable approach to treat this disease and improve response to current therapies. The embodiments described in the application are based, in part, on the development of therapeutic compositions and methods that allow for the safe delivery of efficacious doses; and improved manufacturing methods to meet the purification production requirement for efficacious dosing in human subjects.

4. BRIEF DESCRIPTION OF THE DRAWINGS

FIG. 1. Schematic representation of AAV.LSP.IVS2. hFIXco3T.WPRE.bGH cassette.

FIG. 2. Schematic representation of pENN.AAV.LSP. hFIXco3T.WPRE.bGH.KanR cis plasmid.

Figure 3:
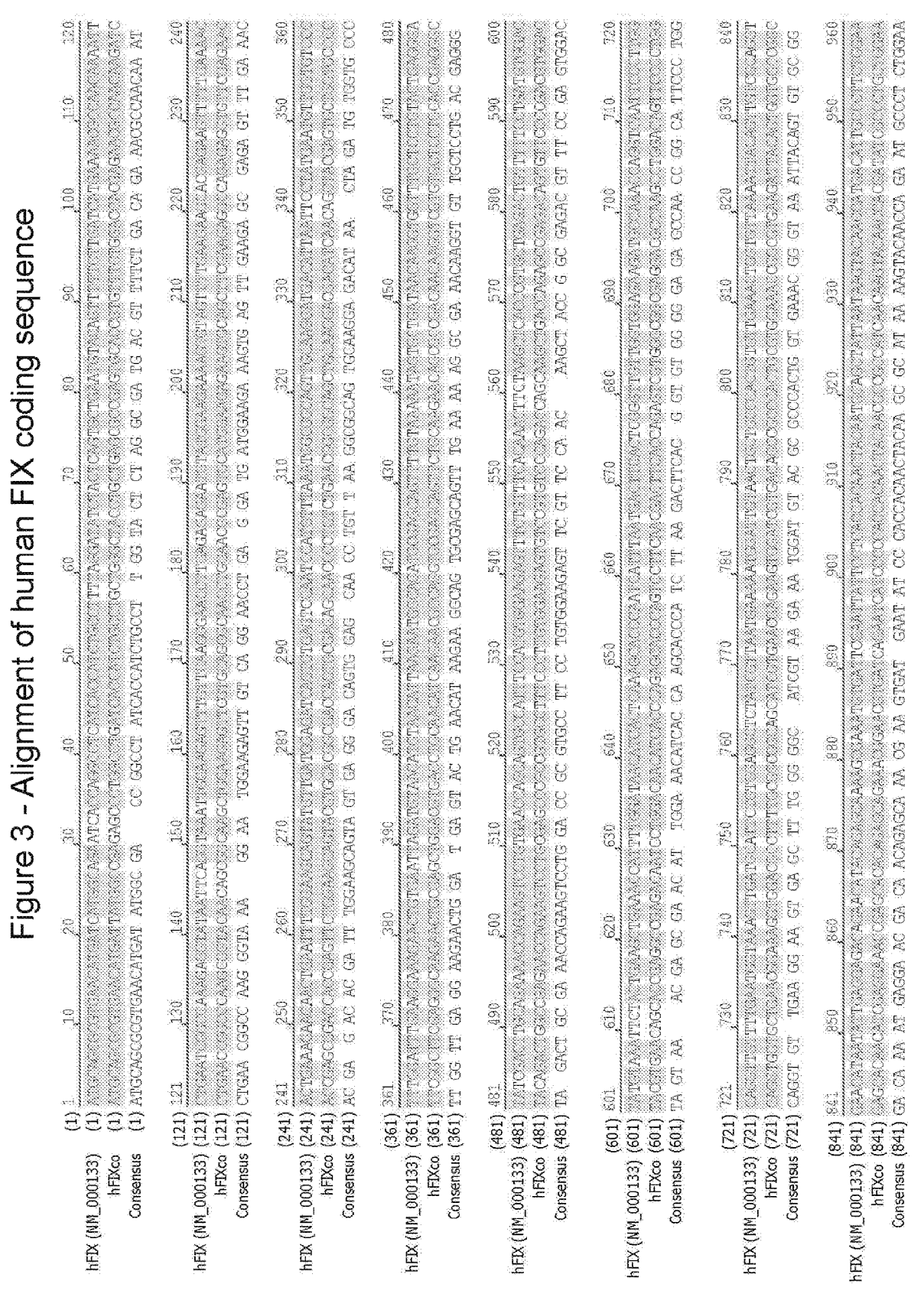

FIG. 3. Alignment of human FIX (NM_000133) coding sequence (nucleotides 29 to 1412 of SEQ ID NO: 1) with codon-optimized hFIX (hFIXco) sequence (nucleotides 1 to 1383 of SEQ ID NO: 2).

FIG. 4. Alignment of human ABP enhancer SEQ ID NO: 18; bottom sequence) with APB enhancer described herein (nucleotides 2 to 99 of SEQ ID NO: 4; top sequence).

FIG. 5. Alignment of human TBG promoter SEQ ID NO: 19; bottom sequence) with TBG promoter described herein (nucleotides 26 to 496 of SEQ ID NO: 5; top sequence).

FIG. 6. Graph showing hFIX expression levels in 4 FIX-KO mice in a dose response experiment, as determined by ELISA. Experiment as described in Section 8.4.1.

FIG. 7. Graph showing hFIX expression levels in 4 FIX-KO mice in a dose response experiment, as determined by APTT assay. Experiment as described in Section 8.4.1.

FIG. 8. Graphs showing absence of anti-hFIX IgG in 7 FIX-KO mice in a dose response experiment, as determined by solid-phase ELISA. Experiment as described in Section 8.4.1.

FIG. 9 are 6 graphs showing PT (prothrombin time) in FIX-KO male mouse plasma, following AAV vector administration. PT was determined using a Stago ST Art Start Hemostasis Coagulation Analyzer set to PT mode and Dade Innovin Reagent (Reference #B4212-40). Normal PT values for male FIX-KO mice range from 6.8-8.2 seconds with mean and standard deviation of 7.3±0.3 seconds, respectively. Experiments as described in Section 8.4.1.

FIG. 10. Graph showing Vector genome copies in liver determined by QPCR. * P<0.05; ** P<0.001, Mann Whitney test (n=7). Experiments as described in Section 8.4.1.

FIG. 11. Graph showing relative expression of hFIXco mRNA in liver determined by RT-QPCR. * P<0.05; ** P<0.001, Mann Whitney test (n=7). Experiments as described in Section 8.4.1.

FIG. 12. Manufacturing Process Flow Diagram

FIG. 13. rAAVrh.10.LSP.hFIXco vector was assessed at six doses after intravenous administration: $8\times10^7$, $2.7\times10^8$, $2.7\times10^9$, $2.7\times10^{10}$, $2.7\times10^{11}$ and $8\times10^{11}$ GC/mouse. Mice were bled at 2 and 4 weeks following vector administration and Factor IX antigen and activity levels were determined by hFIX ELISA and aPTT, respectively. Experiments as described in Section 8.2.

FIG. 14. A dose-response study was conducted in C57B1/6 male mice. rAAVrh.10.LSP.hFIXco was assessed at four doses after intravenous administration: $7\times10^8$, $2.3\times10^9$, $7\times10^9$, and $2.3\times10^{10}$ GC/mouse Factor IX levels were observed above therapeutic levels (5% of normal; 100%=5 ug/ml) at a dose of $2.3\times10^9$ GC/mouse ($1.1\times10^{11}$ GC/kg), and above normal levels at $2.3\times10^{10}$ GC/mouse ($1.1\times10^{12}$ GC/kg).

FIG. 15. Schematic representation of pAAV2.rh10.KanR.

FIG. 22 shows FIX antigen and activity levels in animals injected with vectors carrying the hFIXco and hFIXco3T-Padua at 2 weeks post injection.

FIGS. 27A-27d are graphs showing intracellular cytokine staining (ICS) of CD4+(FIGS. 27A and 27B) and CD8+ (FIGS. 27C and 27D) peripheral blood mononuclear cells (PBMCs) in patients treated with low-dose ($1.6\times1012$ GC/kg) or mid-dose ($5.0\times1012$ GC/kg) of AAVrh10.hFIXco3T.

Figure 27A:
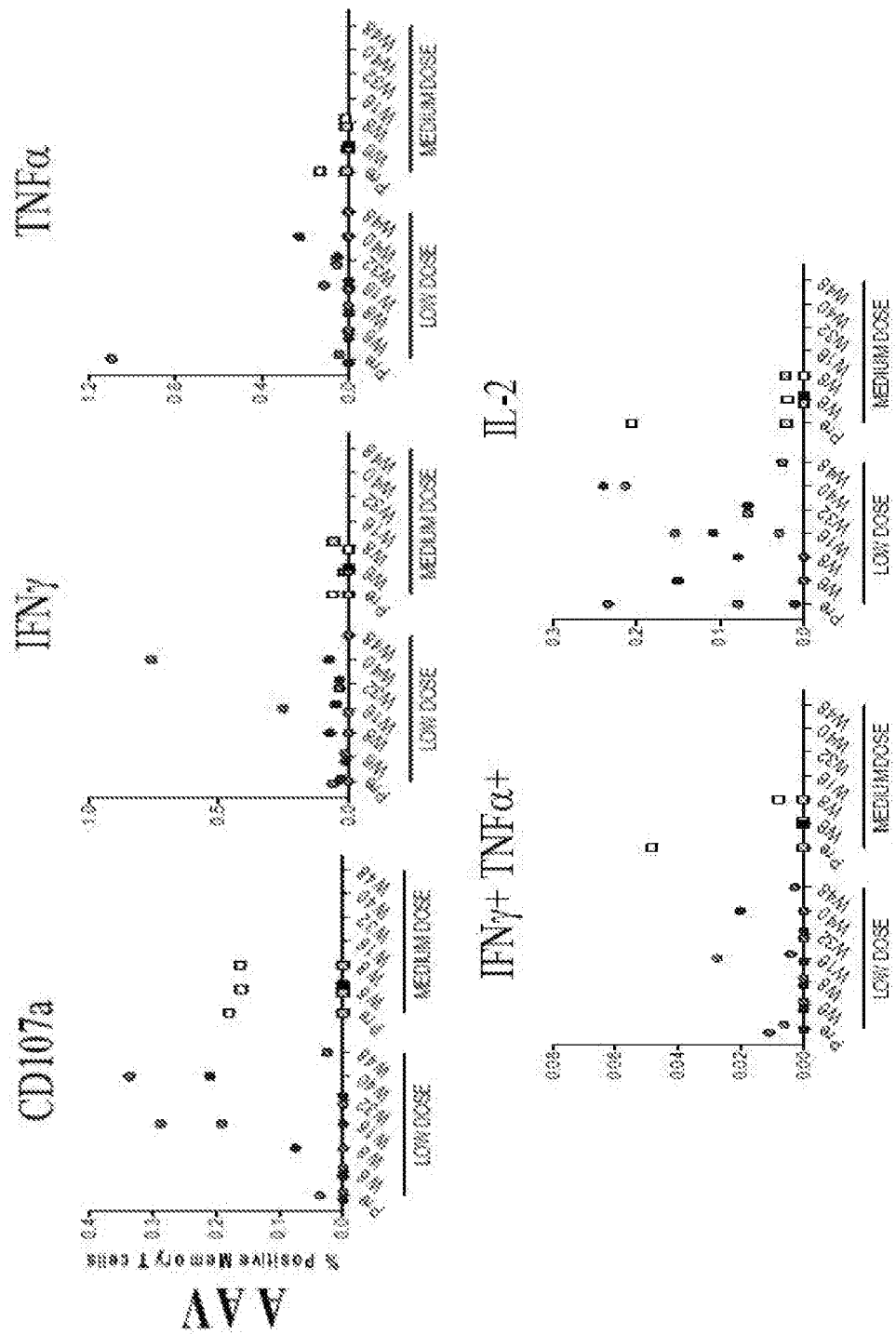

FIG. 30A shows the human FIX amino acid sequence (SEQ ID NO: 10) with the mutations of five patients receiving the low- or mid-dose of the vector discussed for FIGS. 27A and B. The mutation of one patient is not shown as it is not a coding mutation. Using prediction software, the MHC Class I binding affinity to various alleles was predicted as shown in FIG. 30B.

5. DETAILED DESCRIPTION OF THE INVENTION

This invention relates to the use of a replication deficient adeno-associated virus (AAV) to deliver a human Factor IX (hFIX) gene to liver cells of patients (human subjects) diagnosed with hemophilia B. The recombinant AAV vector (rAAV) used for delivering the hFIX gene ("rAAV.hFIX") should have a tropism for the liver (e.g., an rAAV bearing an AAVrh.10 capsid), and the hFIX transgene should be controlled by liver-specific expression control elements. In one embodiment, the expression control elements include one or more of the following: an alpha-1 microglobulin/bikunin enhancer; a thyroid hormone binding globulin promoter (TBG); a human beta globin IVS2 intron; a WPRE; and a polyA signal. Such elements are further described herein.

As used herein, "AAVrh10 capsid" refers to the AAVrh.10 capsid having the amino acid sequence of GenBank, accession: AAO88201, SEQ ID NO: 14, which is incorporated by reference herein. Some variation from this encoded sequence is envisioned, including sequences having about 99% identity to the referenced amino acid sequence in AAO88201 and US 2013/0045186A1 (i.e., less than about 1% variation from the referenced sequence), provided that the integrity of the ligand-binding site for the affinity capture purification is maintained and the change in sequences does not substantially alter the pH range for the capsid for the ion exchange resin purification. For example, studies indicate that rh.39, rh.20, rh.25, AAV10, bb.1, bb.2 and pi.2 serotypes should bind to the illustrated affinity resin column because their sequence in the antibody-binding region is identical or very similar to rh10. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

As used herein, the term "NAb titer" a measurement of how much neutralizing antibody (e.g., anti-AAV NAb) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, the term "operably linked" refers to both expression control sequences that are contiguous with the gene of interest and expression control sequences that act in trans or at a distance to control the gene of interest.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist, consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

5.1 Gene Therapy Vectors

In one aspect, a recombinant adeno-associated virus (rAAV) vector carrying the human clotting factor 9 (hFIX or hF9) gene is provided for use in gene therapy. The rAAV.hFIX vector should have a tropism for the liver (e.g., an rAAV bearing an AAVrh.10 capsid) and the hFIX transgene should be controlled by liver-specific expression control elements. The vector is formulated in a buffer/carrier suitable for infusion in human subjects. The buffer/carrier should include a component that prevents the rAAV from sticking to the infusion tubing but does not interfere with the rAAV binding activity in vivo.

5.1.1. The rAAV.hFIX Vector
5.1.1.1. The hFIX Sequence

Human coagulation factor IX FIX is a vitamin K-dependent single-chain glycoprotein, which is synthesized as a precursor protein. The precursor undergoes extensive post-translational modification to become the fully gamma-carboxylated mature zymogen that is secreted into the blood. The precursor protein has a signal peptide at the amino ($NH_2$) terminal end, which directs the protein to the endoplasmic reticulum in the liver, and a prepro leader sequence recognized by the gamma-glutamylcarboxylase, which is responsible for the posttranslational modification (carboxylation) of the glutamic acid residues (Gla) in the $NH_2$-terminal portion of the molecule. These 2 parts of the molecule are removed before the protein is secreted into the circulation. The full length protein (before cleavage) is 461 amino acids as shown in SEQ ID NO: 10 (Genbank Accession # P00740). The mature protein is about 415 amino acids.

In one embodiment, the hFIX gene encodes the hFIX protein shown in SEQ ID NO: 10, i.e., the full length protein. In another embodiment the hFIX gene encodes an hFIX protein which has a polymorphism at aa194. In on embodiment, the polymorphis is T194A.

Thus, in one embodiment, the hFIX transgene can include, but is not limited to, one or more of the sequences provided by SEQ ID NO:1, SEQ ID NO: 2, or SEQ ID NO: 13, which are provided in the attached Sequence Listing, which is incorporated by reference herein. SEQ ID NO: 1 provides the cDNA for native human FIX. SEQ ID NO: 2 provides an engineered cDNA for human FIX, which has been codon optimized for expression in humans (also called hFIXco or hFIXco3T). SEQ ID NO: 13 provides an engineered cDNA for human FIX, which has been codon optimized for expression in humans. Alternatively or additionally, web-based or commercially available computer programs, as well as service based companies may be used to back translate the amino acids sequences to nucleic acid coding sequences, including both RNA and/or cDNA. See, e.g., backtranseq by EMBOSS, www.ebi.ac.uk/Tools/st/; Gene Infinity (www.geneinfinity.org/sms-/sms_backtranslation.html); ExPasy (www.expasy.org/tools/). It is intended that all nucleic acids encoding the described hFIX polypeptide sequences are encompassed, including nucleic acid sequences which have been optimized for expression in the desired target subject (e.g., by codon optimization). In one embodiment, the nucleic acid sequence encoding hFIX shares at least 95% identity with the native hFIX coding sequence of SEQ ID NO: 1. In another embodiment, the nucleic acid sequence encoding hFIX shares at least 99%, 97%, 95%, 90%, 85%, 80%, 75%, 70%, or 65% identity with the native hFIX coding sequence of SEQ ID NO: 1. In yet another embodiment, the nucleic acid sequence encoding hFIX shares at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity with the hFIX coding sequence of SEQ ID NO: 1 or SEQ ID NO: 2. In one embodiment, the nucleic acid sequence encoding hFIX shares about 75% identity with the native hFIX coding sequence of SEQ ID NO: 1. In one embodiment, the nucleic acid sequence encoding hFIX is SEQ ID NO: 2. In one embodiment, the nucleic acid sequence encoding hFIX is SEQ ID NO: 13.

Codon-optimized coding regions can be designed by various different methods. This optimization may be performed using methods which are available on-line (e.g., GeneArt), published methods, or a company which provides codon optimizing services, e.g., as DNA2.0 (Menlo Park, Calif.). One codon optimizing approach is described, e.g., in International Patent Publication No. WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

5.1.1.2. The rAAV Vector

Because hFIX is natively expressed in the hepatocytes, it is desirable to use an AAV which shows tropism for liver. In one embodiment, the AAV supplying the capsid is AAVrh.10. However, any of a number of rAAV vectors with liver tropism can be used.

In a specific embodiment described in the Examples, infra, the gene therapy vector is an AAVrh.10 vector expressing an hFIX transgene under control of a liver-specific promoter (thyroxine-binding globulin, TBG) referred to as rAAVrh.10.TBG.hFIX or rAAVrh.10.LSP.hFIXco. The external AAV vector component is a serotype rh.10, T=1 icosahedral capsid consisting of 60 copies of three AAV viral proteins, VP1, VP2, and VP3, at a ratio of 1:1:10. The capsid contains a single-stranded DNA rAAV vector genome.

The rAAVrh.10.TBG.hFIX genome contains an hFIX expression cassette flanked by two AAV inverted terminal repeats (ITRs). The hFIX expression cassette includes an enhancer, promoter, intron, an hFIX coding sequence, a WPRE and polyadenylation (polyA) signal. These control sequences are "operably linked" to the hFIX gene sequences. The expression cassette and flanking ITRs may be engineered onto a plasmid which is used for production of a viral vector.

The ITRs are the genetic elements responsible for the replication and packaging of the genome during vector production and are the only viral cis elements required to generate rAAV. The minimal sequences required to package the expression cassette into an AAV viral particle are the AAV 5' and 3' ITRs, which may be of the same AAV origin as the capsid, or which of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the hFIX coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

Expression of the hFIX coding sequence is driven from a liver-specific promoter. An illustrative plasmid and vector described herein uses the hepatocyte-specific promoter thyroxin binding globulin (TBG). Alternatively, other liver-specific promoters may be used including the alpha 1 anti-trypsin (A1AT); human albumin (Miyatake et al., J. Virol., 71:5124 32 (1997)), humAlb; and hepatitis B virus core promoter, (Sandig et al., Gene Ther., 3:1002 9 (1996)), TTR minimal enhancer/promoter, or alpha-antitrypsin promoter. See, e.g., The Liver Specific Gene Promoter Database, Cold Spring Harbor, rulai.schl.edu/LSPD, incorporated by reference herein. Although less desired, other promoters, such as viral promoters, constitutive promoters, regulatable promoters [see, e.g., WO 2011/126808 and WO 2013/04943], or a promoter responsive to physiologic cues may be used in the vectors described herein.

In one embodiment, the expression control sequences include an enhancer. In one embodiment the alpha 1 microglobulin/bikunin enhancer element is included. In another embodiment, two copies of the alpha 1 microglobulin/bikunin enhancer element precede the TBG promoter to stimulate promoter activity. Together these elements (two copies of the APB enhancer and TBG promoter) are termed "LSP" as shown in nt 239 to nt 965 of SEQ ID NO: 11 or SEQ ID NO: 15 and FIG. 1. See, Wang et al, Sustained correction of bleeding disorder in hemophilia B mice by gene therapy, PNAS, 96:3906-10 (March 1999), which is incorporated herein by reference.

In addition to a promoter, an expression cassette and/or a vector may contain other appropriate transcription initiation, termination, enhancer sequences, and efficient RNA processing signals. Such sequences include splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. In one embodiment, a human beta globin IVS2 intron is present to further enhance expression and a bovine growth hormone (bGH) polyadenylation (polyA) signal is included to mediate termination of hFIX mRNA transcripts. Examples of other suitable polyA sequences include, e.g., SV40, rabbit beta globin, and TK polyA. Examples of other suitable enhancers include, e.g., the alpha fetoprotein enhancer, the TTR minimal promoter/enhancer, human apolipoprotein hepatic control region, amongst others.

In other embodiments, spacers are inserted in the expression cassette and/or vector. Such spacers may be included to adjust the size of the total vector genome. In one embodiment, spacers are included such that the vector genome is approximately the same size as the native AAV vector genome (e.g., between 4.1 and 4.7 kb). In one embodiment, spacers are included such that the vector genome is approximately 4.7 kb. See, Wu et al, Effect of Genome Size on AAV Vector Packaging, Mol Ther. 2010 January; 18(1): 80-86, which is incorporated herein by reference. Spacer DNA may be non-coding DNA, for example, an intron sequence.

In one embodiment, the vector is a self-complementary vector. The abbreviation "sc" refers to self-complementary. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

In one embodiment the rAAV vector genome is nt 1 to nt 3951 of SEQ ID NO: 11. In another embodiment, the rAAV vector genome is nt 7 to nt 4115 of SEQ ID NO: 12. In yet another embodiment, the rAAV vector genome is nt 1 to nt 3951 of SEQ ID NO: 16.

5.1.2. rAAV.hFIX Formulation

In one embodiment, the rAAV.hFIX vector is provided in a pharmaceutical composition which comprises an aqueous carrier, excipient, diluent or buffer. In a specific embodiment exemplified herein, the rAAV.hFIX formulation is a suspension containing an effective amount of rAAV.hFIX vector suspended in an aqueous solution containing composed of 0.001% Pluronic F-68 in TMN200 (200 mM sodium chloride, 1 mM magnesium chloride, 20 mM Tris, pH 8.0). However, various suitable solutions are known including those which include one or more of: buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration. In another embodiment, the buffer is PBS. Other suitable buffers include Ringer's solution, Elliot's solution, and others known in the art.

For example, a suspension as provided herein may contain both NaCl and KCl. The pH may be in the range of 6.5 to 8.5, or 7 to 8.5, or 7.5 to 8. A suitable surfactant, or combination of surfactants, may be selected from among a Poloxamers, i.e., nonionic triblock copolymers composed of a central hydrophobic chain of polyoxypropylene (poly (propylene oxide)) flanked by two hydrophilic chains of polyoxyethylene (poly(ethylene oxide)), SOLUTOL HS 15 (Macrogol-15 Hydroxystearatarate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension. In another embodiment, the vector is suspended in an aqueous solution containing 180 mM sodium chloride, 10 mM sodium phosphate, 0.001% Poloxamer 188, pH 7.3.

In one embodiment, the formulation is suitable for use in human subjects and is administered intravenously. In one embodiment, the formulation is delivered via a peripheral vein by bolus injection. In one embodiment, the formulation is delivered via a peripheral vein by infusion over about 10 minutes (+5 minutes). In one embodiment, the formulation is delivered via a peripheral vein by infusion over about 60 minutes (±5 minutes). However, these times may be adjusted as needed or desired. Any suitable method or route can be used to administer an AAV-containing composition as described herein, and optionally, to co-administer other active drugs or therapies in conjunction with the AAV-mediated antibodies described herein. Routes of administration include, for example, systemic, oral, inhalation, intranasal, intratracheal, intraarterial, intraocular, intravenous, intramuscular, subcutaneous, intradermal, and other parental routes of administration.

In one embodiment, the formulation may contain, e.g., about $1.5 \times 10^{11}$ genome copies per kilogram of patient body weight (GC/kg) to about $3 \times 10^{13}$ GC/kg, about $1.6 \times 10^{10}$ to about $5 \times 10^{10}$ GC/kg, about $5 \times 10^{11}$ genome copies per kilogram of patient body weight (GC/kg) to about $2 \times 10^{13}$ GC/kg, or about $1 \times 10^{12}$ to about $1.25 \times 10^{13}$ GC/kg, as measured by oqPCR or digital droplet PCR (ddPCR) as described in, e.g., M. Lock et al, Hu Gene Therapy Methods, Hum Gene Ther Methods. 2014 April; 25(2): 115-25. doi: 10.1089/hgtb.2013.131. Epub 2014 Feb. 14, which is incorporated herein by reference. In one embodiment, the rAAV.hFIX formulation is a suspension containing at least $1 \times 10^{13}$ genome copies (GC)/mL, or greater, as measured by oqPCR or digital droplet PCR (ddPCR) as described in, e.g., M. Lock et al, supra.

In order to ensure that empty capsids are removed from the dose of AAV.hFIX that is administered to patients, empty capsids are separated from vector particles during the vector purification process, e.g., using the method discussed herein. In one embodiment, the vector particles containing packaged genomes are purified from empty capsids using the process described in U.S. Patent Application No. 62/322, 055, filed on Apr. 13, 2016, and entitled "Scalable Purification Method for AAVrh.10", which is incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates. Other purification methods are described, e.g., in U.S. Patent Application Nos. 62/266,347, 62/266,357, 62/322,071, 62/266,351, 62/322,083, 62/266,341, and 62/322,098, each of which is incorporated herein by reference.

While any conventional manufacturing process can be utilized, the process described herein (and in U.S. Patent Application No. 62/322,055) yields vector preparations wherein between 50 and 70% of the particles have a vector genome, i.e., 50 to 70% full particles. Thus for an exemplary dose of $5 \times 10^{11}$ GC/kg body weight, the total particle dose is between $7 \times 10^{11}$ GC and $1 \times 10^{12}$ GC. On the basis of peer-reviewed and published data, it can be estimated that the total particle titer in starting dose in the clinical trial described in Nathwani et al (Nathwani, Amit C., et al. "Adenovirus-associated virus vector—mediated gene transfer in hemophilia B." N Engl J Med 2011.365 (2011): and 2357-2365; Nathwani, Amit C., et al. "Long-term safety and efficacy of factor IX gene therapy in hemophilia B." New England Journal of Medicine 371.21 (2014): 1994-2004.) was approximately $2 \times 10^{12}$ total particles. In another embodiment, the dosage is one half log higher than the first dose, or $1.6 \times 10^{12}$ GC/kg body weight, and the total particle dose is between $2.3 \times 10^{12}$ and $3 \times 10^{12}$ particles. In another embodiment, the proposed dose is one half log higher than the second dose, or $5 \times 10^{12}$ GC/kg body weight, and the total particle dose is between $7.6 \times 10^{12}$ and $1.1 \times 10^{13}$ particles. This total particle dose is well below the estimated total particle dose in the Nathwani trial that provoked a rise in ALT [Nathwani, Amit C., et al. "Adenovirus-associated virus vector-mediated gene transfer in hemophilia B." N Engl J Med 2011.365 (2011): 2357-2365; and Nathwani, Amit C., et al. "Long-term safety and efficacy of factor IX gene therapy in hemophilia B." New England Journal of Medicine 371.21 (2014): 1994-2004.]. In one embodiment, the formulation is characterized by an rAAV stock having a ratio of "empty" to "fill" of 1 or less, less than 0.75, less than 0.5, or less than 0.3.

Briefly, in one embodiment, a method for separating AAVrh10 viral particles from AAVrh10 capsid intermediates is provided which involves: subjecting a mixture comprising recombinant AAVrh10 viral particles and AAV rh10 capsid intermediates to fast performance liquid chromatography, wherein the AAVrh10 viral particles and AAVrh10 intermediates are bound to an anion exchange resin equilibrated at a pH of about 10.0 and subjected to a salt gradient while monitoring eluate for ultraviolet absorbance at about 260 and about 280, wherein the AAVrh10 full capsids are collected from a fraction which is eluted when the ratio of A260/A280 reaches an inflection point.

In one embodiment, the method further includes (a) mixing a suspension comprising recombinant AAVrh10 viral particles and AAV rh10 capsid intermediates and a Buffer A comprising 20 mM to 50 mM Bis-Tris propane (BTP) and a pH of about 10.0; (b) loading the suspension of (a) onto a strong anion exchange resin column; (c) washing the loaded anion exchange resin with Buffer 1% B which comprises a salt having the ionic strength of 10 mM to 40 mM NaCl and BTP with a pH of about 10.0; (d) applying an increasing salt concentration gradient to the loaded and washed anion exchange resin, wherein the salt gradient is the equivalent of about 10 mM to about 40 mM NaCl; and (e) collecting rAAVrh10 particles from elute obtained at a salt concentration equivalent to at least 70 mM NaCl, where the rAAVrh10 particles are at least about 90% purified from AAVrh10 intermediates. In one embodiment, this is determined by genome copies.

In one embodiment, the intermediates are eluted from the anion exchange resin when the salt concentration is the equivalent of greater than about 50 mM NaCl. In still a further embodiment. Buffer A is further admixed with NaCl to a final concentration of IM in order to form or prepare Buffer B. In yet another embodiment, the salt gradient has an ionic strength equivalent to 10 mM to about 190 mM NaCl. The elution gradient may be from 1% buffer B to about 19% Buffer B. Optionally, the vessel containing the anion exchange resin is a monolith column and where Buffer A, Buffer B, and the salt gradient are in about 60 column volumes.

A stock or preparation of rAAVrh.10 particles (packaged genomes) is "substantially free" of AAV empty capsids (and other intermediates) when the rAAVrh.10 particles in the stock are at least about 75% to about 100%, at least about 80%, at least about 85%, at least about 90%, at least about 95%, or at least 99% of the rAAVrh.10 in the stock and "empty capsids" are less than about 1%, less than about 5%, less than about 10%, less than about 15% of the rAAVrh.10 in the stock or preparation.

In a further embodiment, the average yield of rAAV particles is at least about 70%. This may be calculated by determining titer (genome copies) in the mixture loaded onto the column and the amount presence in the final elutions. Further, these may be determined based on q-PCR analysis and/or SDS-PAGE techniques such as those described herein or those which have been described in the art.

For example, to calculate empty and full particle content, VP3 band volumes for a selected sample (e.g., an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., *Gene Therapy* (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes. Anti-AAV capsid antibodies are then used as the primary antibodies that bind to denatured capsid proteins, for example an anti-AAV capsid monoclonal antibody, such as the B anti-AAV-2 monoclonal antibody (Wobus et al., J. Virol. (2000) 74:9281-9293) A secondary antibody is then used, one that binds to the primary antibody and contains a means for detecting binding with the primary antibody for example an anti-IgG antibody containing a detection molecule covalently bound to it, such as a sheep anti-mouse IgG antibody covalently linked to horseradish peroxidase. A method for detecting binding is used to semi-quantitatively determine binding between the primary and secondary antibodies, for example a detection method capable of detecting radioactive isotope emissions, electromagnetic radiation or colorimetric changes, such as a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System, Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, beat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alliteratively, droplet digital PCR (ddPCR) may be used. For example, methods for determining single-stranded and self-complementary AAV vector genome titers by ddPCR have been described. See, e.g., M. Lock et a. Hu Gene Therapy Methods, Hum Gene Ther Methods. 2014 April; 25(2):115-25, doi: 10.1089/hgtb.2013.131. Epub 2014 Feb. 14.

5.1.3 Manufacturing

Figure 12:
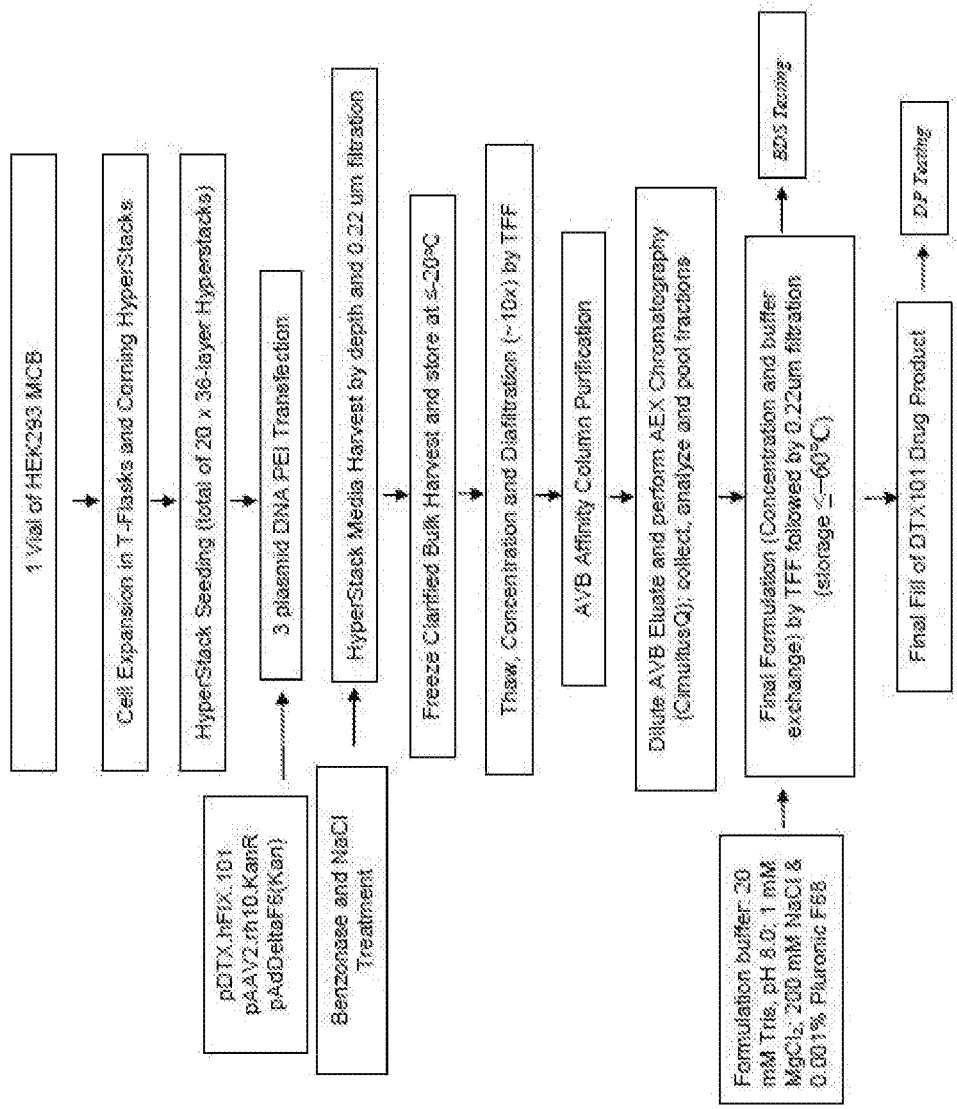
Figure 13:
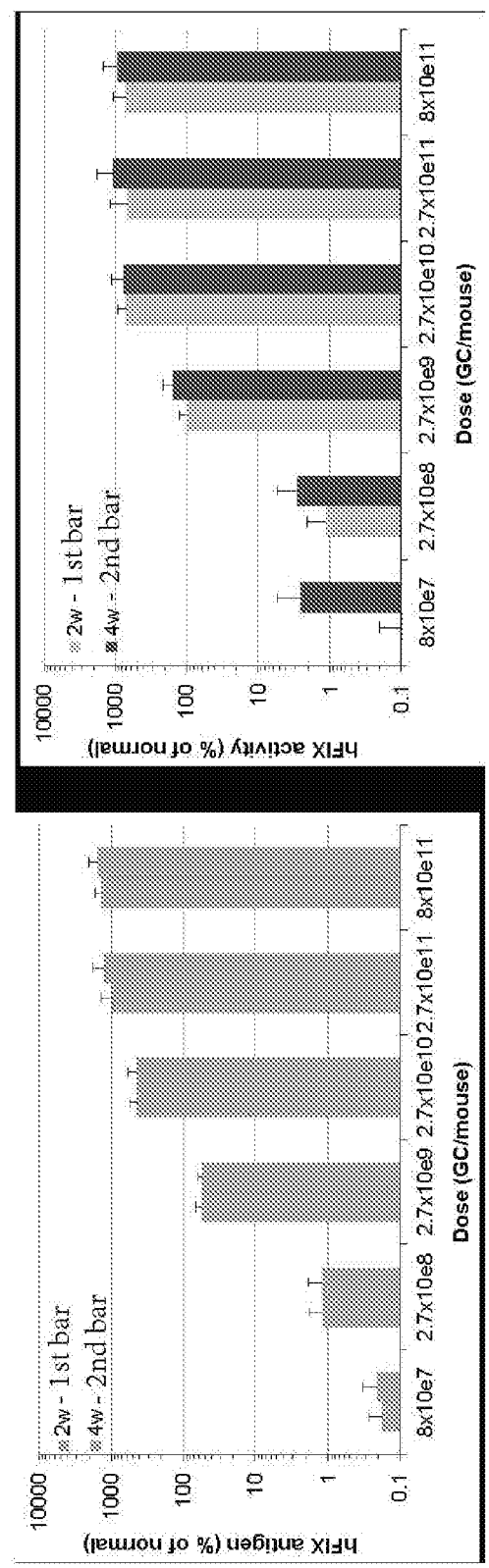

The rAAV.hFIX vector can be manufactured as shown in the flow diagram shown in FIG. 12. Briefly, cells (e.g. HEK 293 cells or HeLa cells) are propagated in a suitable cell culture system and transfected for vector generation. The rAAV.hFIX vector can then be harvested, concentrated and purified to prepare bulk vector which is then filled and finished in a downstream process.

Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest.

In one embodiment, the production plasmid is that shown in SEQ ID NO: 11. In another embodiment, the production plasmid is that shown in SEQ ID NO: 12. In yet another embodiment, the production plasmid is that shown in SEQ ID NO: 16.

The crude cell harvest may thereafter be subject method steps such as concentration of the vector harvest, diafiltration of the vector harvest, microfluidization of the vector harvest, nuclease digestion of the vector harvest, filtration of microfluidized intermediate, purification by chromatography, purification by ultracentrifugation, buffer exchange by tangential flow filtration, and formulation and filtration to prepare bulk vector.

In a specific embodiment, the methods used for manufacturing the gene therapy vectors are described in Example 3 at Section 7, infra.

5.2 Patient Population

Severe hemophilia B patients are the chosen study population for several reasons. Severe hemophilia B patients are defined as having less than 1% of normal Factor IX (FIX) activity thus requiring frequent infusions of FIX to control their bleeding diathesis. This represents a significant burden with respect to carrying on a normal life and in addition, the blood levels of FIX go through the well-known peaks and troughs pattern, which is not optimal. The fact that FIX blood levels in severe patients is less than 1% makes it possible to reliably measure even low to moderate increases in FIX blood levels after AAVrh.10.hFIX has been administered. Recent clinical trials have borne out the validity of this approach.

Patients who are candidates for treatment include adult males ≥0.18 years of age, diagnosed with moderate/severe or severe hemophilia B. In one embodiment, the patient has a baseline FIX activity ≤2% of normal or documented history of FIX activity ≤2%. In some embodiments, a patient <18 years of age can be treated. Candidates for treatment include subjects who have had at least 3 bleeding episodes per year that require on-demand treatment with FIX. Other candidates for treatment include subjects who are treated with a prophylactic regimen of FIX. Other criteria demonstrating that the subject is appropriate for treatment includes at least 100 days exposure history to FIX; no documented history of inhibitors (neutralizing antibodies) to exogenous FIX; no known allergic reaction to exogenous FIX or any component of rAAVrh.10.LSP.hFIXco.

Prior to treatment, the hemophilia B patient should be assessed for NAb to the AAV serotype used to deliver the hFIX gene (e.g, AAVrh.10). Such NAbs can interfere with transduction efficiency and reduce therapeutic efficacy.

Hemophilia B patients that have a baseline serum NAb titer ≤1:5 are good candidates for treatment with the rAAV.hFIX gene therapy protocol. Treatment of Hemophilia B patients with titers of serum NAb >1:5 may require a combination therapy, such as plasmapheresis. Alternative, empty capsids may be added to the final vector formulation. See, Mingozzi F et al, 2013. PMID 23863832, which is incorporated herein by reference. Further, transient co-treatment with an immunosuppressant may be required to combat T cell response to the capsid or transgene product. Immunosuppressants for such co-therapy include, but are not limited to, steroids, antimetabolites, T-cell inhibitors, and alkylating agents. For example, such transient treatment may include a steroid (e.g., prednisole) dosed once daily for 7 days at a decreasing dose, in an amount starting at about 60 mg, and decreasing by 10 mg/day (day 7 no dose). Other doses and medications may be selected.

Subjects may be permitted to continue their standard of care treatment(s) (e.g., recombinant FIX therapy) prior to and concurrently with the gene therapy treatment at the discretion of their caring physician. In the alternative, the physician may choose to stop standard of care therapies prior to administering the gene therapy treatment and, optionally, resume standard of care treatments as a co-therapy after administration of the gene therapy.

Desirable endpoints of the gene therapy regimen are an increase in FIX activity to 5% of normal from baseline up to 1 year, 5 years, 10 years or longer after administration of the gene therapy treatment. In one embodiment, patients achieve desired circulating FIX levels (e.g., 5% or greater) after treatment with AAVrh.10.hFIX, alone without the use of adjunctive treatments over the duration of the study, or over a period of time during the study. In another embodiment, patients achieve circulating FIX levels of 10%, 15%, 20% or greater after treatment with AAVrh.10.hFIX, alone without the use of adjunctive treatments over the duration of the study or over a period of time during the study.

Nevertheless, patients having one or more of the following characteristics may be excluded from treatment at the discretion of their caring physician:

1. History of significant liver disease (ie; portal hypertension).
2. Significant hepatic inflammation or cirrhosis.
3. Evidence of active hepatitis B virus (HBV) or hepatitis C virus (HCV) infection.
4. History of human immunodeficiency virus (HIV) infection AND any of the following: CD4+ cell count <350 cells/mm$^3$, change in antiretroviral therapy regimen within 6 months prior to Day 0, or plasma viral load >200 copies/ml, on 2 separate occasions, as measured by PCR.
5. Anti-AAVrh10 neutralizing antibody titer >1:5.
6. Participation (current or previous) in another gene therapy study.
7. Participation in another investigational medicine study within 3 months before screening.

In other embodiments, a caring physician may determine that the presence of one or more of these physical characteristics (medical history) should not preclude treatment as provided herein.

5.3. Dosing & Route of Administration

In another embodiment, provided herein is a method of treating a patient having hemophilia B with an rAAV as described herein. In one embodiment, about $1\times10^{11}$ to about $1\times10^{13}$ genome copies (GC) of the rAAV/kg patient body weight are delivered the patient in an aqueous suspension. All ranges described herein are inclusive of the endpoints.

In one embodiment, the rAAV.hFIX vector is delivered as a single dose per patient. In one embodiment, the subject is delivered the minimal effective dose (MED) (as determined by preclinical study described in the Examples herein). As used herein, MED refers to the rAAV.hFIX dose required to achieve 5% of normal Factor IX activity.

As is conventional, the vector titer is determined on the basis of the DNA content of the vector preparation. In one embodiment, quantitative PCR or optimized quantitative PCR as described in the Examples is used to determine the DNA content of the rAAV.hFIX vector preparations. In one embodiment, digital droplet PCR as described in the Examples is used to determine the DNA content of the rAAV.hFIX vector preparations. In one embodiment, the dosage is about $1\times10^{11}$ genome copies (GC)/kg body weight to about $1\times10^{13}$ GC/kg, inclusive of endpoints. In one embodiment, the dosage is $5\times10^{11}$ GC/kg. In another embodiment, the dosage is $5\times10^{12}$ GC/kg. In specific embodiments, the dose of rAAV.hFIX administered to a patient is at least $5\times10^{11}$ GC/kg, $1\times10^{12}$ GC/kg, $1.5\times10^{12}$ GC/kg, $2.0\times10^{12}$ GC/kg, $2.5\times10^{12}$ GC/kg, $3.0\times10^{12}$ GC/kg, $3.5\times10^{12}$ GC/kg, $4.0\times10^{12}$ GC/kg, $4.5\times10^{12}$ GC/kg, $5.0\times10^{12}$ GC/g, $5.5\times10^{12}$ GC/kg, $6.0\times10^{12}$ GC/kg, $6.5\times10^{12}$ GC/kg, $7.0\times10^{12}$ GC/kg, or $7.5\times10^{12}$ GC/kg. Also, the replication-defective virus compositions can be formulated in dosage units to contain an amount of replication-defective virus that is in the range of about $1.0\times10^9$ GC to about $1.0\times10^{15}$ GC. As used herein, the term "dosage" can refer to the total dosage delivered to the subject in the course of treatment, or the amount delivered in a single (of multiple) administration.

In another embodiment, the composition is readministered at a later date. Optionally, more than one readministration is permitted. Such readministration may be with the same type of vector or a different viral vector as described herein. In one embodiment, the vector is readministered about 6 months after the first administration. In another embodiment, the vector is readministered about 1 year after the first administration. In another embodiment, the vector is readministered about 2 years after the first administration. In another embodiment, the vector is readministered about 3 years after the first administration. In another embodiment, the vector is readministered about 4 years after the first administration. In another embodiment, the vector is readministered about 5 years after the first administration. In another embodiment, the vector is readministered about 6 years after the first administration. In another embodiment, the vector is readministered about 7 years after the first administration. In another embodiment, the vector is readministered about 8 years after the first administration. In another embodiment, the vector is readministered about 9 years after the first administration. In another embodiment, the vector is readministered about 10 years or more after the first administration.

In one embodiment, the dosage is sufficient to increase the Factor IX levels in the patient to 5% of normal. In another embodiment, the dosage is sufficient to increase the Factor IX levels in the patient to 10% of normal. In another embodiment, the dosage is sufficient to increase the Factor IX levels in the patient to 15% of normal. In another embodiment, the dosage is sufficient to increase the Factor IX levels in the patient to 20% or greater of normal. In another embodiment, the dosage is sufficient to increase the Factor IX levels in the patient to 25% or greater of normal. In another embodiment, the dosage is sufficient to increase the Factor IX levels in the patient to 30, 35, 40, 45, 50, 55, 60, 65, 70, 75, 80, 85, 90, 95%/o or greater of normal.

In some embodiments, rAAV.hFIX is administered in combination with one or more therapies for the treatment of hemophilia B, such as administration of recombinant FIX. In another embodiment, rAAV.hFIX is administered as a combination product with vectors having different AAV capsids. In one embodiment, the combination product includes an rAAVrh.10.hFIX vector and an rAAV3B.hFIX vector.

5.4. Measuring Clinical Objectives

Measurements of efficacy of treatment can be measured by transgene expression and activity as determined by plasma Factor IX levels and Factor IX activity. Further assessment of efficacy can be determined by clinical assessment of replacement Factor IX requirements and frequency of spontaneous bleeding episodes. Such assessments may be conducted twice a week for 4 weeks after the administration of the product, weekly from week 6 to week 12, monthly throughout the remainder of the first year and at 6 month intervals for a total period of 5 years.

Safety of the gene therapy vector after administration can be assessed by the number of adverse events, changes noted on physical examination, and/or clinical laboratory parameters assessed at multiple time points up to about 52 weeks post vector administration. Although physiological effect may be observed earlier, e.g., in about one week, in one embodiment, steady state levels expression levels are reached by about 4 to about 8 weeks. The following assessments may be conducted twice a week for 4 weeks after the administration of the product, weekly from week 6 to week 12, monthly throughout the remainder of the first year and at 6 month intervals for a total period of 5 years. Such assessments include:

a. Physical examination
b. ECG
c. Biochemical assessment: Serum electrolytes, BUN, creatinine, calcium, phosphate, total protein, albumin, LDH, CPK, AST, ALT, alkaline phosphatase, bilirubin
d. Hematological assessment: CBC and differential, coagulation profile
e. Urinalysis
f. Immunological assessment:
g. Serological response to rh 10 capsid and to Factor IX
h. T cell response to rh 10 capsid and Factor IX antigens
i. Assessment of vector DNA; qPCR measurements in plasma, urine and saliva.

hFIX increase achieved with rAAV.hFIX administration can be assessed as a defined percent change in hFIX at about 4 to about 8 weeks, or at other desired timepoints, compared to hFIX levels of a patient not having hemophilia B, i.e., so-called normal hFIX levels, i.e., 100%. In another embodiment, the change is compared to the patient's baseline hFIX levels.

In one embodiment, the desired efficacy is an increase in the Factor IX levels in the patient to 5% of normal. In another embodiment, the dosage is sufficient to increase the Factor IX levels in the patient to 10% of normal. In another embodiment, the dosage is sufficient to increase the Factor IX levels in the patient to 15% of normal. In another embodiment, the dosage is sufficient to increase the Factor IX levels in the patient to 20% or greater of normal.

As used herein, the rAAV.hFIX vector herein "functionally replaces" or "functionally supplements" the patients defective FIX with active FIX when the patient expresses a sufficient level of FIX to achieve at least one of these clinical endpoints. Expression levels of hFIX which achieve as low as about 5% to less than 100% of normal wild-type clinical endpoint levels in a non-hemophilia patient may provide functional replacement. Alternatively, levels of hFIX which achieve as low as about 5% to less than 100% of normal wild-type function patient may provide functional replacement. In one embodiment, FIX activity is measured via APTT.

In one embodiment, expression may be observed as early as about 8 hours to about 24 hours post-dosing. One or more of the desired clinical effects described above may be observed within several days to several weeks post-dosing.

Long term (up to 260 weeks) safety and efficacy can be assessed after rAAV.hFIX administration.

In one aspect, a regimen for delivery of a hFIX gene product to a human patient is provided. The regimen comprises (a) delivery of a first rAAV.hFIX vector comprising an expression cassette as described herein; and (b) delivery of a second rAAV.hFIX vector comprising an expression cassette as described herein, wherein the first recombinant AAV vector or the second AAV vector has an AAV3B capsid. In one embodiment, the other of the first or the second AAV vector has an rh.10 capsid. Such regimens are described in International Patent Application No. PCT/US 16/42472, which is incorporated herein by reference.

In one embodiment, a second administration of a rAAV.hFIX vector is given. In one embodiment, the rAAV.hFIX vector of the second administration has the same AAV capsid as provided with the first dosage. In one embodiment, the rAAV.hFIX vector of the second administration has an AAVrh.10 capsid. In another embodiment, the rAAV.hFIX vector of the second administration has a different AAV capsid as the vector of the first dose. In one embodiment, the rAAV.hFIX vector of the second administration has a tropism for liver. In one embodiment, the rAAV.hFIX vector of the second administration has an AAV3B capsid.

In a further aspect, the invention involves targeting hepatocytes of the patient.

In one aspect, the delivery of the first rAAV and the second rAAV are temporally separated by at least about one month, at least about three months, or about 1 year to about 10 years.

The viral vectors described herein may be used in preparing a medicament for delivering hFIX to a subject (e.g., a human patient) in need thereof, supplying functional hFIX to a subject, and/or for treating hemophilia B disease.

In another aspect, an rAAV.hFIX vector as described herein is provided for use in treating hemophilia B. In another aspect, a combination product as described herein (e.g., an rAAVrh.10.hFIX vector and n rAAV3B.hFIX vector) is provided herein for use in treating hemophilia B. In another aspect, an rAAV.hFIX vector as described herein is provided for the manufacture of a medicament for treating hemophilia B. In another aspect, a combination product as described herein (e.g., an rAAVrh.10.hFIX vector and an rAAV3B.hFIX vector) is provided herein for the manufacture of a medicament for treating hemophilia B.

The following examples are illustrative only and are not intended to limit the present invention.

Examples

6. EXAMPLE 1: PROTOCOL FOR TREATING HUMAN SUBJECTS

This Example relates to a gene therapy treatment for patients with genetically confirmed X-linked hemophilia B due to mutations in the clotting factor 9 (FIX) gene. In this example, the gene therapy vector, AAVrh.10.LSP.hFIX, a replication deficient adeno-associated viral vector rh.10 (AAVrh.10) expressing hFIX is administered to patients with hemophilia B. Efficacy of treatment can be assessed using FIX levels as a surrogate for transgene expression. Primary efficacy assessments include FIX levels during the first 12 weeks post treatment, with persistence of effect followed thereafter for at least 1 year. Long term safety and persistence of transgene expression may be measured post-treatment in plasma samples.

6.1. Gene Therapy Vector

Figure 1:
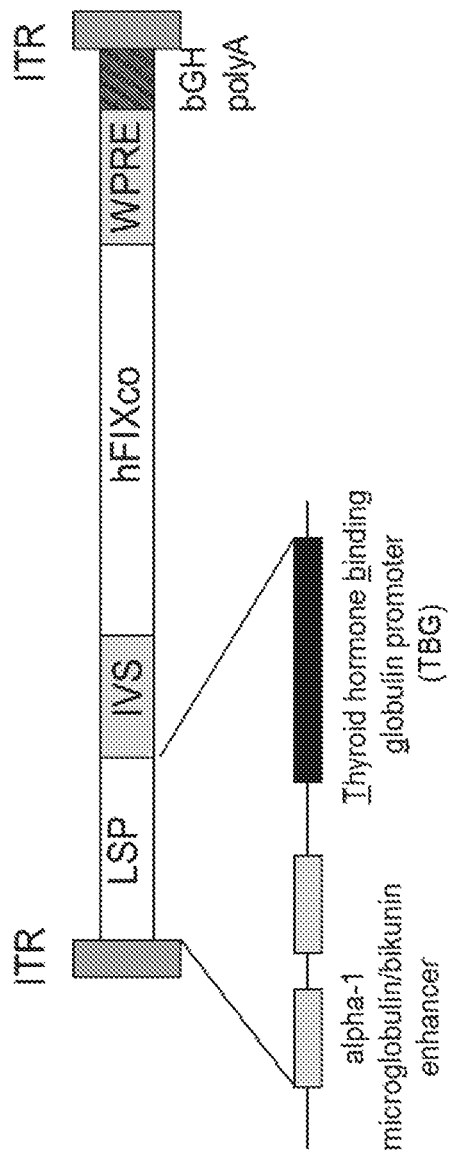

The AAVrh.10.LSP.hFIXco vector consists of the AAV vector active ingredient and a formulation buffer. The external AAV vector component is a serotype rh.10, T=1 icosahedral capsid consisting of 60 copies of three AAV viral proteins, VP1, VP2, and VP3, at a predicted ratio of 1:1:10. The capsid contains a single-stranded DNA recombinant AAV (rAAV) vector genome (FIG. 1).

The genome contains a human factor IX (FIX) transgene flanked by the two AAV inverted terminal repeats (ITRs). The transgene expression cassette comprises an enhancer, promoter, intron, the codon optimized human factor IX (hFIX) coding sequence (SEQ ID NO: 2), and polyadenylation (polyA) signal. The ITRs are the genetic elements responsible for the replication and packaging of the genome during vector production and are the only viral cis elements required to generate rAAV. Expression of the human FIX coding sequence is driven from the hepatocyte-specific thyroxine-binding globulin (TBG) promoter. Two copies of the alpha 1 microglobulin/bikunin (APB) enhancer element precede the TBG promoter to stimulate promoter activity. Together these elements (two copies of the APB enhancer and TBG promoter) are termed "LSP" as shown in FIG. 1. See, Wang et al, Sustained correction of bleeding disorder in hemophilia B mice by gene therapy, PNAS, 96:3906-10 (March 1999), which is incorporated herein by reference. A human beta globin IVS2 intron and Woodchuck hepatitis virus posttranscriptional regulatory element (WPRE) are present to further enhance expression and a bovine growth hormone polyA signal is included to mediate termination of human FIX mRNA transcripts. The vector is supplied as a suspension of AAVrh.10.TBG.hFIX vector in formulation buffer. The formulation buffer is 0.001% Pluronic F-68 in TMN200 (200 mM sodium chloride, 1 mM magnesium chloride, 20 mM Tris, pH 8.0).

Details of the vector manufacturing and characterization of the vectors, are described in the sections below.

6.2. Patient Population

Severe hemophilia B patients are the chosen study population for several reasons. Severe hemophilia B patients are defined as having less than 1% of normal Factor IX (FIX) activity thus requiring frequent infusions of FIX to control their bleeding diathesis. This represents a significant burden with respect to carrying on a normal life and in addition, the blood levels of FIX go through the well-known peaks and troughs pattern, which is not optimal. The fact that FIX blood levels in severe patients is less than 1% makes it possible to reliably measure even low to moderate increases in FIX blood levels after AAVrh.10/hFIX has been administered. Recent clinical trials have borne out the validity of this approach.

In one embodiment, the patient has one of the mutations identified in the hFIX sequence shown in FIG. 30A. In another embodiment, the patient has two of the mutations identified in the hFIX sequence shown in FIG. 30A. In another embodiment, the patient has three or more of the mutations identified in the hFIX sequence shown in FIG. 30A.

Patients who are candidates for treatment include adult males ≥18 years of age, diagnosed with moderate/severe or severe hemophilia B. In one embodiment, the patient has a baseline FIX activity ≤2% of normal or documented history of FIX activity ≤2%. In some embodiments, a patient <18 years of age can be treated. Candidates for treatment include subjects who have had at least 3 bleeding episodes per year that require on-demand treatment with FIX. Other candidates for treatment include subjects who are treated with a prophylactic regimen of FIX. Other criteria demonstrating that the subject is appropriate for treatment includes At least 100 days exposure history to FIX; no documented history of inhibitors (neutralizing antibodies) to exogenous FIX; no known allergic reaction to exogenous FIX or any component of rAAVrh.10.LSP.hFIXco.

Patients that are treated can have a baseline serum AAVrh.10 neutralizing antibody (NAb) titer ≤1:5. Subjects may be permitted to continue their standard of care treatment(s) (e.g., recombinant FIX) prior to and concurrently with the gene therapy treatment at the discretion of their caring physician. In the alternative, the physician may prefer to stop standard of care therapies prior to administering the gene therapy treatment and, optionally, resume standard of care treatments as a co-therapy after administration of the gene therapy. Desirable endpoints of the gene therapy regimen are sustained FIX activity levels >5% of normal after administration of the gene therapy treatment.

6.3. Dosing & Route of Administration

Patients receive a single dose of AAVrh.10. LSP.hFIX administered via a peripheral vein by infusion. Injection may be a bolus, or infusion over about 10 or about 60 minutes. The dose of AAVrh.10.LSP.hFIX administered to a patient is about $5 \times 10^{11}$ GC/kg or $1.6 \times 10^{12}$ GC/kg or $5 \times 10^{12}$ GC/kg. In order to ensure that empty capsids are removed from the dose of AAVrh.10.LSP.hFIX that is administered to patients, empty capsids are separated from vector particles by cesium chloride gradient ultracentrifugation or by ion exchange chromatography during the vector purification process, as discussed above.

6.4. Measuring Clinical Objectives

Primary assessments are for safety of the administered product. The following assessments are conducted twice a week for 4 weeks after the administration of the product, weekly from week 6 to week 12, monthly throughout the remainder of the first year and at 6 month intervals for a total period of 5 years.

a. Physical examination b. ECG c. Biochemical assessment: Serum electrolytes, BUN, creatinine, calcium, phosphate, total protein, albumin, LDH, CPK, AST, ALT, alkaline phosphatase, bilirubin d. Hematological assessment: CBC and differential, coagulation profile e. Urinalysis f. Immunological assessment:

g. Serological response to rh 10 capsid and to Factor IX h. T cell response to rh 10 capsid and Factor IX antigens i. Assessment of vector DNA; qPCR measurements in plasma, urine and saliva Secondary assessments are based on measurements of transgene expression and activity as determined by a. Plasma Factor IX levels and Factor IX activity b. Clinical assessment of replacement Factor IX requirements and frequency of spontaneous bleeding episodes

7. EXAMPLE 2: MANUFACTURE OF AAVRH.10.LSP.HFIX

7.1. Plasmids Used to Produce AAVrh.10.LSP.hFIX

AAVrh.10.LSP.hFIX is produced by 3 plasmid DNA transfection of human HEK 293 MCB cells with:

(i) the pDTX.hFIX.101 vector plasmid described in Section 7.2.1

(ii) an AAV helper plasmid termed pAAV2.rh10.KanR containing the AAV rep2 and cap rh10 wild-type genes described in Section 7.2.2 and (iii) a helper adenovirus plasmid termed pAdDeltaF6 (Kan) described in Section 7.2.3.

Figure 2:
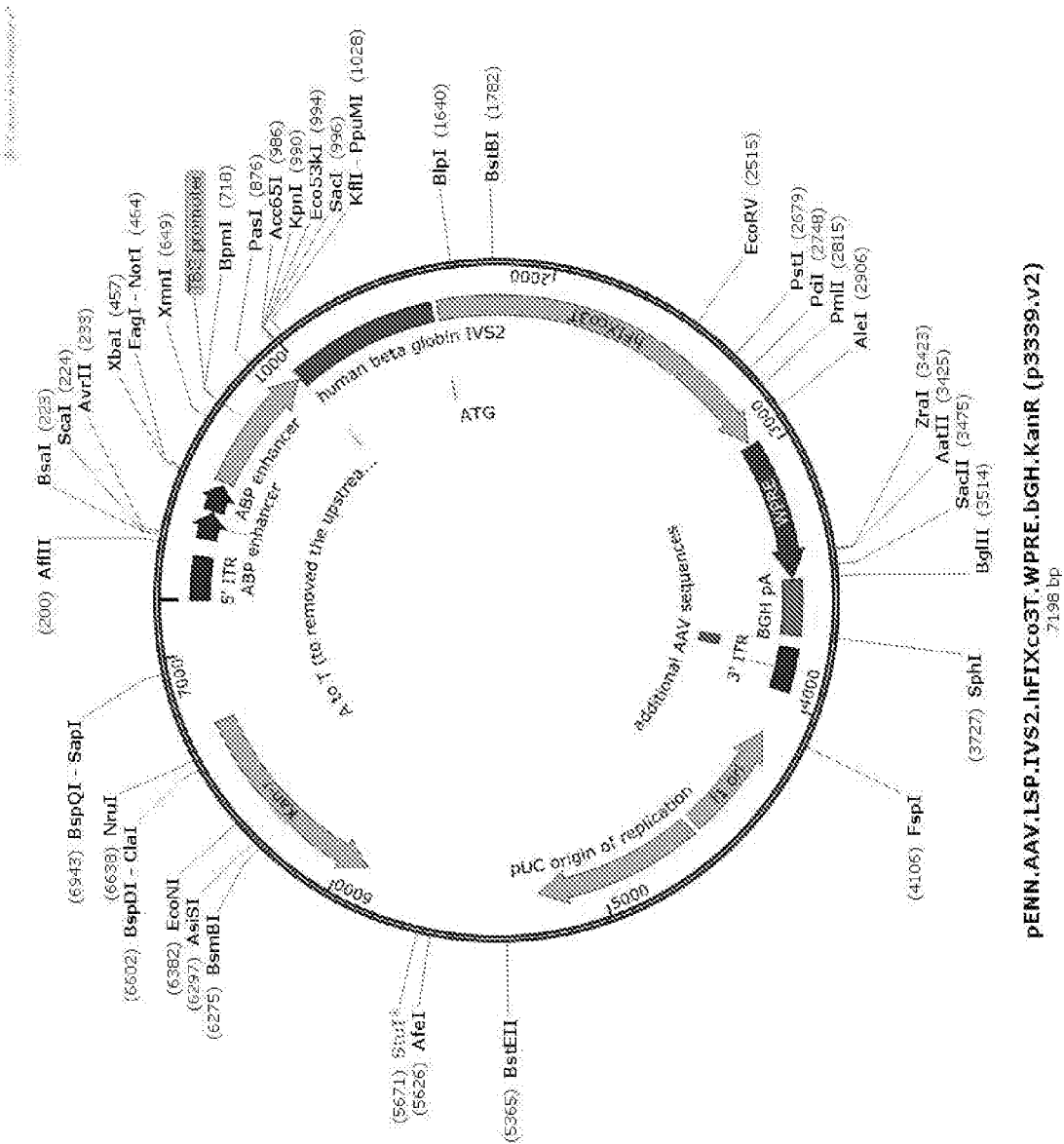

7.2.1 Cis Plasmid (Vector Genome Expression Construct):

pENN.AAV.LSP.hFIXco3T.WPRE.bGH.KanR contained the human FIX expression cassette (FIG. 2; SEQ ID NO: 11. A plasmid including an alternate FIX sequence of SEQ ID NO: 13 is shown in SEQ ID NO: 12.). A codon optimized sequence of the hFIX-Padua amino acid sequence is shown in SEQ ID NO: 17. This plasmid encoded the rAAV vector genome. The polyA signal for the expression cassette was from the bovine growth hormone gene. The plasmid contained a liver-specific promoter which consists of two repeats of alpha-1 microglobulin/bikunin enhancer followed by thyroid hormone binding globulin promoter (TBG). In addition, the plasmid contained the WPRE, described above.

To generate the cis plasmid used for production of AAVrh.10.SLP.hFIX, the human FIX codon optimized cDNA was cloned into an AAV2 ITR-flanked construct. Expression of the human FIXco cDNA was driven from the TBG promoter with a human beta globin IVS2 intron. The polyA signal for the expression cassette was from the bovine growth hormone. Two copies of the alpha 1 microglobulin/bikunin enhancer element preceded the TBG promoter.

Description of the Sequence Elements

1. Inverted terminal repeats (ITR): AAV ITRs are sequences that are identical on both ends, but found in opposite orientation. The AAV2 (GenBank #NC001401) ITR sequences function as both the origin of vector DNA replication and the packaging signal for the vector genome, when AAV and adenovirus (ad) helper functions are provided in trans. As such, the ITR sequences represent the only cis acting sequences required for vector genome replication and packaging. The 5' ITR sequence used in the exemplified vector is shown in SEQ ID NO: 3. The 3' ITR sequence used in the exemplified vector is shown in SEQ ID NO: 9.

Figure 5:
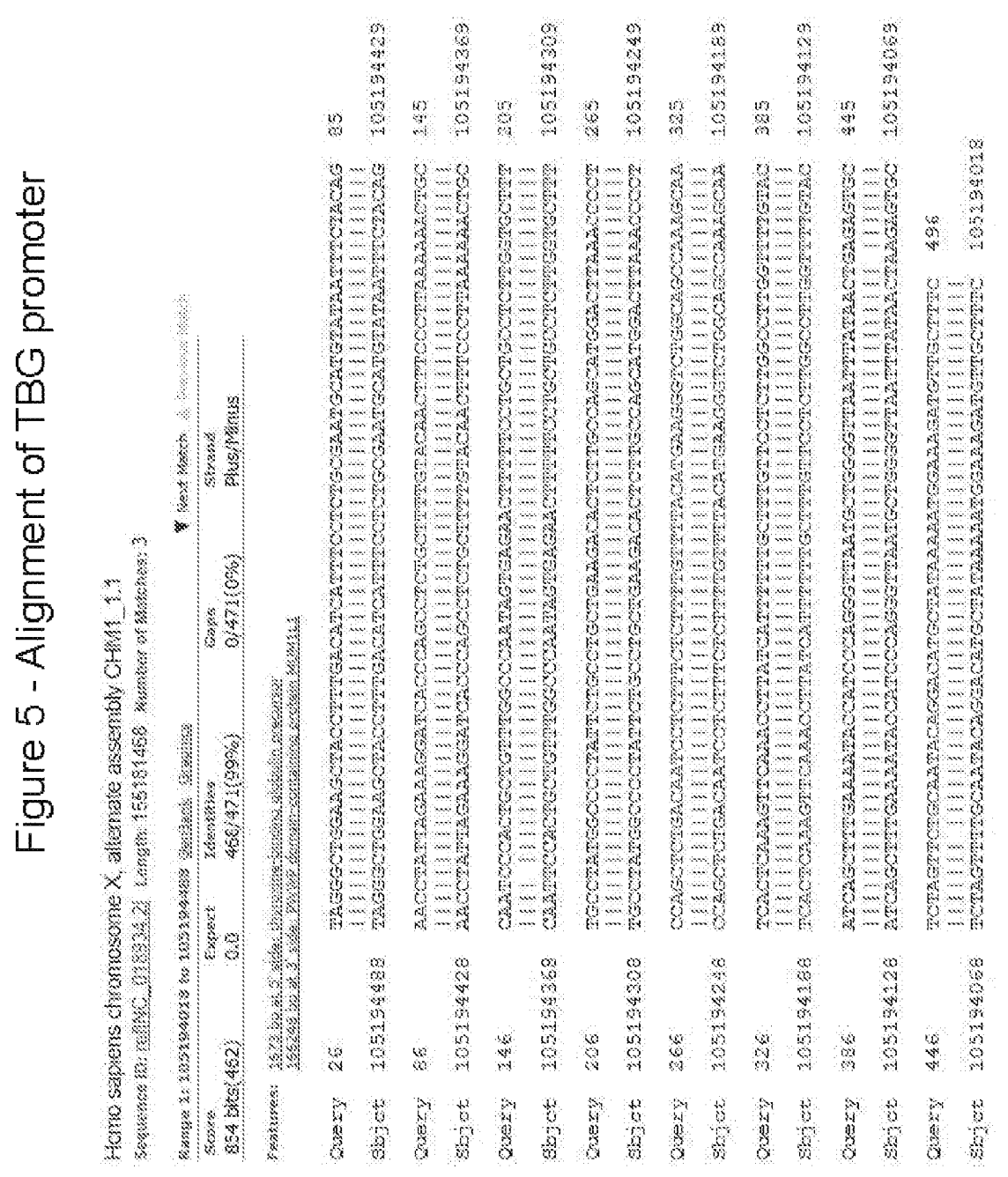

2. ABP/TBG liver specific hybrid promoter: The promoter sequences consist of two copies of the alpha 1 microglobulin/bikunin precursor enhancer element (ABP; Genbank # X67082.1; SEQ ID NO: 4; FIG. 4) which precedes the 495 bp hepatocyte-specific thyroxine-binding globulin (TBG; Genbank # L13470.1 SEQ ID NO: 5; FIG. 5) promoter and is used to drive high-level, liver specific hFIX gene expression.

3. Human beta globin intervening sequence (IVS) 2 intron (0.57 Kb; SEQ ID NO: 6). The 571 bp intron from the from the human beta globin intervening sequence 2 (IVS2; Genbank # NC 000011.9) is present in the vector expression cassette. The intron is transcribed, but removed from the mature mRNA by splicing, bringing together the sequences on either side of it. The presence of an intron in an expression cassette has been shown to facilitate the transport of mRNA from the nucleus to the cytoplasm, thus enhancing the accumulation of the steady level of mRNA for translation. This is a common feature in gene vectors intended for increased level of gene expression. See, Antoniou et al, Nucleic Acids Research, 26(3):721-9 (1998), which is incorporated by reference.

4. Human coagulation factor IX (FIX) cDNA (1.38 Kb; Genbank t#NM000133, complete CDS; SEQ ID NO: 1 shows native sequence; SEQ ID NO: 2 shows codon optimized sequence; SEQ ID NO: 13 shows alternate codon optimized sequence). The human coagulation factor 9 (FIX) cDNA encodes a coagulation factor essential for the formation of blood clots of 461 amino acids with a predicted molecular weight of 51.7 kD and an apparent molecular weight of 55 kD by SDS-PAGE. Codon optimized human FIX cDNA sequences were synthesized by Genart.

5. Woodchuck hepatitis virus posttranscriptional regulatory element: Between the coding sequence and the polyA is the woodchuck hepatitis virus posttranscriptional regulatory element (Genbank # J04514; SEQ ID NO: 7) with a single nucleotide mutation in the woodchuck hepatitis virus X (WHX) protein translation start.

6. Bovine growth hormone polyadenylation signal: (0.25 Kb; SEQ ID NO: 8) The 215 bp bovine growth hormone polyadenylation signal provides cis sequences for efficient polyadenylation of the hFIX mRNA. This element functions as a signal for transcriptional termination, a specific cleavage event at the 3' end of the nascent transcript followed by addition of a long polyadenyl tail.

Subsequently the ampicillin resistance gene in pENN.AAV.LSP.hFIXco3T.WPRE.bGH was excised and replaced with the kanamycin resistance gene to give pENN.AAV.LSP.hFIXco3T.WPRE.bGH.KanR (SEQ ID NO: 11).

7.2.2 AAVrh10 helper plasmid pAAV2.rh10.KanR

Figure 15:
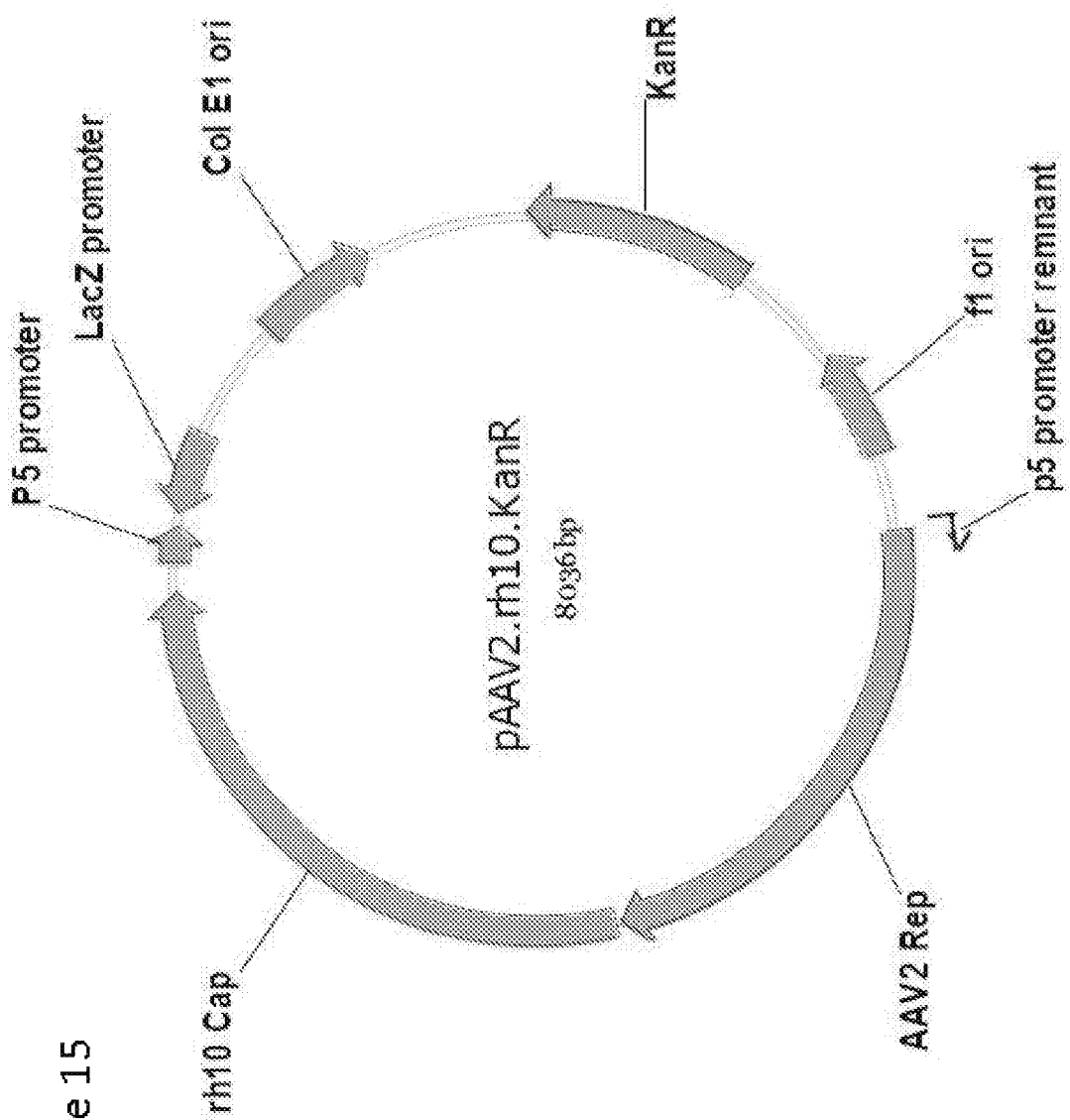

This AAVrh10 helper plasmid (8,036 bp) encodes the 4 wild-type AAV2 rep proteins and the 3 wild-type AAV VP capsid proteins from serotype rh10. A schematic of the pAAV2.rh10.KanR plasmid is shown in FIG. 15. A novel AAV sequence was obtained from the liver tissue DNA of a rhesus monkey and designated AAV serotype rh10. To create the chimeric packaging construct, the AAV2 cap gene was removed from plasmid p5E18 and replaced with a PCR fragment of the AAVrh0 cap gene amplified from a primate liver DNA to give plasmid p5E18VD2/rh10. Note that the AAV p5 promoter which normally drives rep expression is moved in this construct from the 5' end of rep to the 3' end of the rh10 cap gene. This arrangement serves to introduce a spacer between the promoter and the rep gene (i.e., the plasmid backbone) to down-regulate expression of rep and increase the ability to support high titer vector production. The plasmid backbone in p5E18 is from pBluescript KS. All component parts of the plasmid have been verified by direct sequencing. Finally the ampicillin resistance gene was replaced by the kanamycin resistance gene to give pAAV2/rh10 (Kan).

7.2.3 pAdDeltaF6(Kan) Adenovirus Helper Plasmid

Plasmid pAdDeltaF6(Kan) is 15,774 bp in size. The plasmid contains the regions of adenovirus genome that are important for AAV replication, namely E2A, E4, and VA RNA (the adenovirus E1 functions are provided by the 293 cells), but does not contain other adenovirus replication or structural genes. The plasmid does not contain the cis elements critical for replication such as the adenoviral inverted terminal repeats and therefore, no infectious adenovirus is expected to be generated. It was derived from an E1, E3 deleted molecular clone of Ad5 (pBHG10, a pBR322 based plasmid). Deletions were introduced in the Ad5 DNA to remove expression of unnecessary adenovirus genes and reduce the amount of adenovirus DNA from 32 kb to ~12 kb.

Finally the ampicillin resistance gene was replaced by the kanamycin resistance gene to give pAdΔF6(kan). The identity of these 3 adenovirus genes were confirmed by DNA plasmid sequencing performed by Qiagen Genomic Services on the plasmid source stock that was sent to Aldevron Inc for plasmid DNA manufacturing. DNA Analysis revealed 100% homology with the 3 Adenovirus type 5 gene regions (GenBank Accession number AF369965).

7.2.4 Bacterial Master Cell Banks (MCB)

Bacterial MCBs for the three DNA production plasmids that is used to support the manufacture of rAAVrh.10.LSP.hFIXco were produced by Aldevron Inc. Cell banks were made from the expansion of selected cultures and extensive testing was performed for qualification of each bacterial MCB following Aldevron SOPs and in accordance with CBER recommendations.

7.2.5 Plasmid DNA Manufacturing

All plasmids used in the production process were produced by Aldevron Inc. under its GMP-S™ quality system and infrastructure utilizing the most salient features of cGMP manufacturing; traceability, document control, and materials segregation.

7.2.6 Human Embryonic Kidney (HEK) 293 Master Cell Bank (MCB)

HEK 293 cells were originally generated by transforming HEK cells with sheared adenovirus type 5 DNA by Frank Graham and colleagues. The cells express the E1a and E1b gene products required for high-titer rAAV production. HEK293 cells are adherent and highly transfectable yielding high-titers of rAAV upon DNA plasmid transfection. The original source of the HEK293 cell seed was a vial of frozen cells from a research HEK293 cell bank (RCB) prepared in the GTP Wilson Vector Core HEK293 Cell Bank in June of 2012 (James Wilson laboratory at University of Pennsylvania). Subsequently, a vial was used to generate a second research bank One vial from the second research bank was then used to generate the MCB 7.3 Recombinant AAV Vector Manufacturing 7.3.1 Overview of the Manufacturing Process The rAAVrh.10.LSP.hFIXco DP is produced in a controlled environment consistent with FDA regulations ("Guidance for Industry—cGMP for Phase 1 Investigational Drugs", July 2008), which ensures the safety, identity, quality, purity and strength of the manufactured biologic. A manufacturing process flow diagram is shown in FIG. 12 and represents the rAAVrh.10.LSP.hFIXco vector production process. The major reagents entering into the preparation of the product have been indicated on the left side of the diagram. A description of each production and purification step is also provided. Product manufacturing follows a linear flow of unit operations and utilizes disposable, closed bioprocessing circuits unless otherwise specified. rAAVrh.10.LSP.hFIXco is the sole product manufactured within a specified production suite, with multiple BDS lots being anticipated that is tested separately prior to pooling to generate the final DP(s). All solutions are sterile filtered into sterile containers or are purchased sterile. Filters used in sterile filtration are filter integrity tested post use. All steps of the production process involving cell culture, from cell seeding to supernatant collection are performed aseptically using sterile, single-use disposable tubing and bag assemblies. Cells are cultivated in Corning Cell Stacks or Hyperstacks and all open manipulations re performed in class II biosafety cabinets in an ISO Class 5 environment. The purification process is performed in a closed system where possible however, column chromatography manipulations are not viewed as a completely closed system. To minimize this risk, single-use disposable flow paths re utilized as part of the GE ReadyMate column chromatography production skid platform. After column chromatography purification, the product is diafiltered with final formulation buffer and sterile filtered to yield the BDS and frozen at ≤−60° C. After BDS testing, the BDS is thawed, pooled, and diluted with sterile formulation buffer (20 mM Tris pH 80, 1 mM MgCl2, 200 mM NaCl, 0.001% Pluronic F68) and Filled at SAFC in their Fill Suite. Following Fill, the DP undergoes release testing and Quality Assurance review. The entire production process from cell expansion to fill is documented in executed Batch Record Documents (BRDs) that undergoes staff and QA technical review.

7.3.2 Description of the Manufacturing Process

1. Cell Seeding: A qualified human embryonic kidney 293 cell line is used for the production process. Cells are cultivated in medium composed of Dulbecco's Modified Eagle Medium (DMEM), supplemented with 10% gamma irradiated Fetal Bovine Serum (FBS). The cells are anchorage dependent and cell disassociation is accomplished using TrypLE Select, a non-animal cell dissociation reagent. The cells are maintained at 37° C. (+/−1° C.), in 5% (+/−0.5%) CO, atmosphere.

2. Transient Transfection: Following 3 days of growth (DMEM media+10% FBS), Hyperstack cell culture media is replaced with fresh, serum free DMEM media and transfected with the 3 production plasmids using an optimized PE precipitation method. All plasmids used in the production process are produced by Aldevron Inc. under its GMP-S™ quality system and infrastructure utilizing the most salient features of cGMP manufacturing; traceability, document control, and materials segregation.

Sufficient DNA plasmid transfection complex is prepared in the BSC to transfect twenty Corning 36-layer Hyper-Stacks (per BDS lot). Initially a DNA/PET mixture is prepared containing 3.0 mg of pDTX.hFIX.101 vector plasmid, 60 mg of pAdDeltaF6(Kan), 30 mg of pAAV2.rh0.KanR AAV helper plasmid and GMP grade PEI (PEIPro, PolyPlus Transfection SA). After mixing well, the solution is allowed to sit at room temperature for 25 min. and then added to serum-free media to quench the reaction and then added to the Corning 36-layer Hyperstacks. The transfection mixture is equalized between all 36 layers of the Hyperstack and the cells are incubated at 37° C. (+/−2° C.) in a 5% (+/−0.5%) $CO_2$ atmosphere for 5 days.

3. Cell Media Harvesting: Transfected cells and media are harvested from each Hypertack using disposable bioprocess bags by aseptically draining the medium out of the units. Following the harvest of media, the ~80 liter volume is supplemented with $MgCl_2$ to a final concentration of 2 mM (co-factor for Benzonase) and Benzonase nuclease (Cat#: 1.016797.0001. Merck Group) added to a final concentration of 25 units/ml. The product (in a disposable bioprocess bag) is incubated at 37° C. for 2-3 hr in an incubator to provide sufficient time for enzymatic digestion of residual cellular and plasmid DNA present in the harvest as a result of the transfection procedure. This step is performed to minimize the amount of residual DNA in the final vector DP. After the incubation period, NaCl is added to a final concentration of 500 mM to aid in the recovery of the product during filtration and downstream tangential flow filtration.

4. Clarification: Cells and cellular debris are removed from the product using a depth filter capsule (1.2 in/0.22 µm) connected in series as a sterile, closed tubing and bag set that is driven by a peristaltic pump. The media is passed through a Sartorius Sartoguard PES capsule filter (1.2 µm/0.22 µm, Sartorius Stedim Biotech Inc.).

5. Large-scale Tangential Flow Filtration: Volume reduction (10-20 fold) of the clarified product is achieved using Tangential Flow Filtration (TFF) using a custom sterile, closed bioprocessing tubing, bag and membrane set produced by Spectrum Labs.

6. Final Formulation and Sterile Filtration to yield the BDS: TFF is used to achieve final formulation on the pooled AEX fractions with a 100 kDa membrane (Spectrum Labs Inc.). The filtered Purified Bulk is stored in sterile polypropylene tubes and frozen at ≤−60° C. in a quarantine location until release for Final Fill.

7. Final Fill: The frozen BDS is thawed (and pooled if required) and filled into West Pharmaceutical's "Ready-to-Use" (pre-sterilized) 2 mL glass vials and 13 mm stoppers and seals at a fill volume >0.6 mL to <2.0 mL per vial. Individually labeled vials is labeled to include protocol number, product name, lot number, allocation number and stored in labeled boxes. Box labels contain protocol number, product name, lot number, fill volume, storage temperature, expiration date, route of administration, client name and warning information. Labeled vials are transferred to quarantine 5-60° C. until release.

7.4.1 Proposed in-Process Testing

Tests are performed on In-Process samples during the manufacturing and purification processes according to a detailed in process sampling plan. The test name, description of the test, and the laboratory in which they are performed are listed in Table 1 below.

TABLE 1

In-Process Methods

| Method | Method Description |
| --- | --- |
| BIOBURDEN | Based on the filtration of Sample onto 2 separate membranes, incubation of the membranes on 2 media types, and quantification of resulting colonies |
| qPCR GC Titer | GC titer determination based on degradation of non-encapsidated DNA followed by digestion of viral capsids. Released encapsidated DNA is quantified by qPCR targeting the the BGH polyA DNA sequence |
| ENDOTOXIN | Kinetic Chromogenic LAL Assay utilizing the cartridge based system from Charles River Laboratories. Cartridges include two sample wells to average duplicate results as well as two spike recovery wells to verify lack of inhibition/enhancement. |
| PURITY | Qualitative analysis of Purity based on SDS-PAGE of samples |
| MYCOPLASMA qPCR | Cellular and Mycoplasma DNA is extracted and quantified by A260 spectrophotometry. DNA is tested at a concentration of 120 µg/mL using a qPCR kit capable of identifying the most common species of mycoplasma. |
| HCP ELISA | Quantification of HEK293 Host Cell Protein by a Cygnus HEK293 ELISA. |
| HC-DNA qPCR | Quantification of host cell DNA using qPCR targeting the 18S gene and HEK293 gDNA |
| BENZONASE ELISA | Quantification of Benzonase using a commercial Benzonase ELISA |
| LEACHED AVB LIGAND ELISA | Quantification of leached camilid antibody fragment using a commercial AVB ELISA |
| BSA ELISA | Quantification of BSA using a commercial BSA ELISA |

7.4.2 Proposed Bulk Drug Substance Testing

Table 2 below provides details of the proposed BDS release testing performed.

TABLE 2

BDS Release Test Methods

| Test Method and Description | Acceptance Criteria |
| --- | --- |
| Bioburden USP <61> | <1 CFU/10 mL |
| Endotoxin USP <85> | <5 EU/mL |
| In-Vitro Assay for Viral Contaminants - Test Article is applied to Vero, MRC-5 & A549 cells and are monitored for viral contaminants[1] | Not Detected |
| Mycoplasma USP <63>[1] | Negative |
| Osmolality USP <785> | Osm 350-450 |
| pH USP <791> | 7.0-8.5 |
| Appearance - Visual inspection for Color, Appearance & Clarity | Clear to Slightly Opaque, Colorless to Faint White Solution |
| GC Titer by qPCR targeting the BGH poly A vector DNA sequence | ≥1.0 × 10¹³ GC/mL |
| AAV Purity Determination by SDS-PAGE | Purity >90% with no single impurity >4% |
| AAV Identity - SDS-PAGE Western Blot analysis with anti-AAV antibodies | Conforms to Reference Sample |
| Potency - FIX expression by human FIX ELISA following infection of Huh7 cells in vitro | Report Result |

FIX Identity - FIX expression by human FIX ELISA following infection of Huh7 cells in vitro
[1]Test Material for this assay is sampled at the time of Media & Cell harvest Table 3 below provides details of the proposed BDS characterization testing performed.

TABLE 3

BDS Characterization Test Methods

| Test Method and Description | Acceptance Criteria |
|---|---|
| AAV Capsid Protein ratio:CE-SDS | Report Result |
| Empty:Full particle ratio by AUC | Report Result |
| Empty:Full particle ratio by OD 260/280 | Report Result |
| GC titer by OD 260/280 | Report Result |
| Infectious Unit Titer: RC-32 cells w/ qPCR Detection (Bovine GH polyA target) | Report Result |
| Replication competent AAV (RCAAV) detection by triple passage on HEK293 cells + Ad5 | Report Result |
| Plasmid DNA (free and packaged) by qPCR to Kan gene target | Report Result |
| HEK293 E1a DNA by qPCR | Report Result |
| HEK 293 HCP by ELISA | Report Result |
| AAV Vector Genome Sequencing | 100% Match to expected sequence |
| HC-DNA by qPCR | Report Result |
| Residual Benzonase ELISA | Report Result |
| AVB Leached Ligand ELISA | Report Result |
| BSA ELISA | Report Result |

8. EXAMPLE 3: AAV.HFIXCO IN ANIMAL MODELS 8.1 Preliminary Animal Studies for Investigation of Hemophilia B Gene Therapy Several preliminary studies were conducted in animals to prepare for the formal IND-enabling studies that are described below. These studies employed either a precursor to our proposed hFIX expression cassette or the actual proposed hFIX expression cassette. The AAVrh10 capsid was constant throughout these studies although in certain studies, comparisons were made to an AAV8 capsid bearing the same hFIX expression cassette. These preliminary studies included assessments of safety and of the MED. These studies included the AAV8 vs AAVrh10 expression comparison (data not shown).

8.2 AAVrh10 Gene Therapy in the Mouse Models of Hemophilia B 8.2.1 Evaluation of rAAVrh.10.LSP.hFIXco in a Factor IX Knockout Mouse Model A Factor IX knockout mouse model was developed as an appropriate animal model for studying the efficacy of delivery of Factor IX by way of AAV gene therapy vectors and was used previously by numerous investigators for research studies and for IND-enabling studies. See, Wang, Lili, et al. "A factor IX-deficient mouse model for hemophilia B gene therapy." Proceedings of the National Academy of Sciences 94.21 (1997): 11563-11566. This model is a reasonable approximation of a severe hemophilia B patient because there is no Factor IX protein produced and the animals have a severe clotting dysfunction. The last 164 amino acids at the C terminus of the Factor IX protein and the 3' untranslated region are deleted. There is no evidence of truncated Factor IX mRNA or protein. The Factor IX knockout mouse was backcrossed to C57B1/6 strain background and was maintained by homozygous female mating with hemizygous male.

rAAVrh.10.LSP.hFIXco (whose vector genome is nt 1 to nt 3951 of SEQ ID NO: 11) was evaluated in the Factor IX knockout mouse model described above to verify Factor IX activity of the vector and to provide a preliminary assessment of the minimal effective dose (MED). The MED in this study was based on achieving therapeutic levels of hFIX (5% of normal). The vector was assessed at six doses after intravenous administration: $8 \times 10^7$, $2.7 \times 10^8$, $2.7 \times 10^9$, $2.7 \times 10^{10}$, $2.7 \times 10^{11}$ and $8 \times 10^{11}$ GC/mouse.

Mice were bled at 2 and 4 weeks following vector administration and Factor IX antigen and activity levels were determined by hFIX ELISA and aPTT, respectively. The following observations were noted:

1. Factor IX knockout mice receiving rAAVrh.10.LSP.hFIXco at the dose of $2.7 \times 10^9$ GC/mouse achieved normal levels of hFIX activity.

2. MED for rAAVrh.10.LSP.hFIXco lied between $2.7 \times 10^8$ and $2.7 \times 10^9$ GC/mouse ($1.35 \times 10^{10}$ GC/kg-$1.35 \times 10^{11}$ (GC/kg).

3. hFIX activity reached a plateau of close to 1000% of normal level at the dose of $2.7 \times 10^{10}$ GC/mouse, while hFIX antigen reached a plateau of 1000% of normal at the dose of $2.7 \times 10^{11}$ GC/mouse.

4. Mice with super physiological levels of hFIX appeared normal, and no animal death was observed at any of the six dose groups (see FIG. 11).

8.2.2 Evaluation of rAAVrh.10.LSP.hFIXco in C57B1/6 Mice

Figure 14:
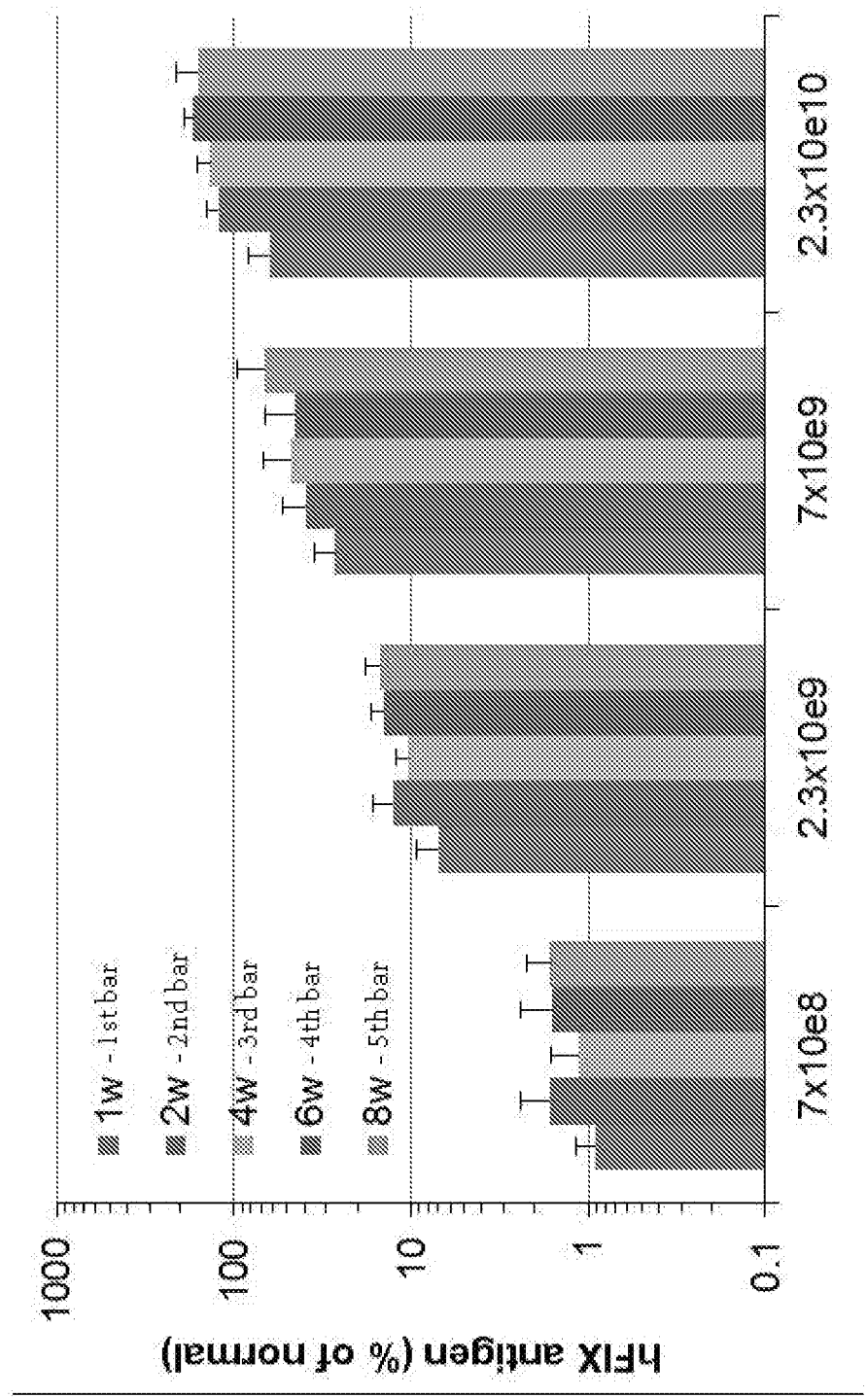

A dose-response study was conducted in C57B1/6 male mice. rAAVrh.10.LSP.hFIXco was assessed at four doses after intravenous administration: $7 \times 10^8$, $2.3 \times 10^9$, $7 \times 10^9$, and $2.3 \times 10^{10}$ GC/mouse. Factor IX levels were observed above therapeutic levels (5% of normal; 100%=5 ug/ml) at a dose of $2.3 \times 10^9$ GC/mouse ($1.1 \times 10^{11}$ GC/kg), and above normal levels at $2.3 \times 10^{10}$ GC/mouse ($1.1 \times 10^{12}$ GC/kg). See FIG. 14. The hFIX antigen levels in C57B1/6 mice were about 3-fold lower than those in Factor IX knockout mice.

8.3 Observed Differences in Gene Expression Between Mice and Non-Human Primate (NHP)

8.3.1 Introduction

An important factor in comparing relative expression of AAV vectors in different species is the rationale for scaling the dose. The method for dosing in AAV gene therapy studies directed to liver is based on total mass of the organism. The only complete data set of mouse, non-human primate (NHP) and human that is available for liver directed gene therapy is with AAV8 in patients with hemophilia B. Review of these data is nonetheless complicated due to changes in the quantitative assessment of vector titer reported by the inventors during the development of the product. A review of the published data suggested a 10-20-fold reduction in expression when comparing mice to monkeys and expression that is similar to, or slightly reduced, when comparing monkeys to humans.

Studies comparing transgene expression in mice and nonhuman primates with vectors based on AAV8 and AAVrh10 are summarized below. The same method of assessing vector titer was identical throughout except as otherwise noted. Both methods were based on TaqMan qPCR although the standard method yielded results that were 2-3-fold lower than the optimized method.

8.3.2 Relative expression of EGFP in mice and macaques for AAV8 and AAVrh10

Following systemic injection of $3 \times 10^{12}$ GC kg AAV8 or AAVrh10.TBG.EGFP in two rhesus macaques each, GFP expression was lower than that observed in mice receiving a similar dose (data not shown). Transduction efficiency was quantified by percentage of GFP-positive area in the liver and GFP intensity (data not shown). The reduction was 4 and 14-fold lower with AAV8 based on percentage transduction and intensity, respectively. The reduction was 5.5-fold with AAVrh10 based on percentage transduction.

8.4 Animal Studies

Three animal models are used to further evaluate the safety, biodistribution and efficacy of rAAVrh.10.LSP.hFIXco: C57Bl/6 wild-type mouse, a Factor IX knockout mouse model, and a non-human primate model.

8.4.1 Hemophilia B Mouse Model

1. Animal Model

The Factor IX knockout mouse model is an appropriate animal model for studying the efficacy of delivery of Factor IX by way of AAV gene therapy vectors. This model has been used previously by numerous investigators for research studies and for IND-enabling studies. This model is a reasonable approximation of a severe hemophilia B patient because there is no Factor IX protein produced and the animals have a severe clotting dysfunction.

Two cohorts of male FIX-KO mice were included in the study. The initial cohort (Subset A) was evaluated for 90 days following dose administration on Day 0 and was terminated on Day 90. A second cohort (Subset B) was evaluated for 28 days following dose administration on Day 0 and was terminated on Day 28.

2. Administration

For both Subset A and Subset B, male FIX-KO mice (7/group) were administered vector doses once on Day 0 by intravenous injection into the tail vein. The vector was formulated in Vehicle Buffer composed of 0.001% Pluronic F-68 in TMN200 (200 mM sodium chloride, 1 mM magnesium chloride, 20 mM Tris, pH 8.0). The vector dose levels tested were $1.6 \times 10^{10}$ GC/kg, $5.0 \times 10^{10}$ GC/kg, $1.6 \times 10^{11}$ GC/kg, $5.0 \times 10^{11}$ GC/kg, $5.0 \times 10^{12}$ GC/kg, and $5.0 \times 10^{13}$ GC/kg. Each mouse received the test article formulations at a dose volume of 0.150 mL/mouse. Dose concentrations were calculated based on the average Day 0 mouse weight for each dose group.

For each subset, concurrent control groups were administered the vehicle once on Day 0, also by intravenous injection into the tail vein at a dose volume of 0.150 mL/mouse.

3. Justification of Gender of the Animal

Only male FIX-KO mice were used for this study, as hemophilia B is an X-linked genetic disorder that affects only males. Proposed clinical trials are carried out in male hemophilia B patients.

4. Coagulation

Measurements of PT (prothrombin time) in FIX-KO male mouse plasma were determined using a Stago ST Art Start Hemostasis Coagulation Analyzer set to PT mode and Dade Innovin Reagent. Normal PT values for male FIX-KO mice range from 6.8-8.2 seconds with mean and standard deviation of 7.3±0.3 seconds, respectively (FIG. 7).

Measurements of hFIX activity in FIX-KO male mouse plasma were determined by a one-step aPTT-based Factor IX assay using a Stago ST Art Start Hemostasis Coagulation Analyzer set to aPTT mode. A standard curve was generated using known concentrations of human FIX in FIX deficient plasma. Samples were compared to the standard curve to obtain the relative activity of hFIX within each plasma sample. Samples at higher concentrations required dilution in FIX deficient plasma to obtain levels within the interpretable range. Results were presented as percent of normal human plasma activity.

4. hFIX Protein Levels

The circulating levels of hFIX in mouse plasma were determined using an hFIX ELISA using a coating antibody (Haematologic Technologies) and an HRP-conjugated detecting antibody (Cedarlane) specific to human factor IX (FIG. 6).

5. Anti-hFIX Antibodies

The presence of murine anti-hFIX antibodies in mouse serum collected on Days 28 and 90 was determined using an anti-hFIX IgG ELISA assay.

6. Quantification of vector genomes and hFIXco mRNA in liver

Sections of the liver were removed and placed into sterile tubes, snap-frozen on dry ice, and stored at <−65° C. for QPCR and RT-QPCR studies. DNA and RNA were extracted. QPCR and RT-QPCR assays were performed on the extracted liver DNA/RNA to measure vector DNA copies and hFIXco transcript levels in the liver by real-time PCR (TaqMan Universal Master Mix, Applied Biosystems).

7. Statistical Analysis

For FIX expression data, cohort average and standard deviation were calculated and reported. Analysis of variance was performed using GraphPad Prism 6 to determine any vector-related effects.

8.4.2 Non-Clinical Study of rAAVrh.10.LSP.hFIXco in Rhesus Macaque

The primary objective of this non-GLP study is to evaluate the potential vector related toxicity and biodistribution in rhesus macaques to support the safety of rAAVrh.10.LSP.hFIXco for the clinical trial. rAAVrh.10.LSP.hFIXco is examined at $1.0 \times 10^{13}$ GC/kg which is 2 fold higher than the proposed clinical high dose.

Male rhesus macaques aged 2 to 3 years are used for this study. Only male animals are used in the study since hemophilia B is an X-linked genetic disorder. A minimum of three animals per time point are enrolled into the study. Animals are screened for pre-existing neutralizing antibodies (NAbs) to AAVrh.10 before study starts, only animals with neutralizing antibodies (NAbs)<1:10 are used in this study.

Animals receive vector via the saphenous vein in a total volume of 10 ml. After vector administration, the animals are monitored daily for general observations. At time of necropsy, on day 90 and 360, the organs (such as brain, lung, muscle, kidney, heart, spleen, liver, stomach, small intestine, large intestine, pancreas, lymph node, testis, haired skin, gross lesions if any) are harvested for a complete gross pathology and histopathology examination. Additionally, blood is collected for a complete serum chemistry panel, hematology, and gene expression at selected time points. hFIX protein levels in the plasma are analyzed by a hFIX ELISA assay. For immunology, antigen specific T-cell responses are examined on days 14, 28, and every 28 days using an interferon gamma ELISPOT assay which allows an examination of antigen specific T-cells directed against either the capsid or transgene. Humoral immune responses to AAV capsid at selected time points are examined using a neutralizing or binding antibody assay. Antibody responses (inhibitors) to human Factor IX are examined using an ELISA.

C57Bl/6 and the existence of a large body of data from multiple sponsors using different AAV vectors makes the safety data developed in this model relevant. The non-human primate is an appropriate model in particular for studying the potential immune responses to AAV vectors and the tolerability of high doses of AAV vectors in an animal that is closely related to humans.

8.5. Testing of Vector

Characterization assays including serotype identity, empty particle content and transgene product identity are performed. Descriptions of all the assays appear below.

8.5.1 Genomic Copy (GC) Titer

An optimized quantitative PCR (oqPCR) assay is used to determine genomic copy titer by comparison with a cognate plasmid standard. The oqPCR assay utilizes sequential digestion with DNase I and Proteinase K, followed by qPCR analysis to measure encapsidated vector genomic copies. DNA detection is accomplished using sequence specific primers targeting the hBG polyA region in combination with a fluorescently tagged probe hybridizing to this same region. Comparison to the plasmid DNA standard curve allows titer determination without the need of any post-PCR sample manipulation. A number of standards, validation samples and controls (for background and DNA contamination) have been introduced into the assay. This assay has been qualified by establishing and defining assay parameters including sensitivity, limit of detection, range of qualification and intra and inter assay precision. An internal AAVrh.10 reference lot was established and used to perform the qualification studies.

8.5.2 Vector Capsid Identity: AAV Capsid Mass Spectrometry of VP3

Confirmation of the AAV2/rh.10 serotype of the vector is achieved by an assay based upon analysis of peptides of the VP3 capsid protein by mass spectrometry (MS). The method involves multi-enzyme digestion (trypsin, chymotrypsin and endoproteinase Glu-C) of the VP3 protein band excised from SDS-PAGE gels followed by characterization on a UPLC-MS/MS on a Q-Exactive Orbitrap mass spectrometer to sequence the capsid protein. A tandem mass spectrometry (MS) method was developed that allows for identification of certain contaminant proteins and deriving peptide sequence from mass spectra.

8.5.3 Empty to Full Particle Ratio

Vector particle profiles are using analytical ultracentrifugation (AUC) Sedimentation velocity as measured in an analytical ultracentrifuge is an excellent method for obtaining information about macromolecular structure heterogeneity, difference in confirmation and the state of association or aggregation. Sample was loaded into cells and sedimented at 12000 RPM in a Beckman Coulter Proteomelab XL-I analytical ultracentrifuge. Refractive index scans were recorded every two minutes for 3.3 hours. Data are analyzed by a c(s) model (Sedfit program) and calculated sedimentation coefficients plotted versus normalized c(s) values. A major peak representing the monomeric vector should be observed. The appearance of peaks migrating slower than the major monomeric peak indicates empty/misassembled particles. The sedimentation coefficient of the empty particle peak is established using empty AAV8 particle preparations. Direct quantitation of the major monomeric peak and preceding peaks allow for the determination of the empty to fill particle ratio.

8.5.4 Infectious Titer

The infectious unit (IU) assay is used to determine the productive uptake and replication of vector in RC32 cells (rep2 expressing HeLa cells). Briefly, RC32 cell in 96 well plates are co-infected by serial dilutions of vector and a uniform dilution of Ad5 with 12 replicates at each dilution of rAAV. Seventy-two hours after infection the cells are lysed, qPCR is performed to detect rAAV vector amplification over input. An end-point dilution TCID50 calculation (Spearman-Karber) is performed to determine a replicative titer expressed as IU/ml. Since "infectivity" values are dependent on particles coming into contact with cells, receptor binding, internalization, transport to the nucleus and genome replication, they are influenced by assay geometry and the presence of appropriate receptors and post-binding pathways in the cell line used. Receptors and post-binding pathways critical for AAV vector import are usually maintained in immortalized cell lines and thus infectivity assay titers are not an absolute measure of the number of "infectious" particles present. However, the ratio of encapsidated GC to "infectious units" (described as GC/IU ratio) can be used as a measure of product consistency from lot to lot.

8.6 Readministration with Second Vector 8.6.1 Readministration of AAV3B or AAV5

The efficiency of vector readministration using AAV3B or AAV5 in rhesus macaques previously treated with AAVrh10 or AAV8 vectors was evaluated. Vectors as shown in Table 4 were produced as previously described in which the vector was recovered from the supernatant following triple transfection in HEK293 cells and purified on an iodixanol gradient. Vector titer was determined by a digital PCR method.

Twenty four male rhesus macaques (3-5 years old) were enrolled into study in 8 groups (n=3/group; Table 1) based on the status of pre-existing NAb. Macaques were injected on day zero with $1.0 \times 10^{13}$ GC/kg of the AAV vector as shown in Table 4. At week 12, macaques received a second injection with $1.0 \times 10^{13}$ GC/kg of the AAV vector as shown in Table 4. Liver biopsies were performed at week 2 and week 14, and a necropsy was performed at week 26.

TABLE 4

Cohort and Vector Summary

| Cohort | Animal ID | 1st Injection | 2nd Injection |
|---|---|---|---|
| G1A | RA0931<br>RA1388<br>RQ9745 | PBS | AAV3B.TBG.rhAFP |
| G1B | RA0923<br>RA1275<br>RQ9383 | PBS | AAV5.TBG.rhAFP |
| G2A | RA0985<br>RQ9638<br>RQ9746 | AAVrh10.TBG.rhCG.WPRE | AAV3B.TBG.rhAFP |
| G2B | RA0992<br>RA1322<br>RA1417 | AAVrh10.TBG.rhCG.WPRE | AAV5.TBG.rhAFP |
| G3A | RA1234<br>RQ9737<br>RQ9751 | AAV8.TBG.rhCG.WPRE | AAV3B.TBG.rhAFP |
| G3B | RA1339<br>RA1390<br>RQ9805 | AAV8.TBG.rhCG.WPRE | AAV5.TBG.rhAFP |
| G4 | RA0548<br>RA0658<br>RQ9840 | AAV3B.TBG.rhCG.WPRE | N/A |
| G5 | RA0968<br>RA1208<br>RA1239 | AAV5.TBG.rhCG.WPRE | N/A |

Expression levels of transgenes (rhCG—rhesus chorionic gonadotropin b subunit; rhAFP—rhesus alpha fetoprotein) in the serum were measured by enzyme-linked immunosorbent assay (ELISA). To measure vector DNA copies in liver, QPCR assays were performed on total cellular DNA extracted from liver samples collected during liver biopsy and necropsy. AAV NAb assay was performed as previously described. Liver sections were stained with an anti-CG antibody for imaging.

Figure 16:
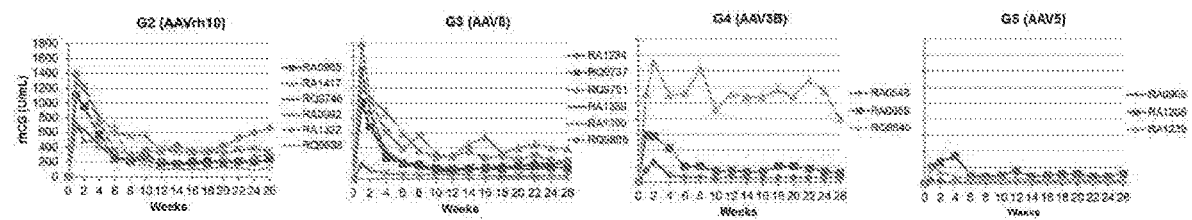
FIG. 16 shows a comparison of rhCG expression levels by AAVrh10, AAV8, AAV3B and AAV5 vectors (first vector injection).
Figure 17:
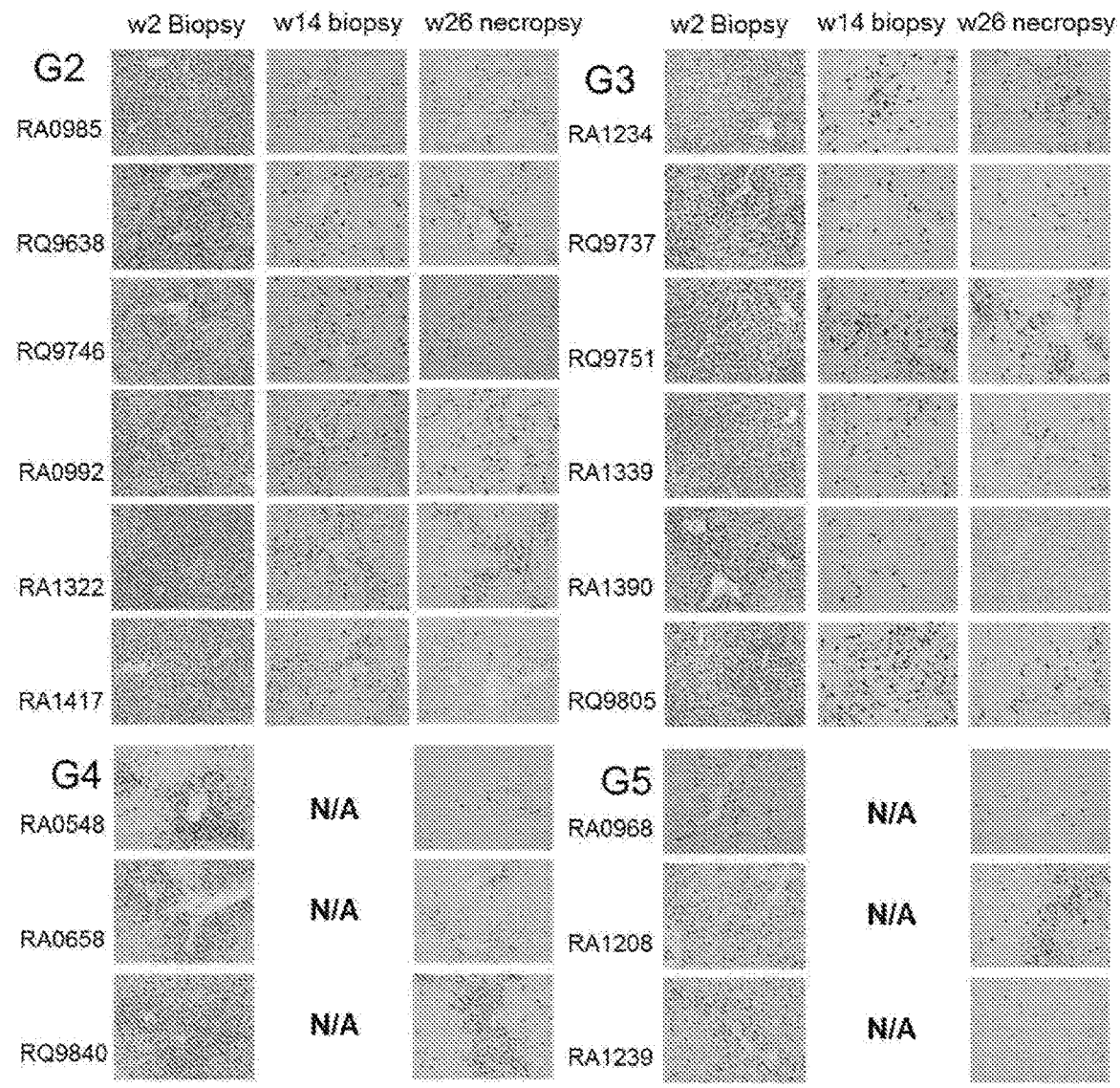
FIG. 17 shows expression of rhCG in the liver at different time points.
Figure 18A:
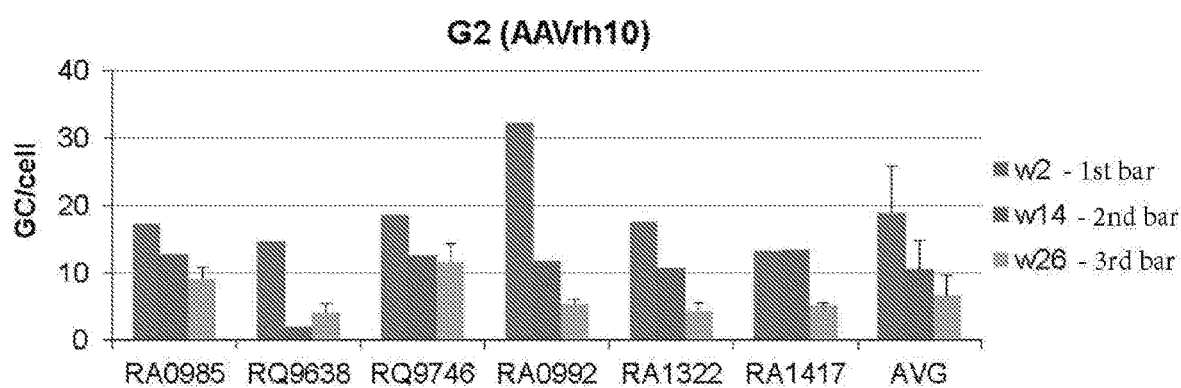
FIGS. 18A-18D show a rhCG vector DNA copies in liver at different time points.
Figure 18B:
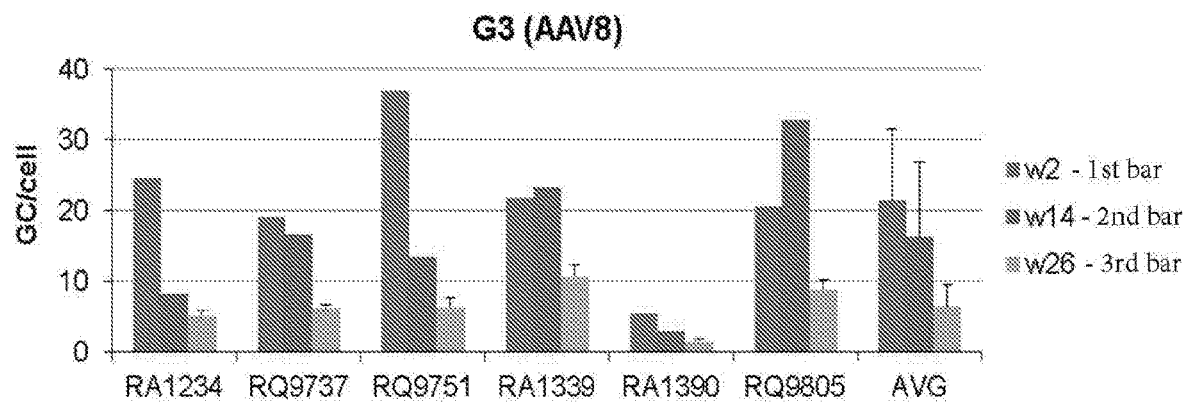
Figure 18C:
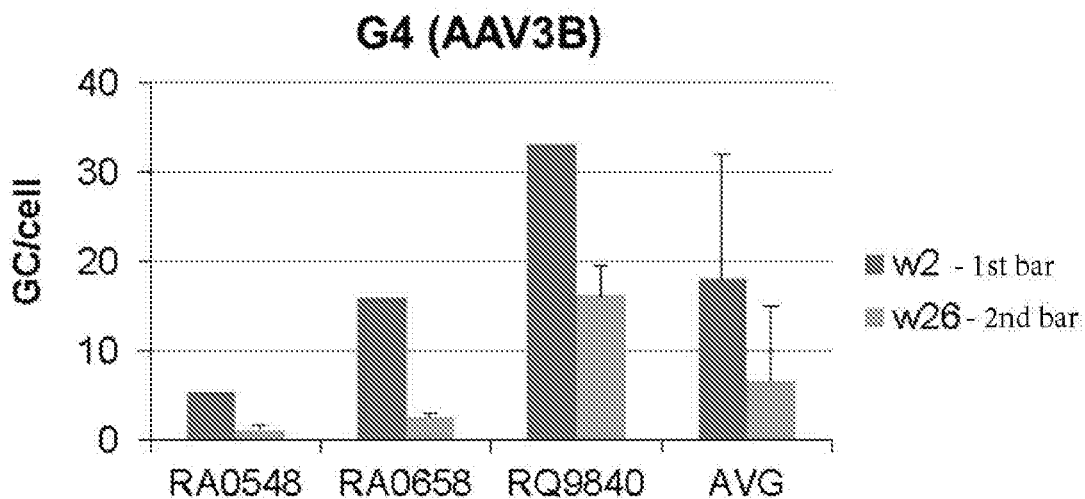
Figure 18D:
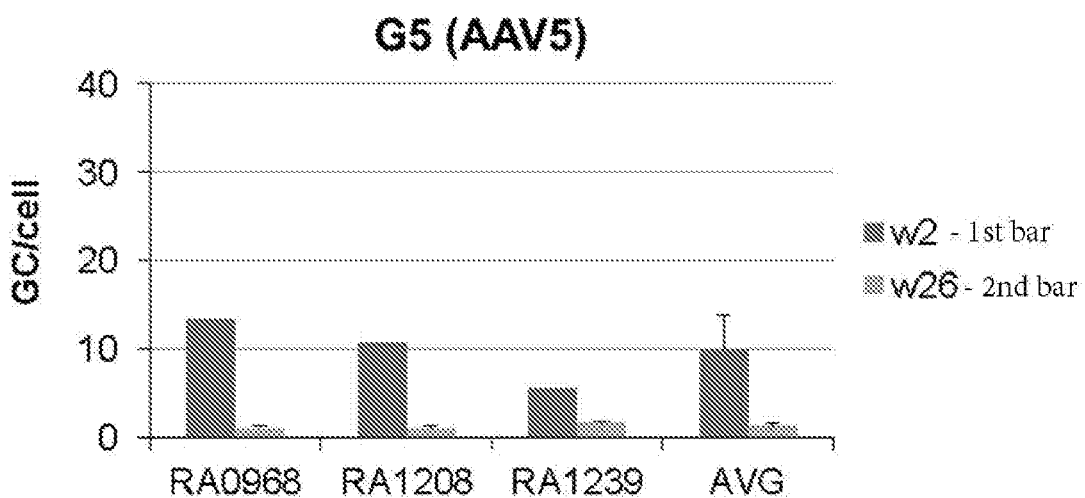
Figure 19A:
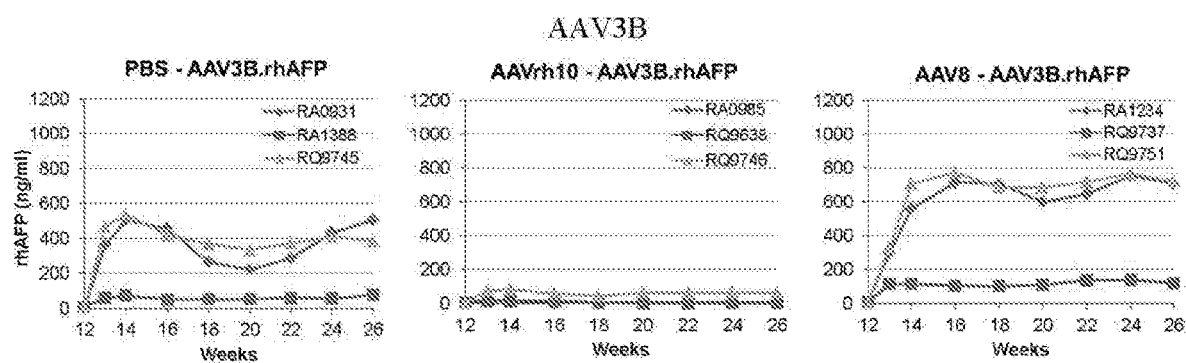
FIGS. 19A-19B shows rhAFP levels after readministration (second vector injection) with AAV3B or AAV5 vectors expressing rhAFP.
Figure 19B:
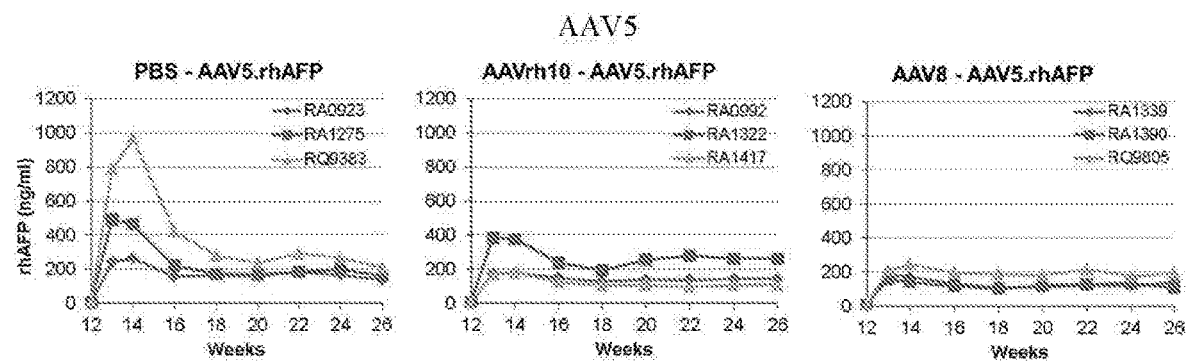
Figure 20A:
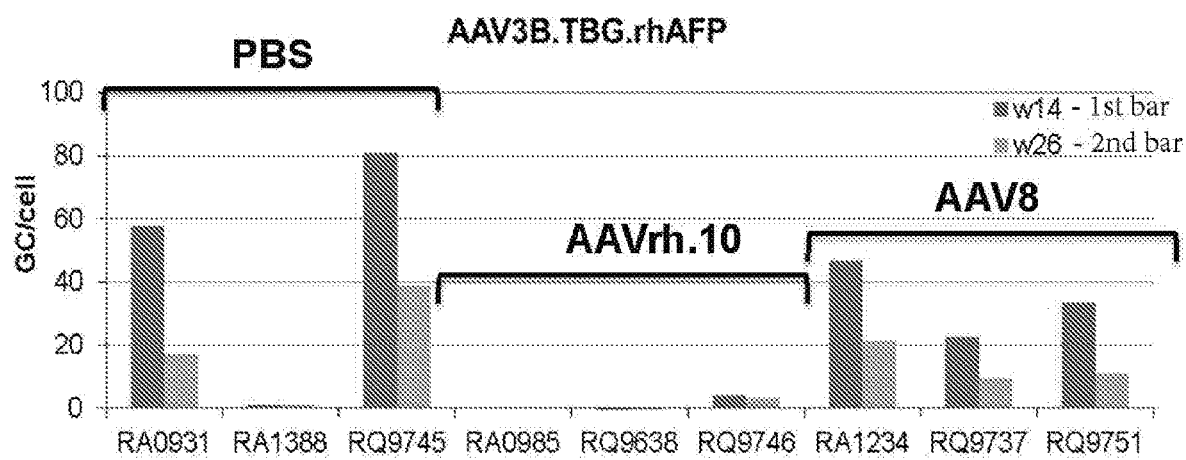
FIGS. 20A and 20B show rhAFP vector genome copies in liver.
Figure 20B:
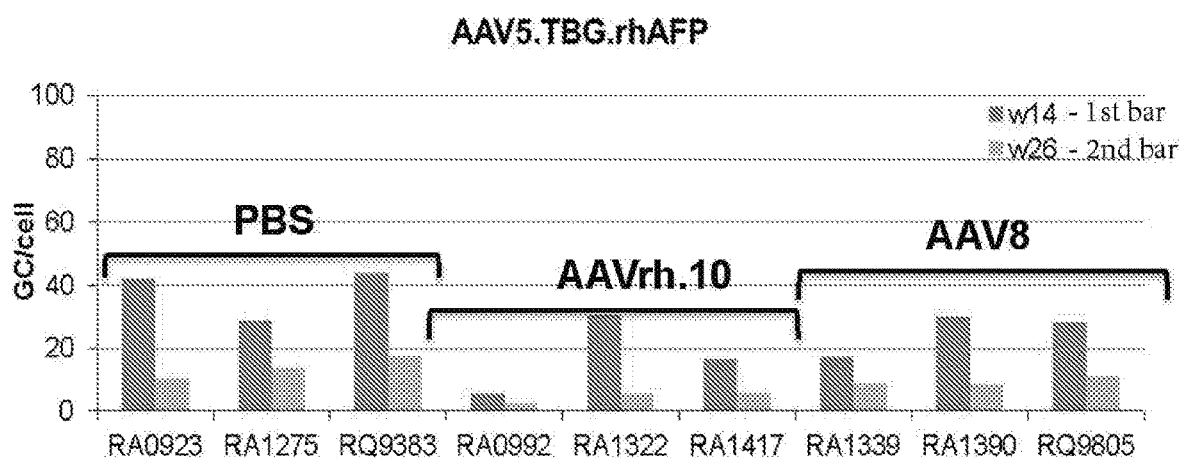
Figure 21:
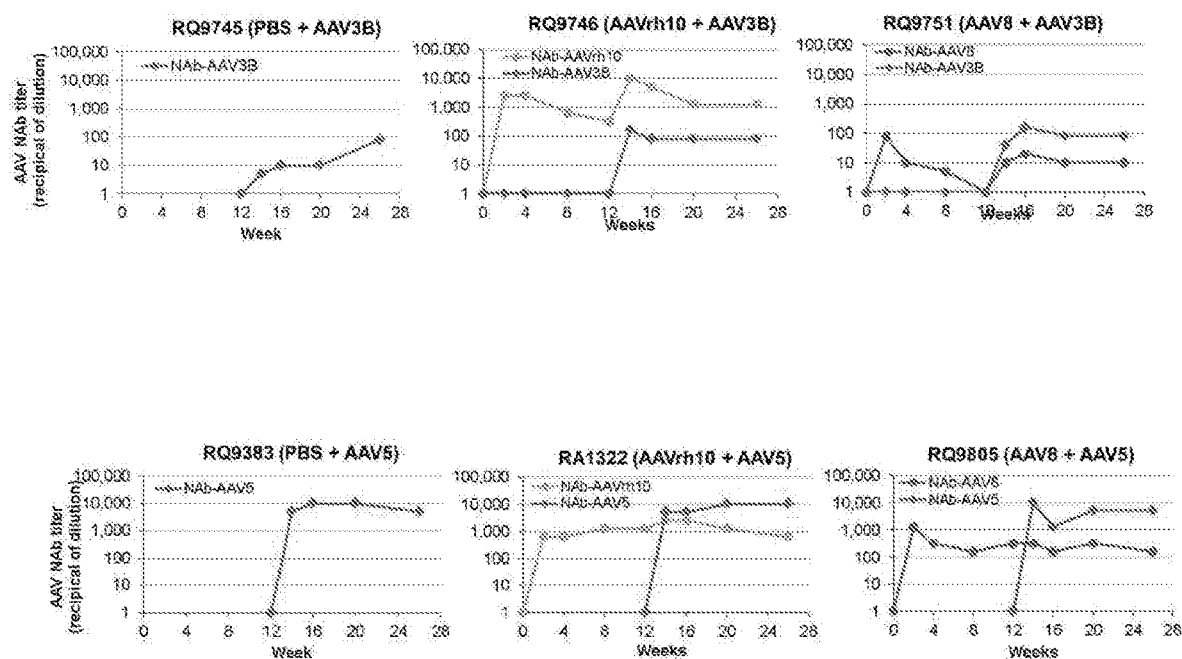
FIG. 21 shows differential AAV Nab response in macaques.

FIG. 16 shows a comparison of rhCG expression levels by AAVrh10, AAV8, AAV3B3 and AAV5 vectors (first vector injection). FIG. 17 shows expression of rhCG in the liver at different time points. FIG. 18A-18D shows rhCG vector DNA copies in liver at different time points by AAVrh110, AAV8, AAV3B and AAV5 vectors. FIGS. 19A and 19B show rhAFP levels after readministration (second vector injection) with AAV3B or AAV5 vectors expressing rhAFP. FIG. 20A and FIG. 20B show rhAFP vector genome copies in liver for the listed vectors. FIG. 21 shows differential AAV Nab response in macaques.

In naïve animals, clade E vectors (AAVrh10 & AAV8) demonstrated the highest levels of periportal gene transfer with AAV5 vectors having the lowest. The periportal zone is nearest to the entering vascular supply, receives the most oxygenated blood, and is an important region of the liver for metabolic processes. AAVrh0 and AAV5 elicited higher levels of neutralizing antibodies (NAb) than AAV8 and AAV3B. Significant animal-to-animal variation in transgene expression was noted with AAV3B in seronegative animals. Within the short time frame tested, NAb elicited from AAVrh10 inhibited subsequent in vivo transduction with the serologically distinct AAV3B serotype. Prior exposure to AAV8 did not interfere with AAV3B transduction.

8.7 Further Animal Studies 8.7.1 Comparison of AAVrh10.hFIXco3T and AAVrh10.hFIXco3T-Padua (SEQ ID NO: 16.

FIX knock out mice were treated as follows:

TABLE 5

| Group (n = 6-7 mice/group) | Vector | Dose (QPCR) GC/mouse |
|---|---|---|
| G1 | DTX101 | 3 × 10e7 |
| G2 | (AAVrh10.hFIXco3T) | 1 × 10e8 |
| G3 | | 1 × 10e9 |
| G4 | | 1 × 10e10 |
| G5 | | 1 × 10e11 |
| G6 | | 3 × 10e11 |
| G7 | AAVrh10.hFIXco3T- | 3 × 10e7 |
| G8 | Padua | 1 × 10e8 |
| G9 | | 1 × 10e9 |
| G10 | | 1 × 10e10 |
| G11 | | 1 × 10e11 |
| G12 | | 3 × 10e11 |

Mice were bled at weeks 2, 4 and 6 and tested for hFIX antigen by ELISA and activity (APTT), as discussed in Example 8.4. At week 6, mice were euthanized by terminal bleeds (superchem and CBC performed). Tissues were harvested for histology & liver genome copies.

Figure 23:
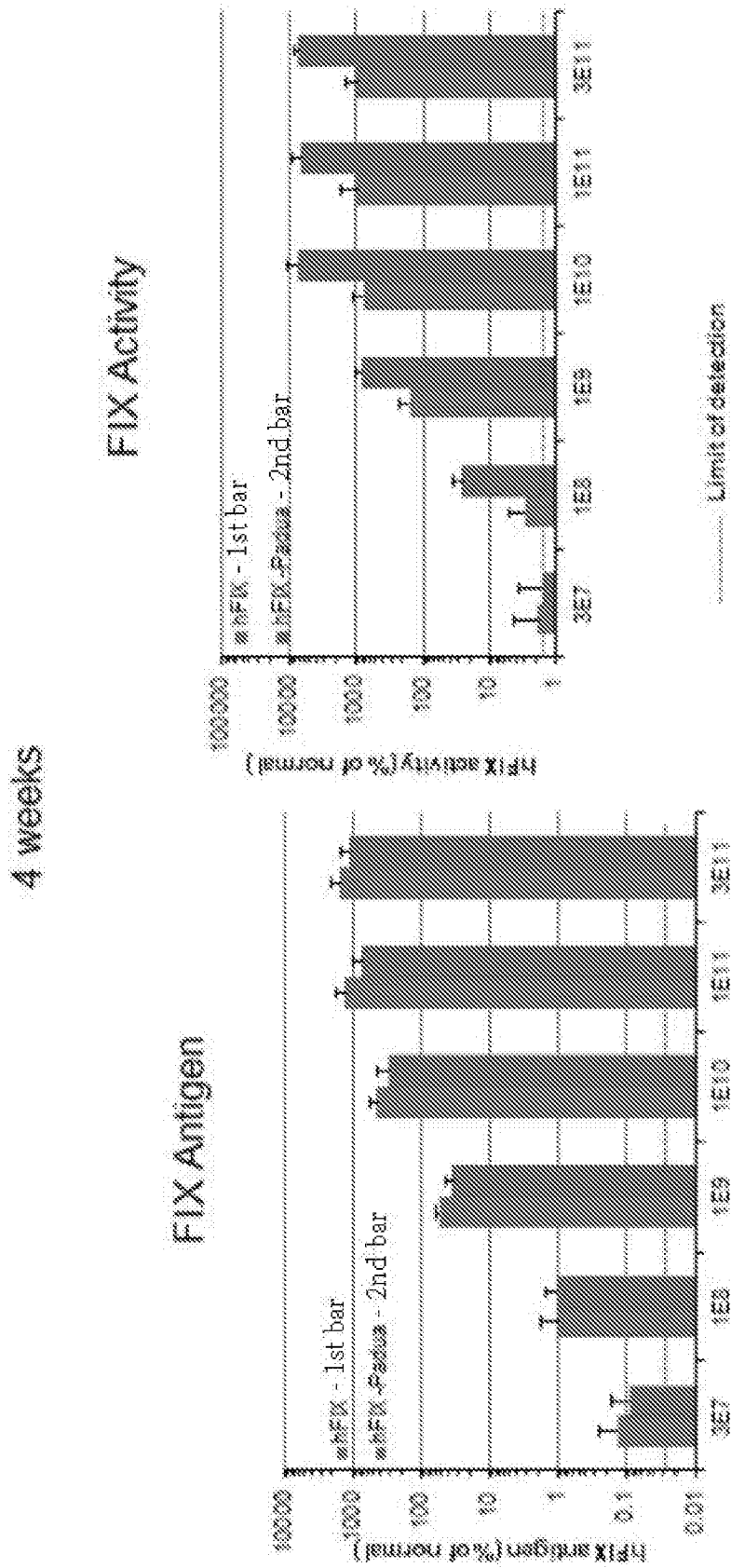
FIG. 23 shows FIX antigen and activity levels in animals injected with vectors carrying the hFIXco and hFIXco3T-Padua at 4 weeks post injection.
Figure 24:
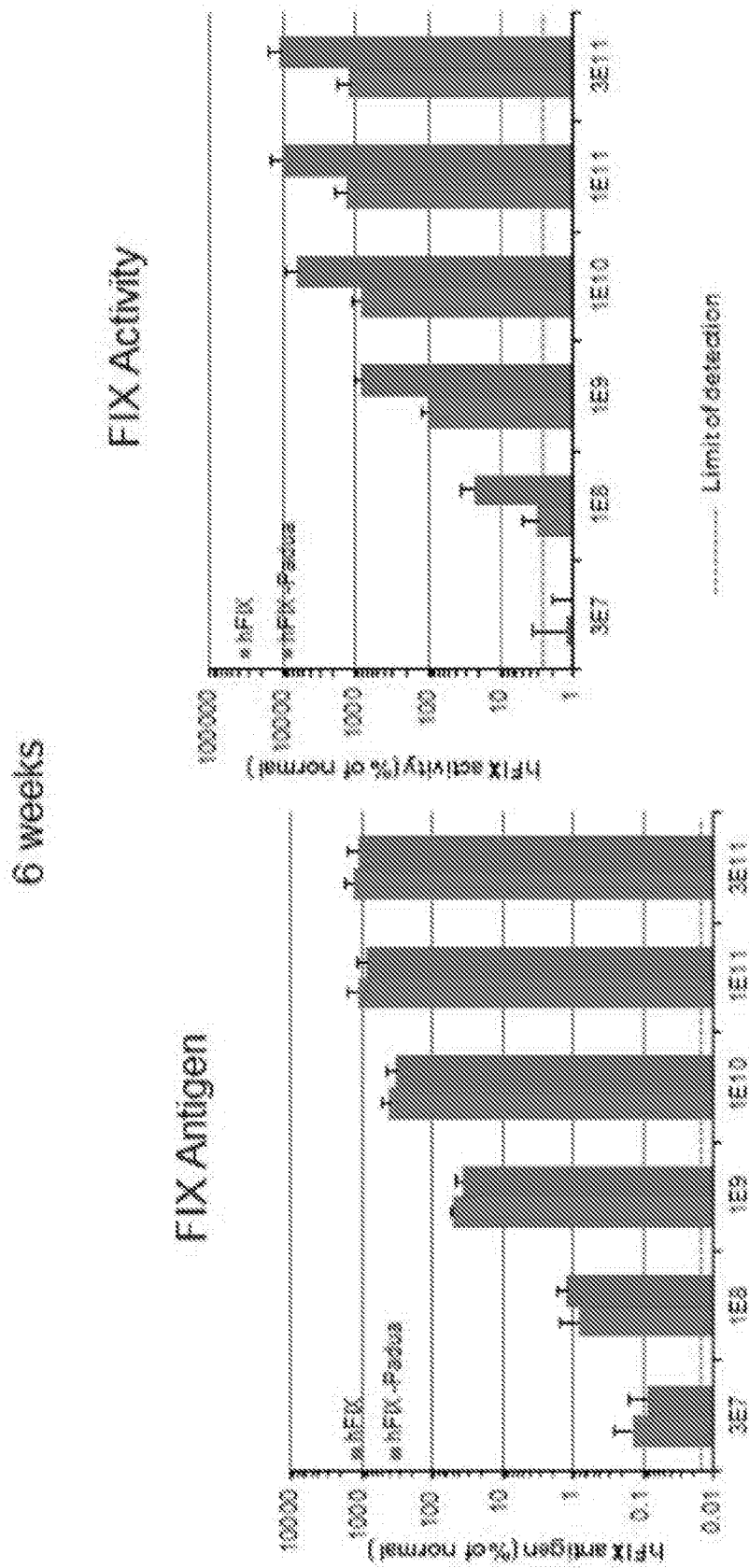
FIG. 24 shows FIX antigen and activity levels in animals injected with vectors carrying the hFIXco and hFIXco3T-Padua at 6 weeks post injection.
Figure 25:
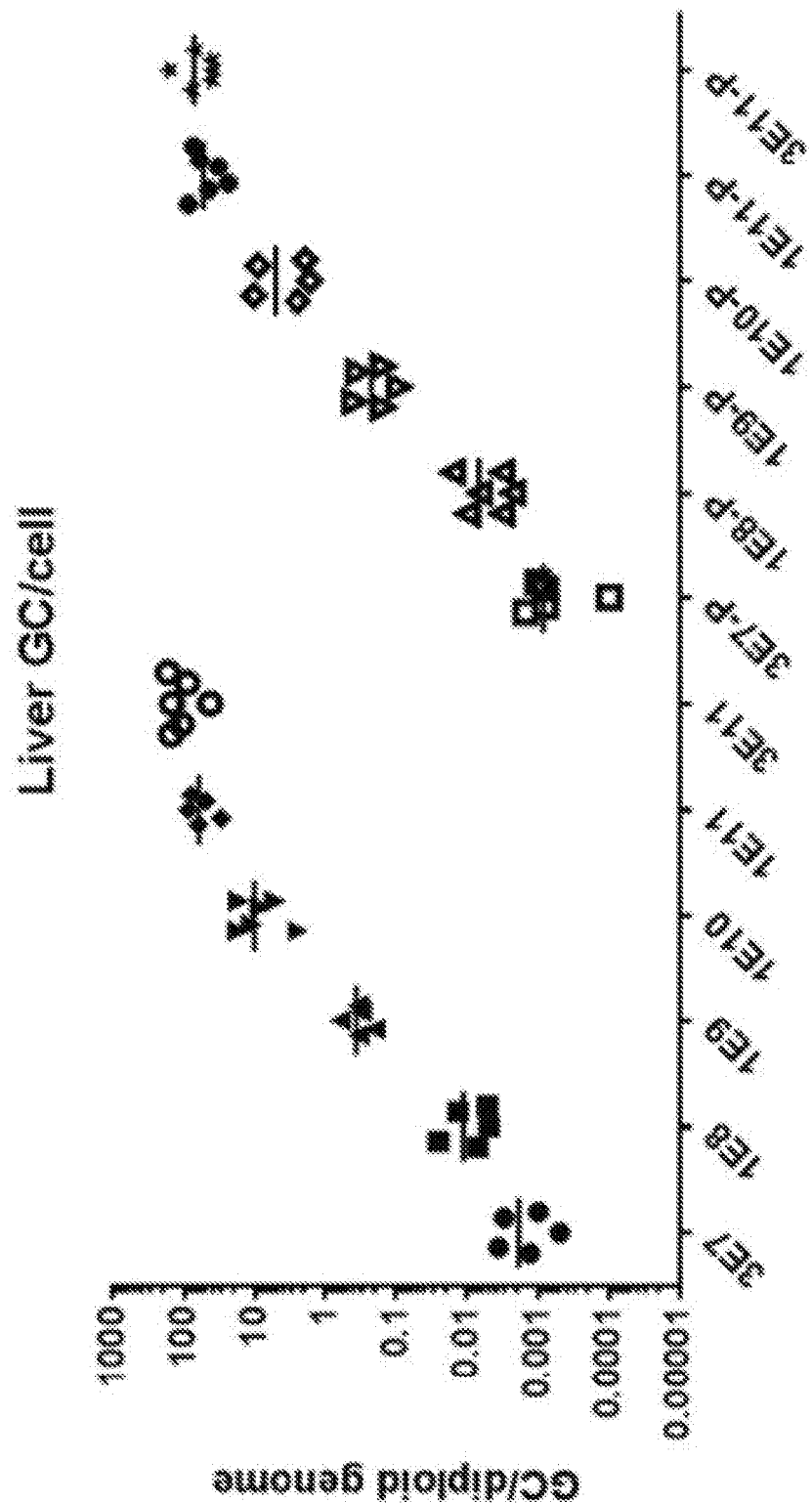
FIG. 25 shows vector genome copies (GC) in liver 6 weeks post injection for various dosages of vector.

FIX antigen and activity levels at 2, 4, and 6 weeks are shown in FIGS. 22-24 respectively. Vector genome copies in liver at 6 weeks are shown in FIG. 25. FIX-KO mice treated with AAVrh10.hFIXco3T-Padua achieved similar hFIX antigen levels but 7-8 fold higher hFIX activity. FIX-KO mice treated with $1\times10^8$ GC of AAVrh10.hFIXco3T-Padua achieved above therapeutic levels (5% of normal) of hFIX activity. hFIX antigen levels plateaued at the dose of $1\times10^{11}$ GC/mouse, while hFIX activity levels plateaued at 1×1010 GC/mouse, likely due to the limitation of other factors or cofactor.

Figure 26:
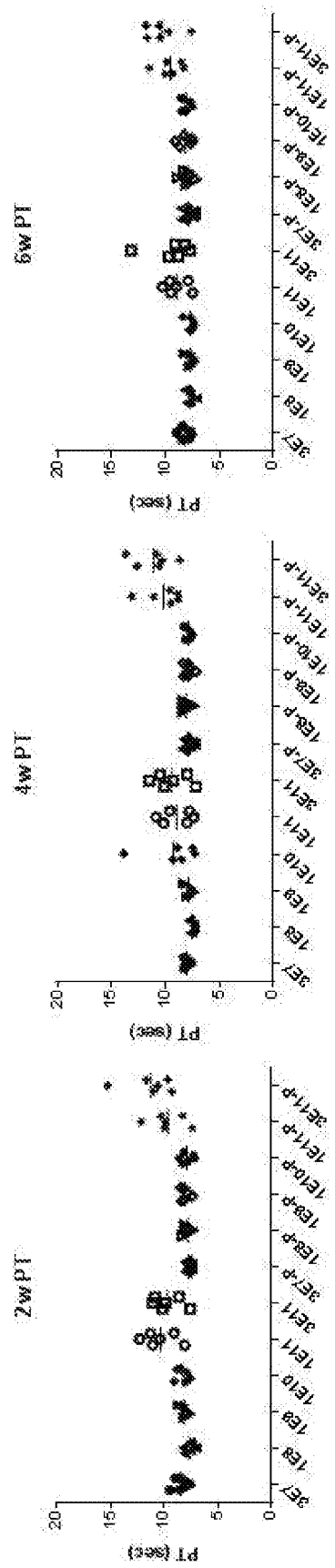
FIG. 26 shows a time course of prothrombin time (PT) in animals treated with various dosages of vector at 2 weeks, 4 weeks and 6 weeks post injection.

A time course of prothrombin time (PT) was performed at 2, 4, and 6 weeks (FIG. 26). Elevation of PT was observed in animals treated with high doses of vector (1×1011 or 3×1011 GC/mouse), likely due to the over production of hFIX and exhaustion of post translational modification pathways which are shared by other factors in the coagulation pathway.

In summary, DTX101 and hFIXco3T-Padua treated mice expressed similar levels of hFIX antigen. hFIXco3T-Padua treated mice had 7-8 fold higher FIX activity than DTX101-treated mice. Based on activity levels, MED for DTX101 is between 1E8-1E9 GC/mouse in hemophilia B mouse, MED for hFIX-Padua is <1E8 GC/mouse. Abnormal PT was observed in mice treated with either vector at doses ≥1E11 GC/mouse. DTX101 and hFIX-Padua treated mice showed similar serum chemistry and hematologic parameters at w6. Histology analysis on H&E stained tissue sections from the 3E11 GC dose groups showed similar findings in liver (minimal-mild hepatitis) and heart (mild myocardial degeneration). In lung, 2 out of 6 Padua (3E11 GC)—treated mice showed focal alveolar edema.

8.8 Human Clinical Studies

Six patients were administered AAVrh10.hFIXco3T vector gene therapy intravenously (i.v.) and composed the low-dose ($1.6\times10^{12}$ GC/kg) and mid-dose cohort ($5.0\times10^{12}$ GC/kg) of the hemophilia B clinical trial. Table 7 below provides Enzyme-Linked ImmunoSpot; ELISPOT results representing SFUs (spot forming units) per million lymphocytes at various time-points throughout the study. AAV vector injections were performed on a rolling basis as subjects were enrolled in the trial. The ELISPOT results represent T-cell responses against specific peptide pools from the AAV capsid of interest (AAVrh.10) and transgene (FIX). All lymphocytes used in the ELISPOT assay were isolated from peripheral blood and positive ELISPOT (T-cell) responses are noted in bold font with an asterisk.

Figure 27B:
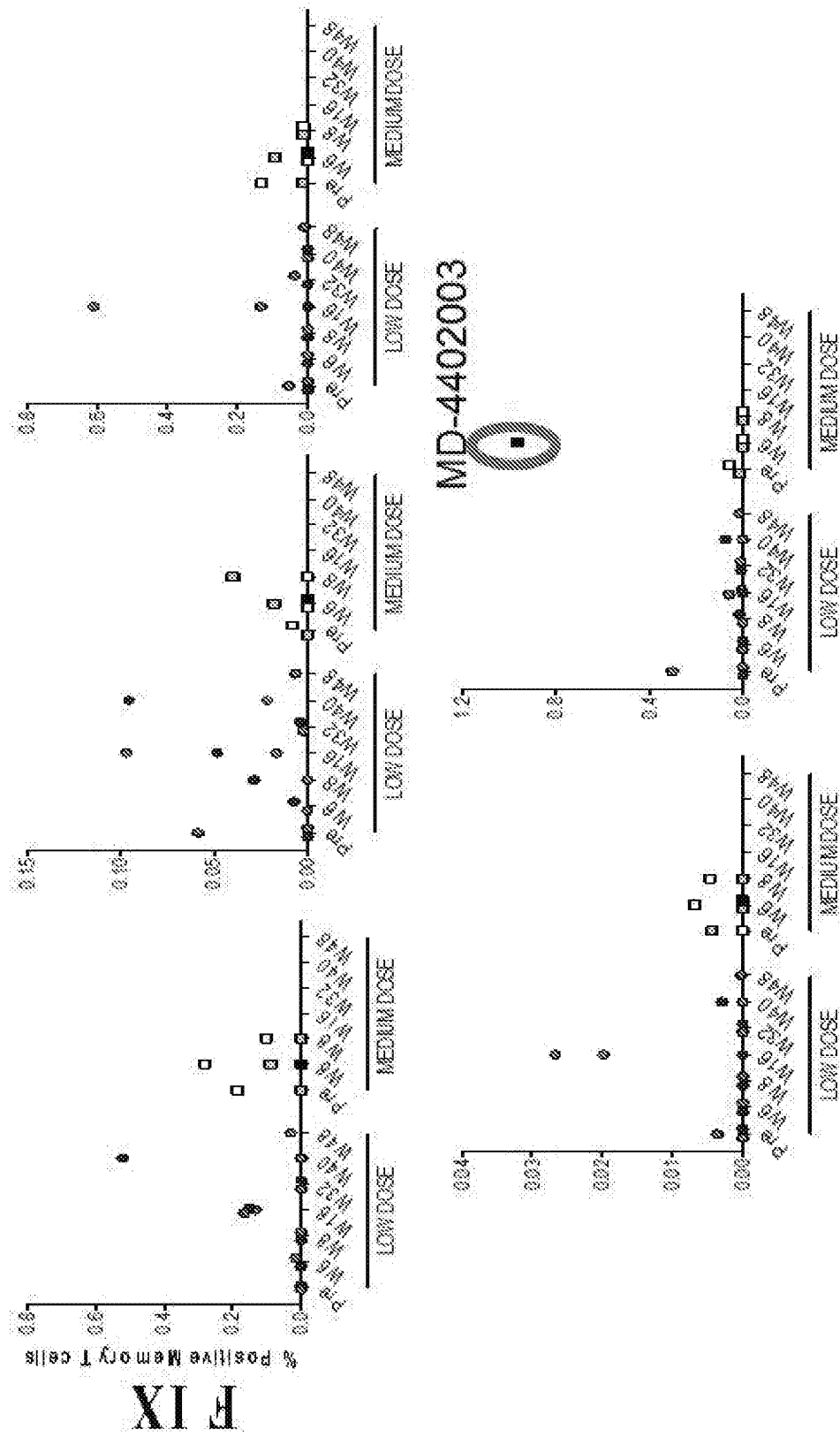
Figure 27C:
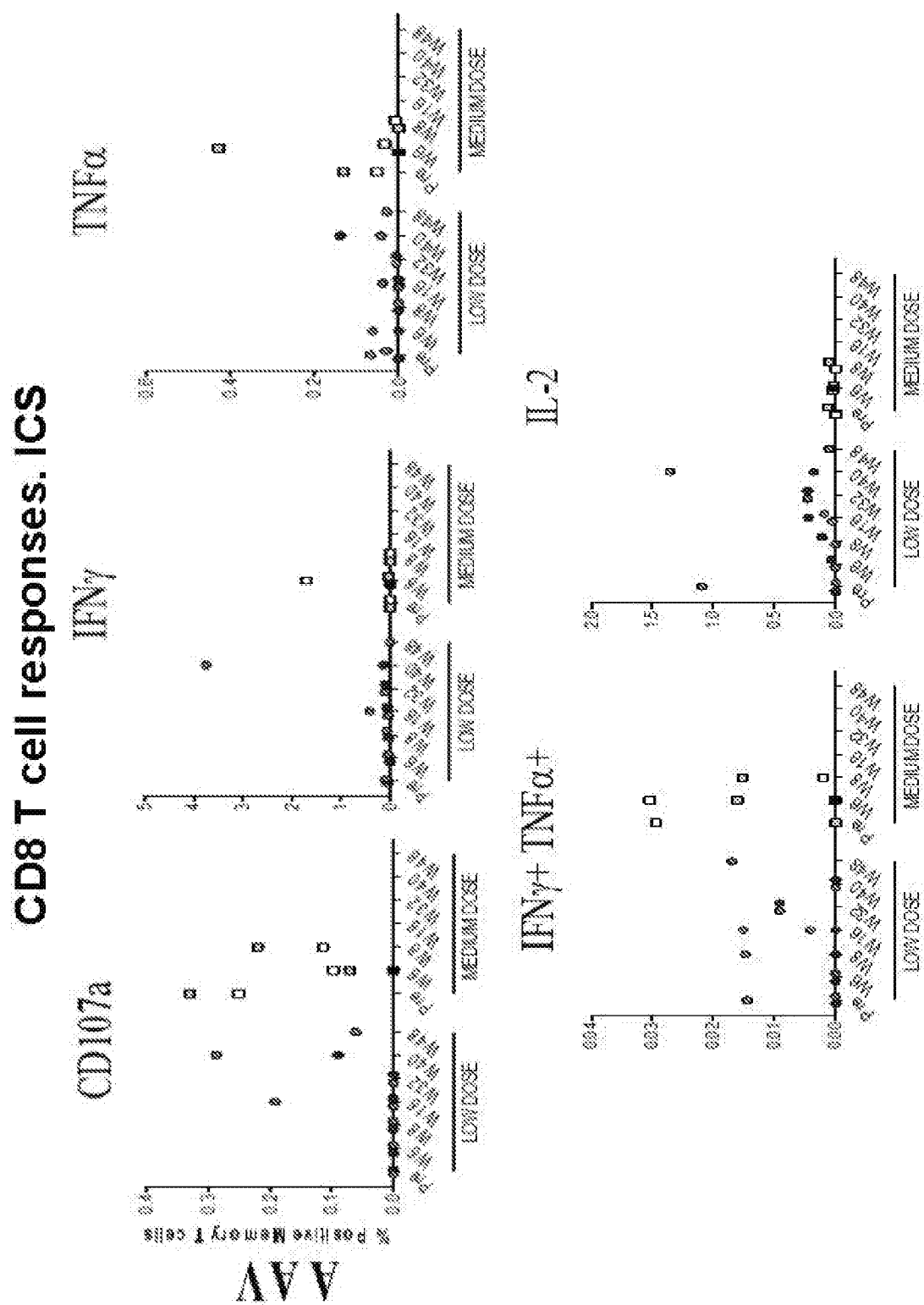
Figure 28A:
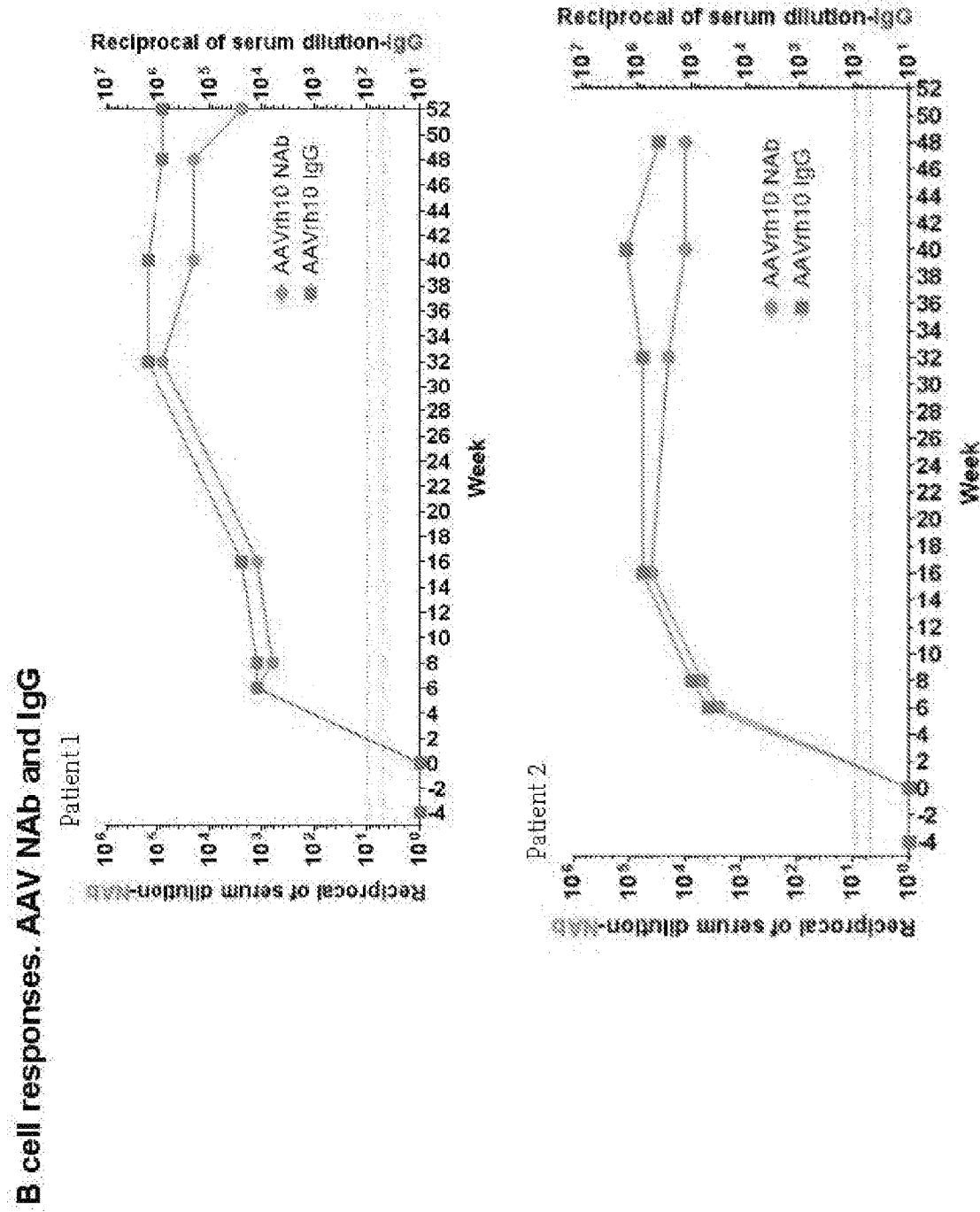
FIG. 28A-28C are graphs showing neutralizing antibodies (NAbs) and Immnunoglobulin-G (IgG) responses to the AAV capsid of interest (AAVrh.10) from isolated serum of six patients receiving the low- or mid-dose of the vector discussed for FIGS. 27A and B. All results are reported as the reciprocal of serum dilution.
Figure 28B:
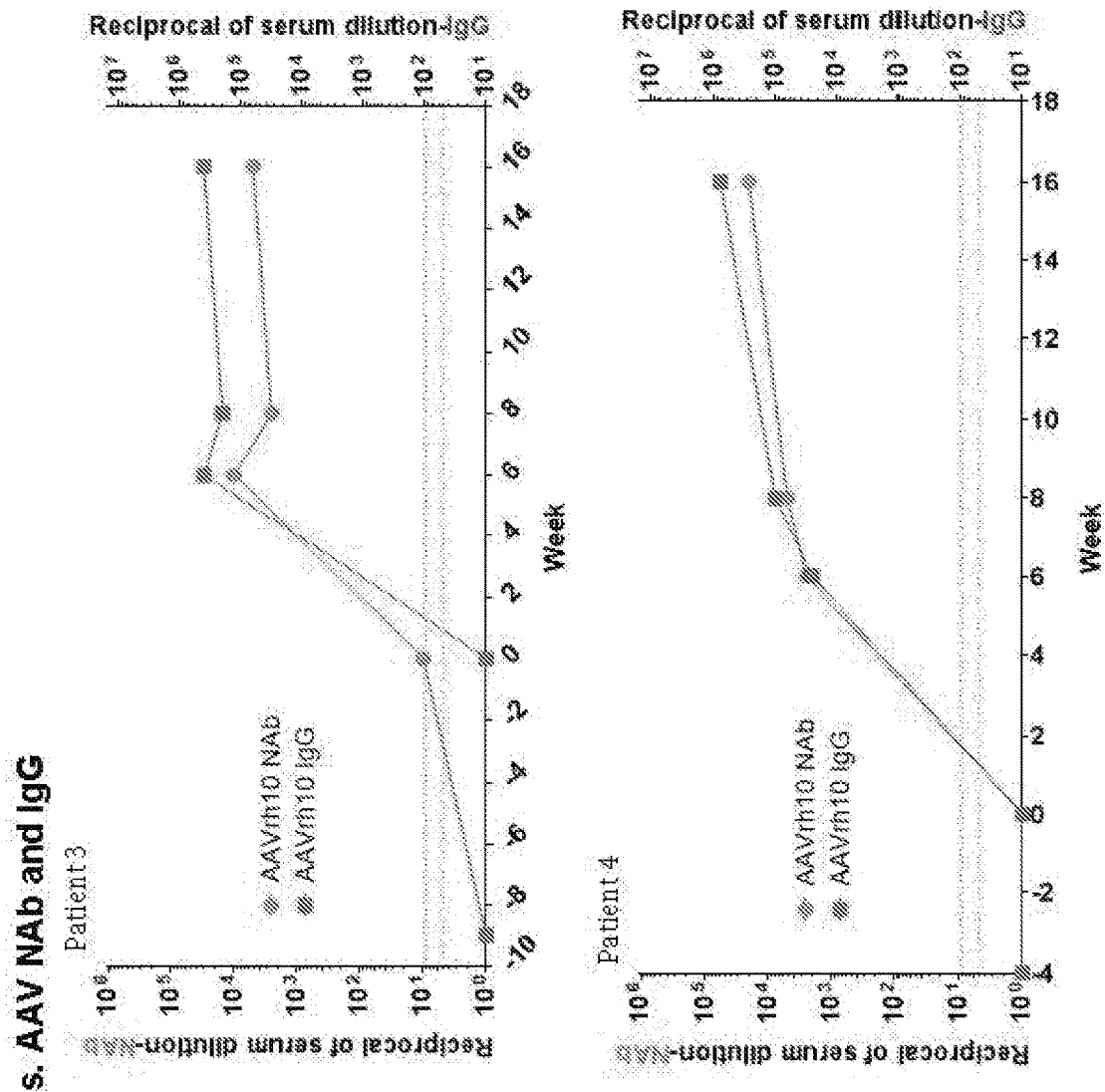
Figure 28C:
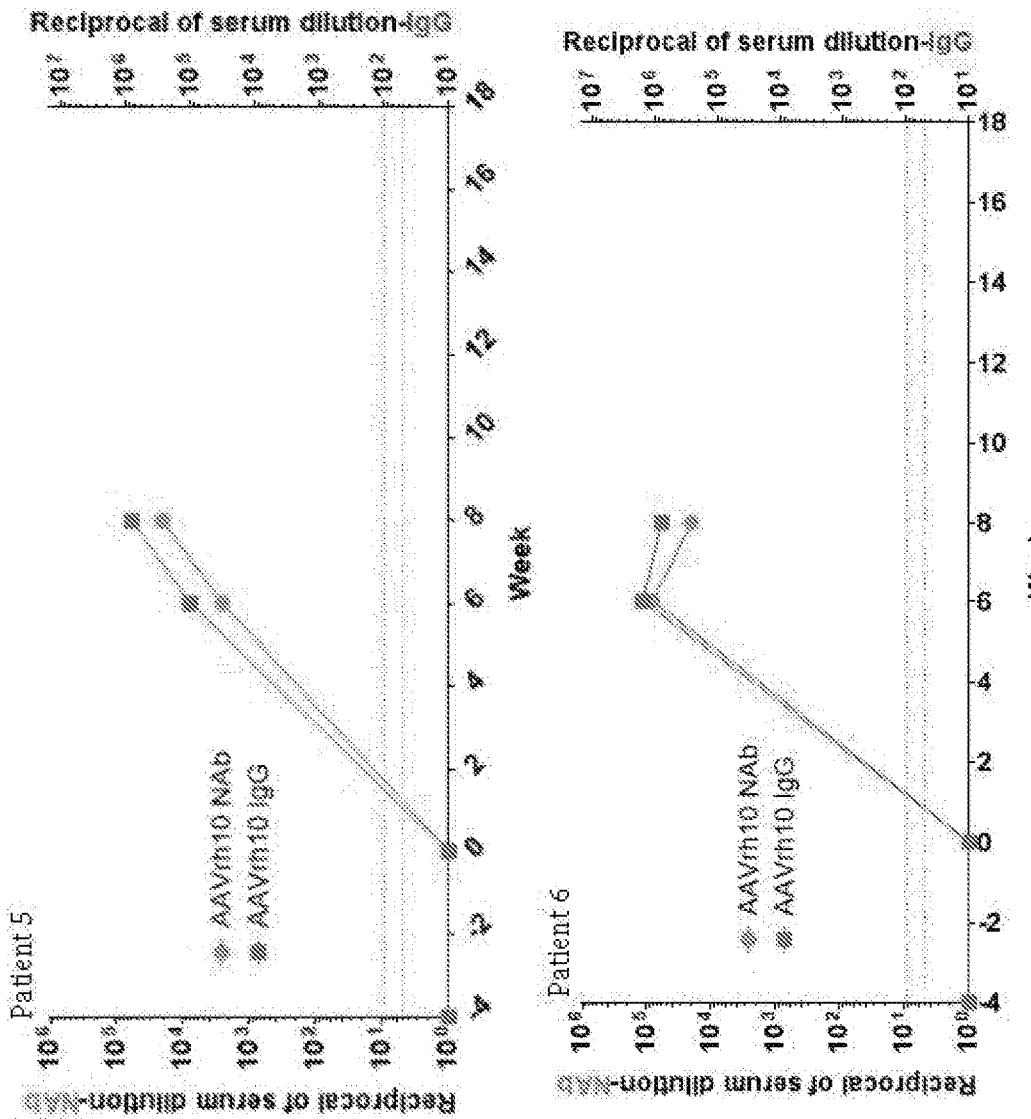

Intracellular cytokine staining (ICS) of CD4+ and CD8+ peripheral blood mononuclear cells (PBMCs) was performed at various time-points from six human patients making up the low- and mid-dose cohort of the trial discussed in the paragraph above. The graphs depict the percentage of CD4+ (FIG. 27A) and CD8+ (FIG. 27B) lymphocytes expressing lysosomal-associated membrane protein 1 (LAMP-1; CD107a), interferon-gamma (IFNγ), tumor necrosis factor alpha (TNFα), interleukin-2 (IL-2), or a combination as noted (IFNγ+TNFα). No substantial percentages of T cells were detected as expressing the cytokines described above in a PBMC culture stimulated with AAV (top panels of FIG. 27A and FIG. 27B) or Factor IX (bottom panels of FIG. 27A and FIG. 27B) except that Factor IX challenged PBMC of one patient collected on week 6 post treatment with medium dose of the AAV.hFIXco3T vector showed about 1% IL-2 positive CD4+ T cells of the total memory T cells. These results indicate that memory T cells recognizing AAV or Factor IX were not induced and generated after administering AAV.hFIXco3T at both dosages thus no obvious immunogenicity was observed.

Figure 29:
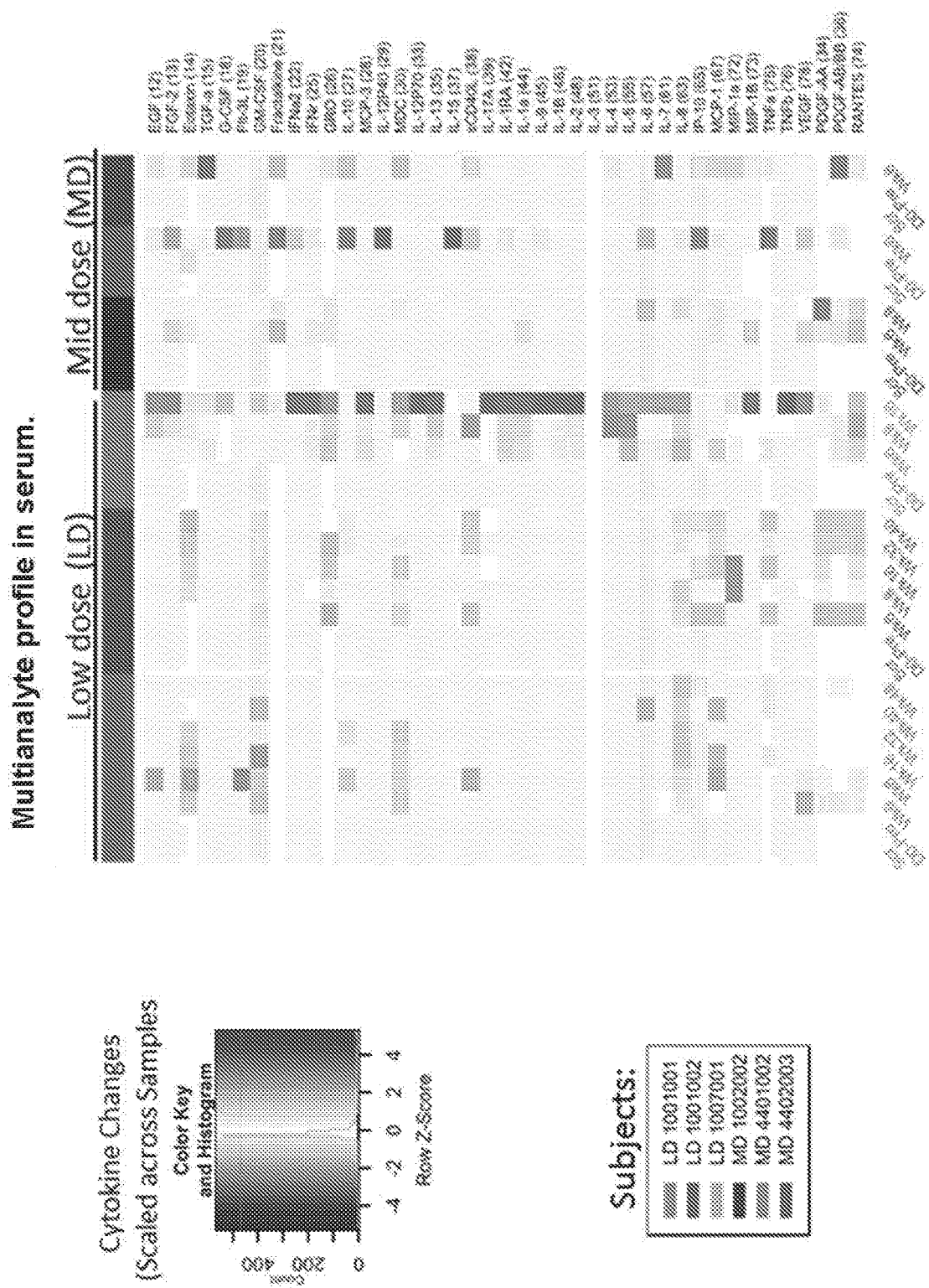
FIG. 29 is a heatmap showing the multianalye profile in the serum of six patients receiving the low- or mid-dose of the vector discussed for FIGS. 27A and B. Any analyte showing an increase in activity was coded in red while decreases were coded in blue.

Patients from the low- and mid-dose cohort were screened prior to and after AAV vector administration for neutralizing antibodies (NAbs) and Immunoglobulin-G (IgG) responses to the AAV capsid of interest (AAVrh.10) from isolated serum. All subjects except for one (Subject #3) showed NAbs below the limit of detection on the day of AAV vector administration (Day 0). All results are reported as the reciprocal of serum dilution. Serum from the same patients were analyzed using a Luminex multiplex system that allowed simultaneous testing against 41 different analytes linked with inflammation. The resulting data was plotted as a heatmap. Any analyte showing an increase in activity was coded in red while decreases were coded in blue in FIG. 29. The NAb titer of the six patients is shown below in Table 6.

TABLE 6

| | Dose | | | | | |
|---|---|---|---|---|---|---|
| | Low | | | High | | |
| | Subject | | | | | |
| | 1 | 2 | 3 | 4 | 5 | 6 |
| AAVrh10 Nab | <5 | <5 | 10 | <5 | <5 | <5 |

Each subject's mutation and MHC Class I binding prediction was examined for any unique indicators. Each subject's mutation is denoted by a bolded letter in the FIX amino acid sequence. Only 5 mutations are noted because Subject#1007001's mutation is a non-coding mutation (FIG. 30A). Using prediction software, the MHC Class I binding affinity to various alleles was predicted (FIG. 30B).

TABLE 7

| Subject Number (XXXXXXX) | Study Visit (Day or Week) | Medium (SFU/1E+6 PBMCs) | AAVrh.10 Pool A (SFU/1E+6 PBMCs) | AAVrh.10 Pool B (SFU/1E+6 PBMCs) | AAVrh.10 Pool C (SFU/1E+6 PBMCs) | FIX Pool A (SFU/1E+6 PBMCs) | FIX Pool B (SFU/1E+6 PBMCs) |
|---|---|---|---|---|---|---|---|
| 1001001 | Day 0 Predose | 10 | 18 | 13 | 23 | 13 | 10 |
| 1001001 | Week 16 | 0 | 5 | 5 | 3 | 8 | 3 |
| 1001001 | Week 6 | 5 | 0 | 3 | 5 | 0 | 8 |
| 1001001 | Week 8 | 0 | 5 | 0 | 0 | 3 | 13 |
| 1001001 | Week 32 | 3 | 0 | 8 | 3 | 23 | 3 |
| 1001001 | Week 40 | 25 | 43 | 33 | 33 | 60 | 50 |
| 1001001 | Week 48 | 10 | 5 | 13 | 20 | 10 | 10 |
| 1001002 | Day 0 Predose | 5 | 8 | 5 | 0 | 5 | 10 |
| 1001002 | Week 6 | 13 | 10 | 18 | 81 | 3 | 3 |
| 1001002 | Week 8 | 1 | 3 | 10 | 8 | 0 | 3 |
| 1001002 | Week 16 | 0 | 0 | 5 | 0 | 3 | 3 |
| 1001002 | Week 32 | 73 | 80 | 108 | 120 | 33 | 23 |
| 1001002 | Week 40 | 8 | 23 | 13 | 20 | 13 | 15 |
| 1002002 | Day 0 Predose | 125 | 170 | 168 | 153 | 170 | 145 |
| 1002002 | Week 6 | 25 | 38 | 53 | 20 | 20 | 33 |
| 1002002 | Week 8 | 23 | 33 | 83* | 73* | 18 | 45 |
| 1007001 | Day 0 Predose | 35 | 38 | 43 | 45 | 50 | 55 |
| 1007001 | Week 6 | 8 | 38 | 50* | 63* | 28 | 18 |
| 1007001 | Week 8 | 15 | 15 | 25 | 38 | 20 | 28 |
| 1007001 | Week 16 | 13 | 15 | 15 | 25 | 25 | 10 |
| 4401002 | Day 0 Predose | 23 | 18 | 55 | 15 | 23 | 50 |
| 4401002 | Week 6 | 15 | 40 | 133* | 143* | 13 | 25 |
| 4401002 | Week 8 | 8 | 35 | 60* | 85* | 28 | 20 |
| 4401002 | Week 12 | 0 | 3 | 13 | 10 | 8 | 3 |
| 4402003 | Day 0 Predose | | | PBMC Isolation Unsuccessful | | | |
| 4402003 | Week 6 | 3 | 43 | 25 | 28 | 0 | 3 |

Bold* = Positive Response to Specific Peptide Pool
Positive Results must meet 2 criteria - 1) >40 SFU/1E+6 PBMCs & 2) At least 3 times the Negative Control (Medium; Column C).

Sequence Listing Free Text

The following information is provided for sequences containing free text under numeric identifier <223>.

| SEQ ID NO: (containing free text) | Free text under <223> |
|---|---|
| 2 | <223> constructed sequence |
| 3 | <223> constructed sequence |
| 4 | <223> constructed sequence |
| 5 | <223> constructed sequence |
| 6 | <223> constructed sequence |
| 7 | <223> constructed sequence |
| 8 | <223> constructed sequence |
| 9 | <223> constructed sequence |
| 11 | <223> constructed sequence |
| 12 | <223> constructed sequence |
| 13 | <223> constructed sequence |
| 14 | <223> AAVrh.10 capsid |
| 15 | <223> constructed sequence |
| 16 | <223> constructed sequence |
| 17 | <223> constructed sequence |

All publications cited in this specification are incorporated herein by reference. Similarly, the SEQ ID NOs which are referenced herein and which appear in the appended Sequence Listing are incorporated by reference. Also incorporated by reference are U.S. Provisional Patent Application No. 62/323,375, filed Apr. 15, 2016, U.S. Provisional Patent Application No. 62/331,064, filed May 3, 2016, and U.S. Provisional Patent Application No. 62/428,804, filed Dec. 1, 2016. While the invention has been described with reference to particular embodiments, it will be appreciated that modifications can be made without departing from the spirit of the invention. Such modifications are intended to fall within the scope of the appended claims.

The invention claimed is:

1. A recombinant adeno-associated virus (rAAV) useful as a liver-directed therapeutic for hemophilia B, said rAAV comprising an AAVrh10 capsid and a vector genome packaged therein, said vector genome comprising:
    (a) an AAV 5' inverted terminal repeat (ITR) sequence;
    (b) a coding sequence encoding a human Factor IX (F9) having coagulation function operably linked to regulatory elements which direct expression of the human Factor IX protein in liver cells, wherein the coding sequence is SEQ ID NO: 2, and wherein the regulatory elements comprise (i) two copies of an alpha-1 microglobulin/bikuin enhancer and (ii) a thyroid hormone binding globulin (TBG) promoter; and;
    (c) an AAV 3' ITR.

2. The rAAV according to claim 1, wherein the encoded human Factor IX is the full-length protein about 461 amino acid residues in length.

3. The rAAV according to claim 1, wherein the encoded human Factor IX comprises SEQ ID NO: 10.

4. The rAAV according to claim 1, wherein the regulatory elements further comprise an intron.

5. The rAAV according to claim 4, wherein the intron is a human beta globin IVS2 intron.

6. The rAAV according to claim 1, wherein the regulatory elements further comprise a post-translational regulatory element and a polyA.

7. The rAAV according to claim 6, wherein the post-translational regulatory element is a woodchuck post-transcriptional regulatory element.

8. The rAAV according to claim 6, wherein the polyA is a bovine growth hormone polyA.

9. The rAAV according to claim 1, wherein the AAV 5' ITR and/or AAV3' ITR is from AAV2.

10. The rAAV according to claim 1, wherein the vector genome is about 4000 kilobases to about 4700 kilobases in size.

11. An aqueous suspension suitable for administration to a hemophilia B patient, said suspension comprising an aqueous suspending liquid and about $1 \times 10^{12}$ to about $3 \times 10^{13}$ genome copies (GC) of the rAAV/mL, wherein the GC are calculated as determined by optimized quantitative PCR (oqPCR), of a recombinant adeno-associated virus (rAAV) according to claim 1.

12. The suspension according to claim 11, wherein the suspension is suitable for intravenous injection.

13. The suspension according to claim 11, wherein the suspension further comprises a surfactant, preservative, and/or buffer dissolved in the aqueous suspending liquid.

14. The suspension according to claim 11, wherein the suspension comprises a non-ionic surfactant, a buffer solution, and has a pH of about 7 to about 8.

15. The suspension according to claim 14, wherein the surfactant is a poloxomer.

16. The rAAV according to claim 1, wherein the vector genome comprises nucleotides 1-3951 of SEQ ID NO:11.

17. The rAAV according to according to claim 1, wherein:
    the alpha-1 microglobulin/bikuin enhancer is SEQ ID NO:4; and
    the thyroid hormone binding globulin promoter is SEQ ID NO:5.

18. The rAAV according to claim 17, wherein the AAV 5' ITR is SEQ ID NO:3, and the AAV 3' ITR is SEQ ID NO:9.

19. The rAAV according to claim 1, wherein the regulatory elements further comprise an intron of SEQ ID NO:6.

20. The rAAV according to claim 1, wherein the regulatory elements further comprise a woodchuck post-transcriptional regulatory element of SEQ ID NO: 7.

21. The rAAV according to claim 1, wherein the regulatory elements further comprising a polyA sequence of SEQ ID NO:8.

* * * * *

SEQUENCE LISTING

<160> NUMBER OF SEQ ID NOS: 19

<210> SEQ ID NO 1
<211> LENGTH: 2802
<212> TYPE: DNA
<213> ORGANISM: Homo sapiens

<400> SEQUENCE: 1
accactttca caatctgcta gcaaaggtta tgcagcgcgt gaacatgatc atggcagaat    60
caccaggcct catcaccatc tgccttttag gatatctact cagtgctgaa tgtacagttt   120

```
ttcttgatca tgaaaacgcc aacaaaattc tgaatcggcc aaagaggtat aattcaggta      180
aattggaaga gtttgttcaa gggaaccttg agagagaatg tatggaagaa aagtgtagtt      240
ttgaagaagc acgagaagtt tttgaaaaca ctgaaagaac aactgaattt tggaagcagt      300
atgttgatgg agatcagtgt gagtccaatc catgttttaaa tggcggcagt tgcaaggatg     360
acattaattc ctatgaatgt tggtgtccct ttggatttga aggaaagaac tgtgaattag      420
atgtaacatg taacattaag aatggcagat gcgagcagtt ttgtaaaaat agtgctgata      480
acaaggtggt ttgctcctgt actgagggat atcgacttgc agaaaccag aagtcctgtg       540 aaccagcagt gccatttcca tgtggaagag tttctgtttc acaaacttct aagctcaccc      600
gtgctgagac tgtttttcct gatgtggact atgtaaattc tactgaagct gaaaccattt      660
tggataacat cactcaaagc acccaatcat ttaatgactt cactcgggtt gttggtggag      720
aagatgccaa accaggtcaa ttcccttggc aggttgtttt gaatggtaaa gttgatgcat      780
tctgtggagg ctctatcgtt aatgaaaaat ggattgtaac tgctgcccac tgtgttgaaa      840
ctggtgttaa aattacagtt gtcgcaggtg aacataatat tgaggagaca gaacatacag      900
agcaaaagcg aaatgtgatt cgaattattc ctcaccacaa ctacaatgca gctattaata      960
agtacaacca tgacattgcc cttctggaac tggacgaacc cttagtgcta aacagctacg     1020
ttacacctat ttgcattgct gacaaggaat acacgaacat cttcctcaaa tttggatctg     1080
gctatgtaag tggctgggga agagtcttcc acaaagggag atcagcttta gttcttcagt     1140
accttagagt tccacttgtt gaccgagcca catgtcttcg atctacaaag ttcaccatct     1200
ataacaacat gttctgtgct ggcttccatg aaggaggtag agattcatgt caaggagata     1260
gtgggggacc ccatgttact gaagtggaag ggaccagttt cttaactgga attattagct     1320
ggggtgaaga gtgtgcaatg aaaggcaaat atggaatata taccaaggta tcccggtatg     1380
tcaactggat taaggaaaaa acaaagctca cttaatgaaa gatggatttc caaggttaat     1440
tcattggaat tgaaaattaa cagggcctct cactaactaa tcactttccc atctttttgtt    1500 agatttgaat atatacattc tatgatcatt gcttttttctc tttacagggg agaatttcat    1560
attttacctg agcaaattga ttagaaaatg gaaccactag aggaatataa tgtgttagga     1620
aattacagtc atttctaagg gcccagccct tgacaaaatt gtgaagttaa attctccact     1680
ctgtccatca gatactatgg ttctccacta tggcaactaa ctcactcaat tttccctcct     1740
tagcagcatt ccatcttccc gatcttcttt gcttctccaa ccaaaacatc aatgtttatt     1800
agttctgtat acagtacagg atctttggtc tactctatca caaggccagt accacactca     1860
tgaagaaaga acacaggagt agctgagagg ctaaaactca tcaaaaacac tactcctttt     1920
cctctaccct attcctcaat cttttacctt ttccaaatcc caatcccaa atcagttttt      1980 ctctttctta ctccctctct cccttttacc ctccatggtc gttaaaggag atgggggag      2040 catcattctg ttatacttct gtacacagtt atacatgtct atcaaaccca gacttgcttc     2100
cgtagtggag acttgctttt cagaacatag ggatgaagta aggtgcctga aaagtttggg     2160
ggaaaagttt ctttcagaga gttaagttat tttatatata taatatatat ataaaatata    2220
taatatacaa tataaatata tagtgtgtgt gtatgcgtgt gtgtagacac acacgcatac     2280
acacatataa tggaagcaat aagccattct aagagcttgt atggttatgg aggtctgact    2340
aggcatgatt tcacgaaggc aagattggca tatcattgta actaaaaaag ctgacattga    2400
cccagacata ttgtactctt tctaaaaata ataataataa tgctaacaga aagaagagaa    2460
ccgttcgttt gcaatctaca gctagtagag actttgagga agaattcaac agtgtgtctt   2520
```

```
cagcagtgtt cagagccaag caagaagttg aagttgccta gaccagagga cataagtatc    2580
atgtctcctt taactagcat accccgaagt ggagaagggt gcagcaggct caaaggcata    2640
agtcattcca atcagccaac taagttgtcc ttttctggtt tcgtgttcac catggaacat    2700
tttgattata gttaatcctt ctatcttgaa tcttctagag agttgctgac caactgacgt    2760
atgtttccct tgtgaatta ataaactggt gttctggttc at                        2802
```

<210> SEQ ID NO 2
<211> LENGTH: 1386
<212> TYPE: DNA
<213> ORGANISM: Artificial Sequence
<220> FEATURE:
<223> OTHER INFORMATION: constructed sequence

<400> SEQUENCE: 2

```
atgcagcgcg tgaacatgat tatggccgag agccctggcc tgatcaccat ctgcctgctg      60
ggctacctgc tgagcgccga gtgcaccgtg tttctggacc acgagaacgc caacaagatc    120
ctgaaccggc ccaagcggta aacagcggc aagctggaag agttcgtgca gggcaacctg    180
gaacgcgagt gcatggaaga gaagtgcagc ttcgaagagg ccagagaggt gttcgagaac    240
accgagcgga ccaccgagtt ctggaagcag tacgtggacg gcgaccagtg cgagagcaac    300
ccctgtctga cggcggcag ctgcaaggac gacatcaaca gctacgagtg ctggtgcccc    360
ttcggcttcg agggcaagaa ctgcgagctg gacgtgacct gcaacatcaa gaacggcagg    420
tgcgagcagt tctgcaagaa cagcgccgac aacaaggtcg tgtgctcctg caccgagggc    480
tacagactgg ccgagaacca gaagtcctgc gagcccgccg tgcctttccc ttgtggaaga    540
gtgtccgtgt cccagaccag caagctgacc agagccgaga cagtgttccc cgacgtggac    600
tacgtgaaca gcaccgaggc cgagacaatc ctggacaaca tcacccagag cacccagtcc    660
ttcaacgact tcaccagagt cgtgggcggc gaggacgcca agcctggaca gttcccctgg    720
caggtggtgc tgaacggaaa ggtggacgcc ttttgcggcg gcagcatcgt gaacgagaag    780
tggatcgtga cagccgccca ctgcgtggaa accggcgtga agattacagt ggtggccggc    840
gagcacaaca tcgaggaaac cgagcacaca gagcagaaac ggaacgtgat cagaatcatc    900
ccccaccaca actacaacgc cgccatcaac aagtacaacc acgatatcgc cctgctggaa    960
ctggacgagc ccctggtgct gaatagctac gtgacccca tctgtatcgc cgacaaagag    1020
tacaccaaca tctttctgaa gttcggcagc ggctacgtgt ccggctgggg cagagtgttt    1080
cacaagggca gatccgctct ggtgctgcag tacctgagag tgcctctggt ggaccgggcc    1140
acctgtctga aagcaccaa gttcaccatc tacaacaaca tgttctgcgc cggcttccac    1200
gagggcggca gagatagctg tcagggcgat tctggcggcc ctcacgtgac agaggtggaa    1260
ggcaccagct ttctgaccgg catcatcagc tggggcgagg agtgcgccat gaaggggaag    1320
tacggcatct acaccaaggt gtccagatac gtgaactgga tcaaagaaaa gaccaagctg    1380
acatga                                                                1386
```

<210> SEQ ID NO 3
<211> LENGTH: 168
<212> TYPE: DNA
<213> ORGANISM: Artificial Sequence
<220> FEATURE:
<223> OTHER INFORMATION: constructed sequence

<400> SEQUENCE: 3

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120 agggggttcct tgtagttaat gattaacccg ccatgctact tatctacg               168
```

```
<210> SEQ ID NO 4
<211> LENGTH: 106
<212> TYPE: DNA
<213> ORGANISM: Artificial Sequence
<220> FEATURE:
<223> OTHER INFORMATION: constructed sequence

<400> SEQUENCE: 4
agttaatttt taaaaagcag tcaaaagtcc aagtgcccct gcgagcattt actctctctg    60
tttgctctgg ttaataatct caggagcaca aacattcctt actagt                  106
```

```
<210> SEQ ID NO 5
<211> LENGTH: 496
<212> TYPE: DNA
<213> ORGANISM: Artificial Sequence
<220> FEATURE:
<223> OTHER INFORMATION: constructed sequence

<400> SEQUENCE: 5
ccagtgtgct ggaattcggc ttttttaggg ctggaagcta cctttgacat catttcctct    60
gcgaatgcat gtataatttc tacagaacct attagaaagg atcacccagc ctctgctttt   120
gtacaacttt cccttaaaaa actgccaatc ccactgctgt ttggcccaat agtgagaact   180
ttttcctgct gcctcttggt gcttttgcct atggccccta ttctgcctgc tgaagacact   240
cttgccagca tggacttaaa cccctccagc tctgacaatc ctctttctct tttgttttac   300
atgaagggtc tggcagccaa agcaatcact caaagttcaa accttatcat tttttgcttt   360
gttcctcttg gccttggttt tgtacatcag ctttgaaaat accatcccag ggttaatgct   420
ggggttaatt tataactgag agtgctctag ttctgcaata caggacatgc tataaaaatg   480
gaaagatgtt gctttc                                                    496
```

```
<210> SEQ ID NO 6
<211> LENGTH: 572
<212> TYPE: DNA
<213> ORGANISM: Artificial Sequence
<220> FEATURE:
<223> OTHER INFORMATION: constructed sequence

<400> SEQUENCE: 6
agcttacttg tggtaccgag ctcggatcct gagaacttca gggtgagtct atgggaccct    60
tgatgttttc tttcccct tc ttttctatgg ttaagttcat gtcataggaa ggggagaagt   120
aacagggtac acatattgac caaatcaggg taattttgca tttgtaattt taaaaaatgc   180
tttcttcttt taatatactt ttttgtttat cttatttcta atactttccc taatctcttt   240
ctttcagggc aataatgata caatgtatca tgcctctttg caccattcta aagaataaca   300
gtgataattt ctgggttaag gcaatagcaa tatttctgca tataaatatt tctgcatata   360
aattgtaact gatgtaagag gtttcatatt gctaatagca gctacaatcc agctaccatt   420
ctgcttttat tttatggttg ggataaggct ggattattct gagtccaagc taggcccttt   480
tgctaatcat gttcatacct cttatcttcc tcccacagct cctgggcaac gtgctggtct   540
gtgtgctggc ccatcacttt ggcaaagaat tg                                 572
```

-continued

<210> SEQ ID NO 7
<211> LENGTH: 542
<212> TYPE: DNA
<213> ORGANISM: Artificial Sequence
<220> FEATURE:
<223> OTHER INFORMATION: constructed sequence

<400> SEQUENCE: 7

```
aatcaacctc tggattacaa aatttgtgaa agattgactg gtattcttaa ctatgttgct      60
cctttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact      240
ggttggggca ttgccaccac ctgtcagctc ctttccggga cttcgctttt ccccctccct     300
attgccacgg cggaactcat cgccgcctgc cttgcccgct gctggacagg ggctcggctg     360
ttgggcactg acaattccgt ggtgttgtcg gggaaatcat cgtcctttcc ttggctgctc     420
gcctgtgttg ccacctggat tctgcgcggg acgtccttct gctacgtccc ttcggccctc     480
aatccagcgg accttccttc ccgcggcctg ctgccggctc tgcggcctct ccgcgtctt     540
cg                                                                   542
```

<210> SEQ ID NO 8
<211> LENGTH: 215
<212> TYPE: DNA
<213> ORGANISM: Artificial Sequence
<220> FEATURE:
<223> OTHER INFORMATION: constructed sequence

<400> SEQUENCE: 8

```
gcctcgactg tgccttctag ttgccagcca tctgttgttt gccctccc cgtgccttcc       60
ttgaccctgg aaggtgccac tcccactgtc cttttcctaat aaaatgagga aattgcatcg   120
cattgtctga gtaggtgtca ttctattctg gggggtgggg tggggcagga cagcaagggg    180
gaggattggg aagacaatag caggcatgct gggga                                215
```

<210> SEQ ID NO 9
<211> LENGTH: 168
<212> TYPE: DNA
<213> ORGANISM: Artificial Sequence
<220> FEATURE:
<223> OTHER INFORMATION: constructed sequence

<400> SEQUENCE: 9

```
cgtagataag tagcatggcg ggttaatcat taactacaag gaaccctag tgatggagtt       60
ggccactccc tctctgcgcg ctcgctcgct cactgaggcc gggcgaccaa aggtcgcccg    120
acgcccgggc tttgcccggg cggcctcagt gagcgagcga gcgcgcag                  168
```

<210> SEQ ID NO 10
<211> LENGTH: 461
<212> TYPE: PRT
<213> ORGANISM: Homo sapiens

<400> SEQUENCE: 10

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

```
Ser Gly Lys Leu Glu Glu Phe Val Gln Gly Asn Leu Glu Arg Glu Cys
 50                  55                  60
Met Glu Glu Lys Cys Ser Phe Glu Glu Ala Arg Glu Val Phe Glu Asn
 65                  70                  75                  80
Thr Glu Arg Thr Thr Glu Phe Trp Lys Gln Tyr Val Asp Gly Asp Gln
                 85                  90                  95
Cys Glu Ser Asn Pro Cys Leu Asn Gly Gly Ser Cys Lys Asp Asp Ile
                100                 105                 110
Asn Ser Tyr Glu Cys Trp Cys Pro Phe Gly Phe Glu Gly Lys Asn Cys
            115                 120                 125
Glu Leu Asp Val Thr Cys Asn Ile Lys Asn Gly Arg Cys Glu Gln Phe
        130                 135                 140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
                180                 185                 190
Glu Thr Val Phe Pro Asp Val Asp Tyr Val Asn Ser Thr Glu Ala Glu
            195                 200                 205
Thr Ile Leu Asp Asn Ile Thr Gln Ser Thr Gln Ser Phe Asn Asp Phe
210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
                260                 265                 270
Val Lys Ile Thr Val Val Ala Gly Glu His Asn Ile Glu Glu Thr Glu
            275                 280                 285
His Thr Glu Gln Lys Arg Asn Val Ile Arg Ile Ile Pro His His Asn
        290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
                340                 345                 350
Val Ser Gly Trp Gly Arg Val Phe His Lys Gly Arg Ser Ala Leu Val
            355                 360                 365
Leu Gln Tyr Leu Arg Val Pro Leu Val Asp Arg Ala Thr Cys Leu Arg
        370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr
450                 455                 460
```

<210> SEQ ID NO 11
<211> LENGTH: 7209
<212> TYPE: DNA
<213> ORGANISM: Artificial Sequence
<220> FEATURE:
<223> OTHER INFORMATION: constructed sequence

<400> SEQUENCE: 11

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gccatgctct | 180 |
| aggaagatcg gaattcgccc ttaagctagg ggggatccac tagtactcga gacctaggag | 240 |
| ttaattttta aaaagcagtc aaaagtccaa gtgcccttgc gagcatttac tctctctgtt | 300 |
| tgctctggtt aataatctca ggagcacaaa cattccttac tagttctagg agttaatttt | 360 |
| taaaaagcag tcaaaagtcc aagtgccctt gcgagcattt actctctctg tttgctctgg | 420 |
| ttaataatct caggagcaca acattcctt actagttcta gagcggccgc cagtgtgctg | 480 |
| gaattcggct tttttagggc tggaagctac ctttgacatc atttcctctg cgaatgcatg | 540 |
| tataatttct acagaaccta ttagaaagga tcacccagcc tctgcttttg tacaactttc | 600 |
| ccttaaaaaa ctgccaatcc cactgctgtt tggcccaata gtgagaactt tttcctgctg | 660 |
| cctcttggtg cttttgccta tggcccctat tctgcctgct gaagacactc ttgccagcat | 720 |
| ggacttaaac ccctccagct ctgacaatcc tctttctctt ttgttttaca tgaagggtct | 780 |
| ggcagccaaa gcaatcactc aaagttcaaa ccttatcatt ttttgctttg ttcctcttgg | 840 |
| ccttggtttt gtacatcagc tttgaaaata ccatcccagg gttaatgctg gggttaattt | 900 |
| ataactgaga gtgctctagt tctgcaatac aggacatgct ataaaaatgg aaagatgttg | 960 |
| ctttctgaga gatcagctta catgtggtac cgagctcgga tcctgagaac ttcagggtga | 1020 |
| gtctatggga cccttgatgt tttctttccc cttcttttct atggttaagt tcatgtcata | 1080 |
| ggaaggggag aagtaacagg gtacacatat tgaccaaatc agggtaattt tgcatttgta | 1140 |
| attttaaaaa atgctttctt cttttaatat acttttttgt ttatcttatt tctaatactt | 1200 |
| tccctaatct ctttctttca gggcaataat gatacaatgt atcatgcctc tttgcaccat | 1260 |
| tctaaagaat aacagtgata atttctgggt taaggcaata gcaatatttc tgcatataaa | 1320 |
| tatttctgca tataaattgt aactgatgta agaggtttca tattgctaat agcagctaca | 1380 |
| atccagctac cattctgctt ttattttatg gttgggataa ggctggatta ttctgagtcc | 1440 |
| aagctaggcc cttttgctaa tcatgttcat acctcttatc ttcctcccac agctcctggg | 1500 |
| caacgtgctg gtctgtgtgc tggcccatca ctttggcaaa gaattgatct cgagtaactg | 1560 |
| agccgccacc atgcagcgcg tgaacatgat tatggccgag agccctggcc tgatcaccat | 1620 |
| ctgcctgctg ggctacctgc tgagcgccga gtgcaccgtg tttctggacc acgaaacgc | 1680 |
| caacaagatc ctgaaccggc ccaagcgta caacagcgg aagctggaag agttcgtgca | 1740 |
| gggcaacctg gaacgcgagt gcatggaaga aagtgcagc ttcgaagagg ccagagaggt | 1800 |
| gttcgagaac accagcgga ccaccgagtt ctggaagcag tacgtggacg gcgaccagtg | 1860 |
| cgagagcaac ccctgtctga acggcggcag ctgcaaggac gacatcaaca gctacgagtg | 1920 |
| ctggtgcccc ttcggcttcg agggcaagaa ctgcgagctg gacgtgacct gcaacatcaa | 1980 |
| gaacggcagg tgcgagcagt tctgcaagaa cagcgccgac aacaaggtcg tgtgctcctg | 2040 |
| caccgagggc tacagactgg ccgagaacca gaagtcctgc gagcccgccg tgccttttcc | 2100 |

```
ttgtggaaga gtgtccgtgt cccagaccag caagctgacc agagccgaga cagtgttccc    2160
cgacgtggac tacgtgaaca gcaccgaggc cgagacaatc ctggacaaca tcacccagag    2220
cacccagtcc ttcaacgact tcaccagagt cgtgggcggc gaggacgcca agcctggaca    2280
gttcccctgg caggtggtgc tgaacggaaa ggtggacgcc ttttgcggcg gcagcatcgt    2340
gaacgagaag tggatcgtga cagccgccca ctgcgtggaa accggcgtga agattacagt    2400
ggtggccggc gagcacaaca tcgaggaaac cgagcacaca gagcagaaac ggaacgtgat    2460
cagaatcatc ccccaccaca actacaacgc cgccatcaac aagtacaacc acgatatcgc    2520
cctgctggaa ctggacgagc ccctggtgct gaatagctac gtgaccccca tctgtatcgc    2580
cgacaaagag tacaccaaca tctttctgaa gttcggcagc ggctacgtgt ccggctgggg    2640
cagagtgttt cacaagggca gatccgctct ggtgctgcag tacctgagag tgcctctggt    2700
ggaccgggcc acctgtctga aagcaccaag gttcaccatc tacaacaaca tgttctgcgc    2760
cggcttttac gagggcggca gagatagctg tcagggcgat tctggcggcc ctcacgtgac    2820
agaggtggaa ggcaccagct ttctgaccgg catcatcagc tggggcgagg agtgcgccat    2880
gaaggggaag tacggcatct acaccaaggt gtccagatac gtgaactgga tcaaagaaaa    2940
gaccaagctg acatgataaa agcttggatc caatcaacct ctggattaca aaatttgtga    3000
aagattgact ggtattctta actatgttgc tccttttacg ctatgtggat acgctgcttt    3060
aatgcctttg tatcatgcta ttgcttcccg tatggctttc attttctcct ccttgtataa    3120
atcctggttg ctgtctcttt atgaggagtt gtggcccgtt gtcaggcaac gtggcgtggt    3180
gtgcactgtg tttgctgacg caaccccccac tggttgggc attgccacca cctgtcagct    3240
cctttccggg actttcgctt tccccctccc tattgccacg gcggaactca tcgccgcctg    3300
ccttgcccgc tgctggacag gggctcggct gttgggcact gacaattccg tggtgttgtc    3360
ggggaaatca tcgtcctttc cttggctgct cgcctgtgtt gccacctgga ttctgcgcgg    3420
gacgtccttc tgctacgtcc cttcggccct caatccagcg gaccttcctt cccgcggcct    3480
gctgccggct ctgcggcctc ttccgcgtct tcgagatctg cctcgactgt gccttctagt    3540
tgccagccat ctgttgtttg ccccctcccc gtgccttcct tgaccctgga aggtgccact    3600
cccactgtcc tttcctaata aaatgaggaa attgcatcgc attgtctgag taggtgtcat    3660
tctattctgg ggggtggggt ggggcaggac agcaagggg aggattggga agacaatagc    3720
aggcatgctg gggactcgag ttaagggcga attcccgata aggatcttcc tagagcatgg    3780
ctacgtagat aagtagcatg gcgggttaat cattaactac aaggaacccc tagtgatgga    3840
gttggccact ccctctctgc gcgctcgctc gctcactgag gccgggcgac caaaggtcgc    3900
ccgacgcccg ggctttgccc gggcggcctc agtgagcgag cgagcgcgca gccttaatta    3960
acctaattca ctggccgtcg ttttacaacg tcgtgactgg gaaaaccctg gcgttaccca    4020
acttaatcgc cttgcagcac atccccctttt cgccagctgg cgtaatagcg aagaggcccg    4080
caccgatcgc ccttcccaac agttgcgcag cctgaatggc gaatgggacg cgccctgtag    4140
cggcgcatta gcgcggcgg gtgtggtggt tacgcgcagc gtgaccgcta cacttgccag    4200
cgccctagcg cccgctcctt tcgctttctt cccttccttt ctcgccacgt tcgccggctt    4260
tccccgtcaa gctctaaatc ggggggctccc tttagggttc cgatttagtg ctttacggca    4320
cctcgacccc aaaaaacttg attagggtga tggttcacgt agtgggccat cgccctgata    4380
gacggttttt cgccctttga cgttggagtc cacgttcttt aatagtggac tcttgttcca    4440
```

-continued

```
aactggaaca acactcaacc ctatctcggt ctattctttt gatttataag ggattttgcc    4500
gatttcggcc tattggttaa aaaatgagct gatttaacaa aaatttaacg cgaatttnaa    4560
caaaatcatg tgagcaaaag gccagcaaaa ggccaggaac cgtaaaaagg ccgcgttgct    4620
ggcgtttttc cataggctcc gcccccctga cgagcatcac aaaaatcgac gctcaagtca    4680
gaggtggcga aacccgacag gactataaag ataccaggcg tttccccctg gaagctccct    4740
cgtgcgctct cctgttccga ccctgccgct taccggatac ctgtccgcct ttctcccttc    4800
gggaagcgtg gcgctttctc atagctcacg ctgtaggtat ctcagttcgg tgtaggtcgt    4860
tcgctccaag ctgggctgtg tgcacgaacc ccccgttcag cccgaccgct gcgccttatc    4920
cggtaactat cgtcttgagt ccaacccggt aagacacgac ttatcgccac tggcagcagc    4980
cactggtaac aggattagca gagcgaggta tgtaggcggt gctacagagt tcttgaagtg    5040
gtggcctaac tacggctaca ctagaagaac agtatttggt atctgcgctc tgctgaagcc    5100
agttaccttc ggaaaaagag ttggtagctc ttgatccggc aaacaaacca ccgctggtag    5160
cggtggtttt tttgtttgca agcagcagat tacgcgcaga aaaaaggat ctcaagaaga    5220 tcctttgatc ttttctacgg ggtctgacgc tcagtggaac gaaaactcac gttaagggat    5280
tttggtcatg agattatcaa aaaggatctt cacctagatc cttttgatcc tccggcgttc    5340
agcctgtgcc acagccgaca ggatggtgac caccatttgc cccatatcac cgtcggtact    5400
gatcccgtcg tcaataaacc gaaccgctac accctgagca tcaaactctt ttatcagttg    5460
gatcatgtcg gcggtgtcgc ggccaagacg gtcgagcttc ttcaccagaa tgacatcacc    5520
ttcctccacc ttcatcctca gcaaatccag cccttcccga tctgttgaac tgccggatgc    5580
cttgtcggta aagatgcggt tagcttttac ccctgcatct ttgagcgctg aggtctgcct    5640
cgtgaagaag gtgttgctga ctcataccag gcctgaatcg ccccatcatc cagccagaaa    5700
gtgagggagc cacggttgat gagagctttg ttgtaggtgg accagttggt gattttgaac    5760
ttttgctttg ccacggaacg gtctgcgttg tcgggaagat gcgtgatctg atccttcaac    5820
tcagcaaaag ttcgatttat tcaacaaagc cgccgtcccg tcaagtcagc gtaatgctct    5880
gccagtgtta caaccaatta accaattctg attagaaaaa ctcatcgagc atcaaatgaa    5940
actgcaattt attcatatca ggattatcaa taccatattt ttgaaaaagc cgtttctgta    6000
atgaaggaga aaactcaccg aggcagttcc ataggatggc aagatcctgg tatcggtctg    6060
cgattccgac tcgtccaaca tcaatacaac ctattaattt cccctcgtca aaaataaggt    6120
tatcaagtga gaaatcacca tgagtgacga ctgaatccgg tgagaatggc aaaagcttat    6180
gcatttcttt ccagacttgt tcaacaggcc agccattacg ctcgtcatca aaatcactcg    6240
catcaaccaa accgttattc attcgtgatt gcgcctgagc gagacgaaat acgcgatcgc    6300
tgttaaaagg acaattacaa acaggaatcg aatgcaaccg gcgcaggaac actgccagcg    6360
catcaacaat attttcacct gaatcaggat attcttctaa tacctggaat gctgttttcc    6420
cggggatcgc agtggtgagt aaccatgcat catcaggagt acggataaaa tgcttgatgg    6480
tcggaagagg cataaattcc gtcagccagt ttagtctgac catctcatct gtaacatcat    6540
tggcaacgct acctttgcca tgtttcagaa acaactctgg cgcatcgggc ttcccataca    6600
atcgatagat tgtcgcacct gattgcccga cattatcgcg agcccattta tacccatata    6660
aatcagcatc catgttggaa tttaatcgcg gcctcgagca agacgtttcc cgttgaatat    6720
ggctcataac ccccttgta ttactgttta tgtaagcaga cagttttatt gttcatgatg    6780
atatattttt atcttgtgca atgtaacatc agagattttg agacaccatg ttctttcctg    6840
```

| cgttatcccc tgattctgtg gataaccgta ttaccgcctt tgagtgagct gataccgctc | 6900 |
| gccgcagccg aacgaccgag cgcagcgagt cagtgagcga ggaagcggaa gagcgcccaa | 6960 |
| tacgcaaacc gcctctcccc gcgcgttggc cgattcatta atgcagctgg cacgacaggt | 7020 |
| ttcccgactg gaaagcgggc agtgagcgca acgcaattaa tgtgagttag ctcactcatt | 7080 |
| aggcacccca ggctttacac tttatgcttc cggctcgtat gttgtgtgga attgtgagcg | 7140 |
| gataacaatt tcacacagga aacagctatg accatgatta cgccagattt aattaaggcc | 7200 |
| ttaattagg | 7209 |

<210> SEQ ID NO 12
<211> LENGTH: 7748
<212> TYPE: DNA
<213> ORGANISM: Artificial Sequence
<220> FEATURE:
<223> OTHER INFORMATION: constructed sequence

<400> SEQUENCE: 12

| cagcagctgc gcgctcgctc gctcactgag gccgcccggg caaagcccgg gcgtcgggcg | 60 |
| acctttggtc gcccggcctc agtgagcgag cgagcgcgca gagagggagt ggccaactcc | 120 |
| atcactaggg gttccttgta gttaatgatt aacccgccat gctacttatc tacgtagcca | 180 |
| tgctctagct aggcccgggg gatccactag tactcgagac ctaggagtta attttaaaa | 240 |
| agcagtcaaa agtccaagtg cccttgcgag catttactct ctctgtttgc tctggttaat | 300 |
| aatctcagga gcacaaacat tccttactag ttctaggagt taatttttaa aaagcagtca | 360 |
| aaagtccaag tgcccttgcg agcatttact ctctctgttt gctctggtta ataatctcag | 420 |
| gagcacaaac attccttact agttctagag cggccgccag tgtgctggaa ttcggctttt | 480 |
| ttagggctgg aagctaccct tgacatcatt tcctctgcga atgcatgtat aatttctaca | 540 |
| gaacctatta gaaaggatca cccagcctct gcttttgtac aactttccct taaaaaactg | 600 |
| ccaatcccac tgctgtttgg cccaatagtg agaactttt cctgctgcct cttggtgctt | 660 |
| ttgcctatgg cccctattct gcctgctgaa gacactcttg ccagcatgga cttaaacccc | 720 |
| tccagctctg acaatcctct ttctcttttg ttttacatga agggtctggc agccaaagca | 780 |
| atcactcaaa gttcaaacct tatcattttt tgctttgttc ctcttggcct tggttttgta | 840 |
| catcagcttt gaaaatacca tcccagggtt aatgctgggg ttaatttata actgagagtg | 900 |
| ctctagttct gcaatacagg acatgctata aaaatggaaa gatgttgctt tctgagagat | 960 |
| cagcttacat gtggtaccga gctcggatcc tgagaacttc agggtgagtc tatgggaccc | 1020 |
| ttgatgtttt ctttcccctt cttttctatg gttaagttca tgtcatagga aggggagaag | 1080 |
| taacagggta cacatattga ccaaatcagg gtaattttgc atttgtaatt ttaaaaaatg | 1140 |
| cttctcttct ttaatatact ttttgtttta tcttatttct aatactttcc ctaatctctt | 1200 |
| tctttcaggg caataatgat acaatgtatc atgcctcttt gcaccattct aaagaataac | 1260 |
| agtgataatt tctgggttaa ggcaatagca atatttctgc atataaatat ttctgcatat | 1320 |
| aaattgtaac tgatgtaaga ggtttcatat tgctaatagc agctacaatc cagctaccat | 1380 |
| tctgctttta ttttatggtt gggataaggc tggattattc tgagtccaag ctaggccctt | 1440 |
| ttgctaatca tgttcatacc tcttatcttc ctcccacagc tcctgggcaa cgtgctggtc | 1500 |
| tgtgtgctgg cccatcactt tggcaaagaa ttgatctcga gaaagctaac aacaaagaac | 1560 |
| aacaaacaac aatcaggata acaagaacga aacaataaca gccaccatgc agagggtgaa | 1620 |

```
catgatcatg gctgagagcc ctggcctgat caccatctgc ctgctgggct acctgctgtc    1680
tgctgagtgc actgtgttcc tggaccatga gaatgccaac aagatcctga acaggcccaa    1740
gagatacaac tctggcaagc tggaggagtt tgtgcagggc aacctggaga gggagtgcat    1800
ggaggagaag tgcagctttg aggaggccag ggaggtgttt gagaacactg agaggaccac    1860
tgagttctgg aagcagtatg tggatgggga ccagtgtgag agcaacccct gcctgaatgg    1920
gggcagctgc aaggatgaca tcaacagcta tgagtgctgg tgcccctttg ctttgagggg    1980
caagaactgt gagctggatg tgacctgcaa catcaagaat ggcagatgtg agcagttctg    2040
caagaactct gctgacaaca aggtggtgtg cagctgcact gagggctaca ggctggctga    2100
gaaccagaag agctgtgagc tgctgtgcc attcccatgt ggcagagtgt ctgtgagcca    2160
gaccagcaag ctgaccaggg ctgaggctgt gttccctgat gtggactatg tgaacagcac    2220
tgaggctgaa accatcctgg acaacatcac ccagagcacc cagagcttca atgacttcac    2280
cagggtggtg gggggggagg atgccaagcc tggccagttc ccctggcaag tggtgctgaa    2340
tggcaaggtg gatgccttct gtgggggcag cattgtgaat gagaagtgga ttgtgactgc    2400
tgcccactgt gtggagactg gggtgaagat cactgtggtg gctggggagc acaacattga    2460
ggagactgag cacactgagc agaagaggaa tgtgatcagg atcatccccc accacaacta    2520
caatgctgcc atcaacaagt acaaccatga cattgccctg ctggagctgg atgagcccct    2580
ggtgctgaac agctatgtga ccccccatctg cattgctgac aaggagtaca ccaacatctt    2640
cctgaagttt ggctctggct atgtgtctgg ctggggcagg gtgttccaca agggcaggtc    2700
tgccctggtg ctgcagtacc tgagggtgcc cctggtggac agggccacct gcctgaggag    2760
caccaagttc accatctaca caacacatgtt ctgtgctggc ttccatgagg ggggcaggga    2820
cagctgccag ggggactctg ggggccccca tgtgactgag gtgagggca ccagcttcct    2880 gactggcatc atcagctggg gggaggagtg tgccatgaag ggcaagtatg gcatctacac    2940
caaagtctcc agatatgtga actggatcaa ggagaagacc aagctgacct gaaataagct    3000
tatcgataat caacctctgg attacaaaat ttgtgaaaga ttgactggta ttcttaacta    3060
tgttgctcct tttacgctat gtggatacgc tgctttaatg cctttgtatc atgctattgc    3120
ttcccgtatg gctttcattt tctcctcctt gtataaatcc tggttgctgt ctctttatga    3180
ggagttgtgg cccgttgtca ggcaacgtgg cgtggtgtgc actgtgtttg ctgacgcaac    3240
ccccactggt tggggcattg ccaccacctg tcagctcctt tccgggactt tcgctttccc    3300
cctccctatt gccacggcgg aactcatcgc cgcctgcctt gcccgctgct ggacaggggc    3360
tcggctgttg ggcactgaca attccgtggt gttgtcgggg aaatcatcgt cctttccttg    3420
gctgctcgcc tgtgttgcca cctggattct gcgcgggacg tccttctgct acgtcccttc    3480
ggccctcaat ccagcggacc ttccttcccg cggcctgctg ccggctctgc ggcctcttcc    3540
gcgtcttcgc cttcgccctc agacgagtcg atctccctt gggccgcct cccgcatcg    3600 ataccgtcga cctcgaatcg aattcctgca gcccggggga tccactagtt ctagagcggc    3660
caaacccgct gatcagcctc gactgtgcct tctagttgcc agccatctgt tgtttgcccc    3720 tccccgtgc cttccttgac cctggaaggt gccactccca ctgtcctttc ctaataaaat    3780
gaggaaattg catcgcattg tctgagtagg tgtcattcta ttctgggggg tggggtgggg    3840
caggacagca agggggagga ttgggaagac aatagcaggc atgctgggga tcggtgggc    3900 tctatggctt ctgaggcgga aagaaccagg atcctagagc atggctacgt agataagtag    3960
catggcgggt taatcattaa ctacaaggaa cccctagtga tggagttggc cactccctct    4020
```

-continued

```
ctgcgcgctc gctcgctcac tgaggccggg cgaccaaagg tcgcccgacg cccgggcttt    4080
gcccgggcgg cctcagtgag cgagcgagcg cgcagctggc gtaatagcga agaggcccgc    4140
accgatcgcc cttcccaaca gttgcgcagc ctgaatggcg aatggaattc cagacgattg    4200
agcgtcaaaa tgtaggtatt tccatgacgc ttttttcctgt tgcaatggct ggcggtaata    4260
ttgttctgga tattaccagc aaggccgata gtttgagttc ttctactcag gcaagtgatg    4320
ttattactaa tcaaagaagt attgcgacaa cggttaattt gcgtgatgga cagactcttt    4380
tactcggtgg cctcactgat tataaaaaca cttctcagga ttctggcgta ccgttcctgt    4440
ctaaaatccc tttaatcggc ctcctgttta gctcccgctc tgattctaac gaggaaagca    4500
cgttatacgt gctcgtcaaa gcaaccatag tacgcgccct gtagcggcgc attaagcgcg    4560
gcgggtgtgg tggttacgcg cagcgtgacc gctacacttg ccagcgccct agcgcccgct    4620
cctttcgctt tcttcccttc ctttctcgcc acgttcgccg gctttccccg tcaagctcta    4680
aatcgggggc tccctttagg gttccgattt agtgctttac ggcacctcga cccccaaaaaa    4740 cttgattagg gtgatggttc acgtagtggg ccatcgccct gatagacggt ttttcgccct    4800
ttgacgttgg agtccacgtt ctttaatagt ggactcttgt tccaaactgg aacaacactc    4860
aaccctatct cggtctattc ttttgattta aagggatttt gccgatttc ggcctattgg    4920 ttaaaaaatg agctgattta acaaaaattt aacgcgaatt ttaacaaaat attaacgttt    4980
acaatttaaa tatttgctta tacaatcttc ctgttttttgg ggcttttctg attatcaacc    5040
ggggtacata tgattgacat gctagtttta cgattaccgt tcatcgattc tcttgtttgc    5100
tccagactct caggcaatga cctgatagcc tttgtagaga cctctcaaaa atagctaccc    5160
tctccggcat gaatttatca gctagaacgg ttgaatatca tattgatggt gatttgactg    5220
tctccggcct ttctcacccg tttgaatctt tacctacaca ttactcaggc attgcattta    5280
aaatatatga gggttctaaa aattttttatc cttgcgttga aataaaggct tctcccgcaa    5340
aagtattaca gggtcataat gtttttggta caaccgattt agctttatgc tctgaggctt    5400
tattgcttaa ttttgctaat tctttgcctt gcctgtatga tttattggat gttggaattc    5460
ctgatgcggt attttctcct tacgcatctg tgcggtattt cacaccgcat atggtgcact    5520
ctcagtacaa tctgctctga tgccgcatag ttaagccagc ccgacacccc gccaacaccc    5580
gctgacgcgc cctgacgggc ttgtctgctc ccggcatccg cttacagaca agctgtgacc    5640
gtctccggga gctgcatgtg tcagaggttt tcaccgtcat caccgaaacg cgcgagacga    5700
aagggcctcg tgatacgcct atttttatag gttaatgtca tgataataat ggtttcttag    5760
acgtcaggtg gcacttttcg gggaaatgtg cgcggaaccc ctatttgttt attttttctaa    5820 atacattcaa atatgtatcc gctcatgaga caataaccct gataaatgct tcaataatat    5880
tgaaaaagga agagtatgag tattcaacat ttccgtgtcg cccttattcc cttttttgcg    5940 gcatttttgcc ttcctgtttt tgctcaccca gaaacgctgg tgaaagtaaa agatgctgaa    6000
gatcagttgg gtgcacgagt gggttacatc gaactggatc tcaacagcgg taagatcctt    6060
gagagttttc gccccgaaga acgttttcca atgatgagca cttttaaagt tctgctatgt    6120
ggcgcggtat tatcccgtat tgacgccggg caagagcaac tcggtcgccg catacactat    6180
tctcagaatg acttggttga gtactcacca gtcacagaaa agcatcttac ggatggcatg    6240
acagtaagag aattatgcag tgctgccata accatgagtg ataacactgc ggccaactta    6300
cttctgacaa cgatcggagg accgaaggag ctaaccgctt ttttgcacaa catgggggat    6360
```

```
catgtaactc gccttgatcg ttgggaaccg gagctgaatg aagccatacc aaacgacgag    6420
cgtgacacca cgatgcctgt agcaatggca acaacgttgc gcaaactatt aactggcgaa    6480
ctacttactc tagcttcccg gcaacaatta atagactgga tggaggcgga taaagttgca    6540
ggaccacttc tgcgctcggc ccttccggct ggctggttta ttgctgataa atctggagcc    6600
ggtgagcgtg gtctcgcgg tatcattgca gcactggggc cagatggtaa gccctcccgt    6660
atcgtagtta tctacacgac ggggagtcag gcaactatgg atgaacgaaa tagacagatc    6720
gctgagatag gtgcctcact gattaagcat tggtaactgt cagaccaagt ttactcatat    6780
atactttaga ttgatttaaa acttcatttt taatttaaaa ggatctaggt gaagatcctt    6840
tttgataatc tcatgaccaa aatcccttaa cgtgagtttt cgttccactg agcgtcagac    6900
cccgtagaaa agatcaaagg atcttcttga gatccttttt ttctgcgcgt aatctgctgc    6960
ttgcaaacaa aaaaccacc gctaccagcg gtggtttgtt tgccggatca agagctacca    7020
actctttttc cgaaggtaac tggcttcagc agagcgcaga taccaaatac tgtccttcta    7080
gtgtagccgt agttaggcca ccacttcaag aactctgtag caccgcctac atacctcgct    7140
ctgctaatcc tgttaccagt ggctgctgcc agtggcgata gtcgtgtct taccgggttg    7200 gactcaagac gatagttacc ggataaggcg cagcggtcgg gctgaacggg gggttcgtgc    7260
acacagccca gcttggagcg aacgacctac accgaactga gatacctaca gcgtgagcta    7320
tgagaaagcg ccacgcttcc cgaagggaga aaggcggaca ggtatccggt aagcggcagg    7380
gtcggaacag gagagcgcac gagggagctt ccaggggaa acgcctggta tctttatagt    7440
cctgtcgggt ttcgccacct ctgacttgag cgtcgatttt tgtgatgctc gtcagggggg    7500
cggagcctat ggaaaaacgc cagcaacgcg gccttttac ggttcctggc cttttgctgg    7560
ccttttgctc acatgttctt tcctgcgtta tcccctgatt ctgtggataa ccgtattacc    7620
gcctttgagt gagctgatac cgctcgccgc agccgaacga ccgagcgcag cgagtcagtg    7680
agcgaggaag cggaagagcg cccaatacgc aaaccgcctc tccccgcgcg ttggccgatt    7740
cattaatg                                                            7748
```

<210> SEQ ID NO 13
<211> LENGTH: 1386
<212> TYPE: DNA
<213> ORGANISM: Artificial Sequence
<220> FEATURE:
<223> OTHER INFORMATION: constructed sequence

<400> SEQUENCE: 13

```
atgcagaggg tgaacatgat catggctgag agccctggcc tgatcaccat ctgcctgctg      60
ggctacctgc tgtctgctga gtgcactgtg ttcctggacc atgagaatgc caacaagatc     120
ctgaacaggc ccaagagata caactctggc aagctggagg agtttgtgca gggcaacctg     180
gagagggagt gcatggagga aagtgcagc tttgaggagg ccaggaggt gtttgagaac     240 actgagagga ccactgagtt ctggaagcag tatgtggatg ggaccagtg tgagagcaac     300 ccctgcctga atggggcag ctgcaaggat gacatcaaca gctatgagtg ctggtgcccc     360
tttggctttg agggcaagaa ctgtgagctg gatgtgacct gcaacatcaa gaatggcaga     420
tgtgagcagt tctgcaagaa ctctgctgac aacaaggtgg tgtgcagctg cactgagggc     480
tacaggctgg ctgagaacca gaagagctgt gagcctgctg tgccattccc atgtggcaga     540
gtgtctgtga gccagaccag caagctgacc agggctgagg ctgtgttccc tgatgtggac     600
tatgtgaaca gcactgaggc tgaaaccatc ctggacaaca tcacccagag cacccagagc     660
```

```
ttcaatgact tcaccagggt ggtgggggggg gaggatgcca agcctggcca gttcccctgg    720
caagtggtgc tgaatggcaa ggtggatgcc ttctgtgggg gcagcattgt gaatgagaag    780
tggattgtga ctgctgccca ctgtgtggag actggggtga agatcactgt ggtggctggg    840
gagcacaaca ttgaggagac tgagcacact gagcagaaga ggaatgtgat caggatcatc    900
ccccaccaca actacaatgc tgccatcaac aagtacaacc atgacattgc cctgctggag    960
ctggatgagc ccctggtgct gaacagctat gtgacccca tctgcattgc tgacaaggag     1020
tacaccaaca tcttcctgaa gtttggctct ggctatgtgt ctggctgggg cagggtgttc    1080
cacaagggca ggtctgccct ggtgctgcag tacctgaggg tgccctggt ggacagggcc     1140 acctgcctga ggagcaccaa gttcaccatc tacaacaaca tgttctgtgc tggcttccat    1200 gagggggca gggacagctg ccagggggac tctggggggcc cccatgtgac tgaggtggag    1260
ggcaccagct tcctgactgg catcatcagc tggggggagg agtgtgccat gaagggcaag    1320
tatggcatct acaccaaagt ctccagatat gtgaactgga tcaaggagaa gaccaagctg    1380
acctga                                                               1386
```

<210> SEQ ID NO 14
<211> LENGTH: 738
<212> TYPE: PRT
<213> ORGANISM: Unknown
<220> FEATURE:
<223> OTHER INFORMATION: AAVrh.10 capsid
<400> SEQUENCE: 14

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220
```

```
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
```

```
                      645                 650                 655
Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 15
<211> LENGTH: 727
<212> TYPE: DNA
<213> ORGANISM: Artificial Sequence
<220> FEATURE:
<223> OTHER INFORMATION: constructed sequence

<400> SEQUENCE: 15
agttaatttt taaaaagcag tcaaaagtcc aagtgccctt gcgagcattt actctctctg    60
tttgctctgg ttaataatct caggagcaca aacattcctt actagttcta ggagttaatt   120
tttaaaaagc agtcaaaagt ccaagtgccc ttgcgagcat ttactctctc tgtttgctct   180
ggttaataat ctcaggagca caaacattcc ttactagttc tagagcggcc gccagtgtgc   240
tggaattcgg cttttttagg gctggaagct acctttgaca tcatttcctc tgcgaatgca   300
tgtataattt ctacagaacc tattagaaag gatcacccag cctctgcttt tgtacaactt   360
tcccttaaaa aactgccaat cccactgctg tttggcccaa tagtgagaac ttttttcctgc   420 tgcctcttgg tgcttttgcc tatggcccct attctgcctg ctgaagcaca tcttgccagc   480
atggacttaa ccccctccag ctctgacaat cctctttctc ttttgtttta catgaagggt   540
ctggcagcca aagcaatcac tcaaagttca aaccttatca tttttttgctt tgttcctctt   600 ggccttggtt ttgtacatca gctttgaaaa taccatccca gggttaatgc tggggttaat   660
ttataactga gagtgctcta gttctgcaat acaggacatg ctataaaaat ggaaagatgt   720
tgctttc                                                             727

<210> SEQ ID NO 16
<211> LENGTH: 7198
<212> TYPE: DNA
<213> ORGANISM: Artificial Sequence
<220> FEATURE:
<223> OTHER INFORMATION: constructed sequence

<400> SEQUENCE: 16
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120 agggggttcct tgtagttaat gattaacccg ccatgctact tatctacgta gccatgctct   180
aggaagatcg gaattcgccc ttaagctagg ggggatccac tagtactcga gcctaggag   240 ttaatttta aaaagcagtc aaaagtccaa gtgccttgc gagcatttac tctctctgtt   300
tgctctggtt aataatctca ggagcacaaa cattccttac tagttctagg agttaatttt   360
taaaaagcag tcaaaagtcc aagtgccctt gcgagcattt actctctctg tttgctctgg   420
```

```
ttaataatct caggagcaca acattcctt  actagttcta gagcggccgc cagtgtgctg   480
gaattcggct ttttagggc  tggaagctac ctttgacatc atttcctctg cgaatgcatg   540
tataatttct acagaaccta ttagaaagga tcacccagcc tctgcttttg tacaactttc   600
ccttaaaaaa ctgccaatcc cactgctgtt tggcccaata gtgagaactt tttcctgctg   660
cctcttggtg cttttgccta tggcccctat tctgcctgct gaagacactc ttgccagcat   720
ggacttaaac ccctccagct ctgacaatcc tctttctctt ttgttttaca tgaagggtct   780
ggcagccaaa gcaatcactc aaagttcaaa ccttatcatt ttttgctttg ttcctcttgg   840
ccttggtttt gtacatcagc tttgaaaata ccatcccagg gttaatgctg gggttaattt   900
ataactgaga gtgctctagt tctgcaatac aggacatgct ataaaaatgg aaagatgttg   960
ctttctgaga gatcagctta catgtggtac cgagctcgga tcctgagaac ttcagggtga  1020
gtctatggga cccttgatgt tttctttccc cttcttttct atggttaagt tcatgtcata  1080
ggaaggggag aagtaacagg gtacacatat tgaccaaatc agggtaattt tgcatttgta  1140
attttaaaaa atgctttctt cttttaatat acttttttgt ttatcttatt tctaatactt  1200
tccctaatct ctttctttca gggcaataat gatacaatgt atcatgcctc tttgcaccat  1260
tctaaagaat aacagtgata atttctgggt taaggcaata gcaatatttc tgcatataaa  1320
tatttctgca tataaattgt aactgatgta agaggtttca tattgctaat agcagctaca  1380
atccagctac cattctgctt ttattttatg gttgggataa ggctggatta ttctgagtcc  1440
aagctaggcc ttttgctaa  tcatgttcat acctcttatc ttcctcccac agctcctggg  1500
caacgtgctg gtctgtgtgc tggcccatca ctttggcaaa gaattgatct cgagtaactg  1560
agccgccacc atgcagcgcg tgaacatgat tatgccgag  agccctggcc tgatcaccat  1620
ctgcctgctg ggctacctgc tgagcgccga gtgcaccgtg tttctggacc acgagaacgc  1680
caacaagatc ctgaaccggc ccaagcggta caacagcggc aagctggaag agttcgtgca  1740
gggcaacctg gaacgcgagt gcatggaaga gaagtgcagc ttcgaagagg ccagagaggt  1800
gttcgagaac accgagcgga ccaccgagtt ctggaagcag tacgtggacg gcgaccagtg  1860
cgagagcaac ccctgtctga cggcggcag  ctgcaaggac gacatcaaca gctacgagtg  1920
ctggtgcccc ttcggcttcg agggcaagaa ctgcgagctg gacgtgacct gcaacatcaa  1980
gaacggcagg tgcgagcagt tctgcaagaa cagcgccgac aacaaggtcg tgtgctcctg  2040
caccgagggc tacagactgg ccgagaacca gaagtcctgc gagcccgccg tgccttccc   2100
ttgtggaaga gtgtccgtgt cccagaccag caagctgacc agagccgaga cagtgttccc  2160
cgacgtggac tacgtgaaca gcaccgaggc cgagacaatc ctggacaaca tcacccagag  2220
cacccagtcc ttcaacgact tcaccagagt cgtgggcggc gaggacgcca agcctggaca  2280
gttccctgg  caggtggtgc tgaacggaaa ggtggacgcc ttttgcggcg gcagcatcgt  2340
gaacgagaag tggatcgtga cagccgccca ctgcgtggaa accggcgtga agattacagt  2400
ggtggccggc gagcacaaca tcgaggaaac cgagcacaca gagcagaaac ggaacgtgat  2460
cagaatcatc ccccaccaca actacaacgc cgccatcaac aagtacaacc acgatatcgc  2520
cctgctggaa ctgacgagc  ccctggtgct gaatagctac gtgacccccca tctgtatcgc  2580
cgacaaagag tacaccaaca tctttctgaa gttcggcagc ggctacgtgt ccggctgggg  2640
cagagtgttt cacaagggca gatccgctct ggtgctgcag tacctgagag tgcctctggt  2700
ggaccggggcc acctgtctgc tgagcaccaa gttcaccatc tacaacaaca tgttctgcgc  2760
cggcttcac  gagggcggca gagatagctg tcagggcgat tctggcggcc ctcacgtgac  2820
```

```
agaggtggaa ggcaccagct ttctgaccgg catcatcagc tggggcgagg agtgcgccat   2880 gaagggaag tacggcatct acaccaaggt gtccagatac gtgaactgga tcaaagaaaa    2940
gaccaagctg acatgataaa agcttggatc caatcaacct ctggattaca aaatttgtga   3000
aagattgact ggtattctta actatgttgc tccttttacg ctatgtggat acgctgcttt   3060
aatgcctttg tatcatgcta ttgcttcccg tatggctttc attttctcct ccttgtataa   3120
atcctggttg ctgtctcttt atgaggagtt gtggcccgtt gtcaggcaac gtggcgtggt   3180
gtgcactgtg tttgctgacg caaccccccac tggttggggc attgccacca cctgtcagct   3240
cctttccggg actttcgctt tccccctccc tattgccacg gcggaactca tcgccgcctg   3300
ccttgcccgc tgctggacag gggctcggct gttgggcact gacaattccg tggtgttgtc   3360
ggggaaatca tcgtcctttc cttggctgct cgcctgtgtt gccacctgga ttctgcgcgg   3420
gacgtccttc tgctacgtcc cttcggccct caatccagcg gaccttcctt cccgcggcct   3480
gctgccggct ctgcggcctc ttccgcgtct tcgagatctg cctcgactgt gccttctagt   3540
tgccagccat ctgttgtttg cccctccccc gtgccttcct tgaccctgga aggtgccact   3600
cccactgtcc tttcctaata aaatgaggaa attgcatcgc attgtctgag taggtgtcat   3660
tctattctgg ggggtgggggt ggggcaggac agcaaggggg aggattggga agacaatagc   3720
aggcatgctg gggactcgag ttaagggcga attcccgata aggatcttcc tagagcatgg   3780
ctacgtagat aagtagcatg gcgggttaat cattaactac aaggaacccc tagtgatgga   3840
gttggccact ccctctctgc gcgctcgctc gctcactgag gccgggcgac caaaggtcgc   3900
ccgacgcccg ggctttgccc gggcggcctc agtgagcgag cgagcgcgca gccttaatta   3960
acctaattca ctggccgtcg ttttacaacg tcgtgactgg gaaaaccctg gcgttaccca   4020
acttaatcgc cttgcagcac atccccccttt cgccagctgg cgtaatagcg aagaggcccg   4080
caccgatcgc ccttcccaac agttgcgcag cctgaatggc gaatgggacg cgccctgtag   4140
cggcgcatta agcgcggcgg gtgtggtggt tacgcgcagc gtgaccgcta cacttgccag   4200
cgccctagcg cccgctcctt tcgctttctt cccttccttt ctcgccacgt tcgccggctt   4260
tccccgtcaa gctctaaatc gggggctccc tttagggttc cgatttagtg ctttacggca   4320
cctcgacccc aaaaaacttg attagggtga tggttcacgt agtgggccat cgccctgata   4380
gacggttttt cgccctttga cgttggagtc acgttctttt aatagtggac tcttgttcca   4440
aactggaaca acactcaacc ctatctcggt ctattctttt gatttataag ggattttgcc   4500
gatttcggcc tattggttaa aaaatgagct gatttaacaa aaatttaacg cgaattttaa   4560
caaaatcatg tgagcaaaag gccagcaaaa ggccaggaac cgtaaaaagg ccgcgttgct   4620
ggcgtttttc cataggctcc gcccccctga cgagcatcac aaaaatcgac gctcaagtca   4680
gaggtggcga aacccgacag gactataaag ataccaggcg tttccccctg gaagctccct   4740
cgtgcgctct cctgttccga ccctgccgct taccggatac ctgtccgcct ttctcccttc   4800
gggaagcgtg gcgctttctc atagctcacg ctgtaggtat ctcagttcgg tgtaggtcgt   4860
tcgctccaag ctgggctgtg tgcacgaacc ccccgttcag cccgaccgct gcgccttatc   4920
cggtaactat cgtcttgagt ccaacccggt aagacacgac ttatcgccac tggcagcagc   4980
cactggtaac aggattagca gagcgaggta tgtaggcggt gctacagagt tcttgaagtg   5040
gtggcctaac tacggctaca ctagaagaac agtatttggt atctgcgctc tgctgaagcc   5100
agttaccttc ggaaaaagag ttggtagctc ttgatccggc aaacaaacca ccgctggtag   5160
```

```
cggtggtttt tttgtttgca agcagcagat tacgcgcaga aaaaaggat ctcaagaaga    5220 tcctttgatc ttttctacgg ggtctgacgc tcagtggaac gaaaactcac gttaagggat    5280
tttggtcatg agattatcaa aaaggatctt cacctagatc cttttgatcc tccggcgttc    5340
agcctgtgcc acagccgaca ggatggtgac caccatttgc cccatatcac cgtcggtact    5400
gatcccgtcg tcaataaacc gaaccgctac accctgagca tcaaactctt ttatcagttg    5460
gatcatgtcg gcggtgtcgc ggccaagacg gtcgagcttc ttcaccagaa tgacatcacc    5520
ttcctccacc ttcatcctca gcaaatccag cccttcccga tctgttgaac tgccggatgc    5580
cttgtcggta agatgcggt tagcttttac ccctgcatct ttgagcgctg aggtctgcct    5640
cgtgaagaag gtgttgctga ctcataccag gcctgaatcg ccccatcatc cagccagaaa    5700
gtgagggagc cacggttgat gagagctttg ttgtaggtgg accagttggt gattttgaac    5760
ttttgctttg ccacggaacg gtctgcgttg tcgggaagat gcgtgatctg atccttcaac    5820
tcagcaaaag ttcgatttat tcaacaaagc cgccgtcccg tcaagtcagc gtaatgctct    5880
gccagtgtta caaccaatta accaattctg attagaaaaa ctcatcgagc atcaaatgaa    5940
actgcaattt attcatatca ggattatcaa taccatattt ttgaaaaagc cgtttctgta    6000
atgaaggaga aaactcaccg aggcagttcc ataggatggc aagatcctgg tatcggtctg    6060
cgattccgac tcgtccaaca tcaatacaac ctattaattt cccctcgtca aaaataaggt    6120
tatcaagtga gaaatcacca tgagtgacga ctgaatccgg tgagaatggc aaaagcttat    6180
gcatttcttt ccagacttgt tcaacaggcc agccattacg ctcgtcatca aaatcactcg    6240
catcaaccaa accgttattc attcgtgatt gcgcctgagc gagacgaaat acgcgatcgc    6300
tgttaaaagg acaattacaa acaggaatcg aatgcaaccg gcgcaggaac actgccagcg    6360
catcaacaat attttcacct gaatcaggat attcttctaa tacctggaat gctgttttcc    6420
cggggatcgc agtggtgagt aaccatgcat catcaggagt acggataaaa tgcttgatgg    6480
tcggaagagg cataaattcc gtcagccagt ttagtctgac catctcatct gtaacatcat    6540
tggcaacgct acctttgcca tgtttcagaa acaactctgg cgcatcgggc ttcccataca    6600
atcgatagat tgtcgcacct gattgcccga cattatcgcg agcccattta cccatata    6660 aatcagcatc catgttggaa tttaatcgcg gcctcgagca agacgtttcc cgttgaatat    6720
ggctcataac accccttgta ttactgttta tgtaagcaga cagttttatt gttcatgatg    6780
atatattttt atcttgtgca atgtaacatc agagattttg agacaccatg ttctttcctg    6840
cgttatcccc tgattctgtg gataaccgta ttaccgcctt tgagtgagct gataccgctc    6900
gccgcagccg aacgaccgag cgcagcgagt cagtgagcga ggaagcggaa gagcgcccaa    6960
tacgcaaacc gcctctcccc gcgcgttggc cgattcatta atgcagctgg cacgacaggt    7020
ttcccgactg gaaagcgggc agtgagcgca acgcaattaa tgtgagttag ctcactcatt    7080
aggcacccca ggctttacac tttatgcttc cggctcgtat gttgtgtgga attgtgagcg    7140
gataacaatt tcacacagga aacagctatg accatgatta cgccagattt aattaagg     7198
```

<210> SEQ ID NO 17
<211> LENGTH: 1386
<212> TYPE: DNA
<213> ORGANISM: Artificial Sequence
<220> FEATURE:
<223> OTHER INFORMATION: constructed sequence

<400> SEQUENCE: 17

```
atgcagcgcg tgaacatgat tatggccgag agccctggcc tgatcaccat ctgcctgctg      60
```

| | | |
|---|---|---|
| ggctacctgc tgagcgccga gtgcaccgtg tttctggacc acgagaacgc caacaagatc | 120 | |
| ctgaaccggc caagcggta caacagcggc aagctggaag agttcgtgca gggcaacctg | 180 | |
| gaacgcgagt gcatggaaga gaagtgcagc ttcgaagagg ccagagaggt gttcgagaac | 240 | |
| accgagcgga ccaccgagtt ctggaagcag tacgtgacg cgaccagtg cgagagcaac | 300 | |
| ccctgtctga acggcggcag ctgcaaggac gacatcaaca gctacgagtg ctggtgcccc | 360 | |
| ttcggcttcg agggcaagaa ctgcgagctg gacgtgacct gcaacatcaa gaacggcagg | 420 | |
| tgcgagcagt tctgcaagaa cagcgccgac aacaaggtcg tgtgctcctg caccgagggc | 480 | |
| tacagactgg ccgagaacca gaagtcctgc gagcccgccg tgccttcccc ttgtggaaga | 540 | |
| gtgtccgtgt cccagaccag caagctgacc agagccgaga cagtgttccc cgacgtggac | 600 | |
| tacgtgaaca gcaccgaggc cgagacaatc ctggacaaca tcacccagag cacccagtcc | 660 | |
| ttcaacgact tcaccagagt cgtgggcggc gaggacgcca agcctggaca gttcccctgg | 720 | |
| caggtggtgc tgaacggaaa ggtggacgcc ttttgcggcg gcagcatcgt gaacgagaag | 780 | |
| tggatcgtga cagccgccca ctgcgtggaa accggcgtga agattacagt ggtggccggc | 840 | |
| gagcacaaca tcgaggaaac cgagcacaca gagcagaaac ggaacgtgat cagaatcatc | 900 | |
| ccccaccaca actacaacgc cgccatcaac aagtacaacc acgatatcgc cctgctggaa | 960 | |
| ctggacgagc ccctggtgct gaatagctac gtgaccccca tctgtatcgc cgacaaagag | 1020 | |
| tacaccaaca tctttctgaa gttcggcagc ggctacgtgt ccggctgggg cagagtgttt | 1080 | |
| cacaagggca gatccgctct ggtgctgcag tacctgagag tgcctctggt ggaccgggcc | 1140 | |
| acctgtctgc tgagcaccaa gttcaccatc tacaacaaca tgttctgcgc cggcttttcac | 1200 | |
| gagggcggca gagatagctg tcagggcgat tctggcggcc ctcacgtgac agaggtggaa | 1260 | |
| ggcaccagct ttctgaccgg catcatcagc tgggcgagg agtgcgccat gaaggggaag | 1320 | |
| tacggcatct acaccaaggt gtccagatac gtgaactgga tcaaagaaaa gaccaagctg | 1380 | |
| acatga | 1386 | |

<210> SEQ ID NO 18
<211> LENGTH: 99
<212> TYPE: DNA
<213> ORGANISM: Homo sapiens

<400> SEQUENCE: 18

| | |
|---|---|
| gttaattttt aaaaagcagt caaaagtcca agtggccctt ggcagcattt actctctctg | 60 |
| tttgctctgg ttaataatct caggagcaca aacattcct | 99 |

<210> SEQ ID NO 19
<211> LENGTH: 471
<212> TYPE: DNA
<213> ORGANISM: Homo sapiens

<400> SEQUENCE: 19

| | |
|---|---|
| tagggctgga agctaccttt gacatcattt cctctgcgaa tgcatgtata atttctacag | 60 |
| aacctattag aaaggatcac ccagcctctg cttttgtaca actttcccctt aaaaaactgc | 120 |
| caattccact gctgtttggc ccaatagtga aactttttc ctgctgcctc ttggtgcttt | 180 |
| tgcctatggc ccctattctg cctgctgaag acactcttgc cagcatggac ttaaacccct | 240 |
| ccagctctga caatcctctt tctcttttgt tttacatgaa gggtctggca gccaaagcaa | 300 |
| tcactcaaag ttcaaacctt atcatttttt gctttgttcc tcttggcctt ggttttgtac | 360 |

```
atcagctttg aaaataccat cccagggtta atgctggggt taatttataa ctaagagtgc    420
tctagttttg caatacagga catgctataa aaatggaaag atgttgcttt c             471
```